United States Patent
Oupicky et al.

(10) Patent No.: US 9,545,453 B2
(45) Date of Patent: Jan. 17, 2017

(54) CXCR4 INHIBITING CARRIERS FOR NUCLEIC ACID DELIVERY

(71) Applicant: Wayne State University, Detroit, MI (US)

(72) Inventors: David Oupicky, Canton, MI (US); Jing Li, Madison Heights, MI (US)

(73) Assignee: Wayne State University, Detroit, MI (US)

(*) Notice: Subject to any disclaimer, the term of this patent is extended or adjusted under 35 U.S.C. 154(b) by 42 days.

(21) Appl. No.: 14/351,789

(22) PCT Filed: Oct. 15, 2012

(86) PCT No.: PCT/US2012/060292
§ 371 (c)(1),
(2) Date: Apr. 14, 2014

(87) PCT Pub. No.: WO2013/056250
PCT Pub. Date: Apr. 18, 2013

(65) Prior Publication Data
US 2014/0243397 A1    Aug. 28, 2014

Related U.S. Application Data

(60) Provisional application No. 61/547,490, filed on Oct. 14, 2011.

(51) Int. Cl.
| | | |
|---|---|---|
| *A61K 31/713* | (2006.01) | |
| *A61K 31/7105* | (2006.01) | |
| *A61K 31/395* | (2006.01) | |
| *C07D 257/02* | (2006.01) | |
| *A61K 48/00* | (2006.01) | |
| *A61K 47/48* | (2006.01) | |
| *C08G 69/26* | (2006.01) | |
| *C08G 73/02* | (2006.01) | |
| *C08G 73/06* | (2006.01) | |
| *A61K 51/04* | (2006.01) | |
| *A61K 51/06* | (2006.01) | |
| *C08G 63/685* | (2006.01) | |
| *C12N 15/87* | (2006.01) | |
| *A61K 38/12* | (2006.01) | |

(52) U.S. Cl.
CPC ......... *A61K 48/0041* (2013.01); *A61K 31/395* (2013.01); *A61K 31/713* (2013.01); *A61K 31/7105* (2013.01); *A61K 38/12* (2013.01); *A61K 47/481* (2013.01); *A61K 47/48046* (2013.01); *A61K 47/48192* (2013.01); *A61K 47/48215* (2013.01); *A61K 47/48246* (2013.01); *A61K 51/0482* (2013.01); *A61K 51/06* (2013.01); *C07D 257/02* (2013.01); *C08G 63/685* (2013.01); *C08G 69/26* (2013.01); *C08G 73/028* (2013.01); *C08G 73/06* (2013.01); *C12N 15/87* (2013.01)

(58) Field of Classification Search
CPC ............. A61K 31/395; A61K 31/7105; A61K 48/0041; C07D 257/02
See application file for complete search history.

(56) References Cited

PUBLICATIONS

Le Bon (Bioconjugate Chem. 2004 413-423).*
Bridger et al. (Journal of Medicinal Chemistry, 2010, vol. 53, No. 1250-1260).*
Lin et al. (Bioconjugate Chem. 2007, 18, 138-145.*
Le Bon et al. (Bioconjugate Chem. 2004, 15, 413-423).*
Buerkle, M. A., et al., "Inhibition of the alpha-v Integrins with a Cyclic RGD Peptide Impairs Angiogenesis, Growth and Metastasis of Solid Tumors in vivo," British Journal of Cancer, 2002, pp. 788-795, vol. 86, No. 5.
Chen, J., et al., "Bioreducible Hyperbranched Poly(amido amine)s for Gene Delivery," Biomacromolecules, 2009, pp. 2921-2927, vol. 10, No. 10.
Driessen, W. H. P., et al., "Development of Peptide-targeted Lipoplexes to CXCR4-expressing Rat Glioma Cells and Rat Proliferating Endothelial Cells," Molecular Therapy, Mar. 2008, pp. 516-524, vol. 16, No. 3.
Egorova, A., et al., "Chemokine-derived Peptides as Carriers for Gene Delivery to CXCR4 Expressing Cells," The Journal of Gene Medicine, 2009, pp. 772-781, vol. 11.
Le Bon, B., et al., "AMD3100 Conjugates as Components of Targeted Nonviral Gene Delivery Systems: Synthesis and in vitro Transfection Efficiency of CXCR4-Expressing Cells," Bioconjugate Chemistry, 2004, pp. 413-423, vol. 15, No. 2.
Li, J., et al., "Dual-Function CXCR4 Antagonist Polyplexes to Deliver Gene Therapy and Inhibit Cancer Cell Invasion," Angewandte Chemie (International Ed. in English), 2012, pp. 8740-8743, vol. 51, No. 35.
Liang, X., "CXCR4, Inhibitors and Mechanisms of Action," Chemical Biology & Drug Design, 2008, pp. 97-110, vol. 72, No. 2.
Lin, C., et al., "Novel Bioreducible Poly(amido amine)s for Highly Efficient Gene Delivery," Bioconjugate Chemistry, 2007, pp. 138-145, vol. 18, No. 1.

(Continued)

*Primary Examiner* — Anna Falkowitz
(74) *Attorney, Agent, or Firm* — Senniger Powers LLP

(57) ABSTRACT

The present invention generally relates to carriers including polymers and lipids that comprise a CXCR4 inhibiting moiety. More specifically, these carriers are biodegradable and can be bioreducible polymers that comprise a CXCR4 inhibiting moiety. These carriers can be suitable for delivery of nucleic acids to cells. These carriers and pharmaceutical compositions can be used to treat various conditions including cancers and inflammation conditions.

17 Claims, 30 Drawing Sheets

(56) References Cited

PUBLICATIONS

Manickam, D. S., et al., "Effect of Innate Glutathione Levels on Activity of Redox-Responsive Gene Delivery Vectors," Journal of Controlled Release, 2010, pp. 77-84, vol. 141, No. 1.

Manickam, D. S., et al., "Overexpression of Bcl-2 as a Proxy Redox Stimulus to Enhance Activity of Non-Viral Redox-Responsive Delivery Vectors," Biomaterials, 2008, pp. 2680-2688, vol. 29, No. 17.

Williams, H. A., et al., "A Comparison of PET Imaging Characteristics of Various Copper Radioisotopes," European Journal of Nuclear Medicine and Molecular Imaging, Dec. 2005, pp. 1473-1480, vol. 32, No. 12.

\* cited by examiner

CXCR4 INHIBITING CARRIERS FOR NUCLEIC ACID DELIVERY

FIELD OF THE INVENTION

The present invention generally relates to carriers including polymers and lipids that comprise a CXCR4 inhibiting moiety. More specifically, these carriers are bioreducible, biodegradable, or non-biodegradable carriers that comprise a CXCR4 inhibiting moiety and are suitable for delivery of nucleic acids to cells. These carriers and pharmaceutical compositions comprising the carriers can be used to treat various conditions including cancers and inflammation conditions.

BACKGROUND

There are numerous types of nucleic acid carriers that can be used to deliver genetic material inside cells. Transfection can be achieved using viral methods (ex: viruses, bacteriophages), physical methods (ex: electroporation, lasers, heat, injected nanoparticles) or through chemical based methods such as combining DNA with nanoparticles, cyclodetrins, liposomes, dendrimers or polymers that are then encapsulated by target cells. Polyelectrolyte complexes of nucleic acids with polycations (polyplexes) can be used for delivery of nucleic acids.

The main benefits of bioreducible polycation polymers (BRP) are reduced toxicity and, compared to hydrolytically degradable polycations, better spatial control of disassembly and release of DNA that is localized predominantly to the cytoplasm and nucleus. Improved spatial control of polyplex disassembly has been shown to enhance transfection of several types of nucleic acids (plasmid DNA, mRNA, siRNA) in a number of cancer cell lines. Bioreducible polycations are degraded selectively in the reducing intracellular space. The CXCR4 receptor is expressed on multiple cell types including lymphocytes, hematopoietic stem cells, endothelial and epithelial cells and cancer cells. CXCR4 is a trans-membrane chemokine receptor protein specific for a ligand known as CXCL12. Therapeutics that can act as antagonists and inhibit or block the CXCR4/CXCL12 pathway are important drug targets. Incorporation of known CXCR4 inhibiting moieties into carriers should allow targeting of cells expressing CXCR4. Cyclam compound derivatives that act as CXCR4 inhibitors have been developed, notably the AIDS drug AMD-3100. In addition cyclam derivatives form highly stable complexes with virtually all transition metal ions, particularly, cyclam (1,4,8,11-tetraazacyclotetradecane) a well-known macrocyclic ligand.

While there are many classes of BRP known, a need still exists for polymers that can act as CXCR4 inhibitors. Bioreducible polymers that are suitable for applications where biodegradability is required (i.e., systemic delivery of nucleic acids) and can simultaneously act as CXCR4 inhibitors present a promising dual function approach.

SUMMARY OF INVENTION

Among the various aspects of the invention is a carrier comprising a CXCR4 inhibiting moiety. Specifically, the carrier can be a bioreducible polymer comprising a disulfide group that imparts the capability for the polymer to biodegrade in the reducing environment of a cell. The carrier can also be a biodegradable polymer, or a non-biodegradable polymer comprising a CXCR4 inhibiting moiety. The carrier can also be a lipid comprising a CXCR4 inhibiting moiety. These polymers can act as CXCR4 inhibitors and in some cases can deliver nucleic acids for gene therapy.

One aspect of the invention is a polymer that comprises structural units of a CXCR4 inhibiting moiety and either (i) a structural unit of Formula 11, (ii) a structural unit of Formula 22, (iii) structural units of Formulae 11 and 22, (vi) structural units of Formulae 11 and 88, (vii) structural units of Formulae 22 and 88, (viii) structural units of Formulae 11, 22, and 77, (ix) structural units of Formulae 11, 22, and 88, or (x) structural units of Formulae 11, 22, 77, and 88). The structural units of Formulae 11, 22, 77, and 88 correspond to the following structures:

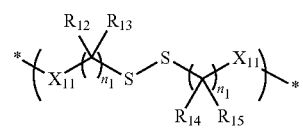

Formula 11

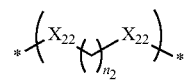

Formula 22

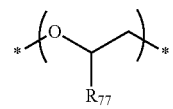

Formula 77

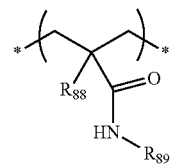

Formula 88 wherein $X_{11}$ and $X_{22}$ are independently —NH—C(O)—CH$_2$CH$_2$—, —O—C(O)—CH$_2$CH$_2$—, —C(O)O—, —C(O)—, or —NH—C(O)—; $R_{77}$ is hydrogen or alkyl; $R_{12}$, $R_{13}$, $R_{14}$, $R_{15}$ are independently hydrogen, alkyl, or substituted alkyl; $R_{88}$ and $R_{89}$ are independently alkyl or substituted alkyl; $n_1$ is independently an integer from 1 to 4; and $n_2$ is an integer from 1 to 8.

The CXCR4 inhibiting monomer can comprise a cyclam monomer and the cyclam monomer can correspond to either Formula 5 or Formula 6, wherein Formulae 5 and 6 correspond to the following structures:

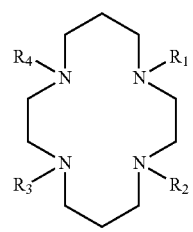

Formula 5

Formula 6

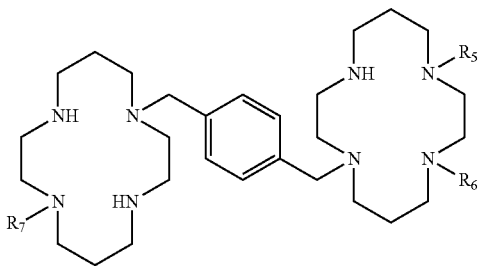

wherein $R_1$, $R_2$, $R_3$, and $R_4$ are independently hydrogen or —$R_8$—$NH_2$; $R_5$, $R_6$, and $R_7$ are independently hydrogen or —$R_8$—$NH_2$; and $R_8$ is independently $C_2$ to $C_{12}$ alkylene, arylene, or $C_2$ to $C_{12}$ alkylene wherein one or more of the —$CH_2$— groups of the alkylene group is replaced with an amide, an amine, a carbonyl, an ether, an ester, a cycloalkyl, an aryl, or a heterocyclo functional group.

Another aspect of the invention is a polymer comprising a reaction product of a polymerization mixture comprising a CXCR4 inhibiting monomer and either (i) a monomer of Formula 1, (ii) a monomer of Formula 2, (iii) a monomer of Formula 12; (iii) monomers of Formulae 1 and 2; (iv) monomers of Formulae 1 and 7, (v) monomers of Formulae 2 and 7, (vi) monomers of Formulae 1 and 8, (vii) monomers of Formulae 2 and 8, (viii) monomers of Formulae 1, 2, and 7, (ix) monomers of Formulae 1, 2, and 8, or (x) monomers of Formulae 1, 2, 7, and 8) the monomers of Formulae 1, 2, 7, and 8 corresponding to the following structures:

Formula 1

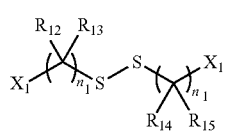

Formula 2

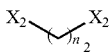

Formula 7

Formula 8

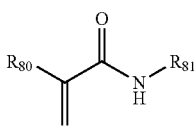

wherein $X_1$ and $X_2$ are independently —NH—C(O)—CH=$CH_2$, —O—C(O)—CH=$CH_2$, —C(O)OH, —C(O)Cl, or —N=C=O; $R_{70}$ is hydrogen or alkyl; $R_{80}$ and $R_{81}$ are independently alkyl or substituted alkyl; $R_{12}$, $R_{13}$, $R_{14}$, $R_{15}$ are independently hydrogen, alkyl, or substituted alkyl; $n_1$ is independently an integer from 1 to 4; and $n_2$ is an integer from 1 to 8.

Yet another aspect of the invention is a polyplex comprising a polymer described herein and a nucleic acid. The nucleic acid can be plasmid DNA, mRNA, antisense oligonucleotide, shRNA, siRNA or microRNA.

A further aspect is pharmaceutical composition comprising a pharmaceutically acceptable excipient and a polymer or a polyplex described herein.

Yet a further aspect is a method for treating breast cancer in a patient, the method comprising administering to the patient a therapeutically effective amount of a polymer, polyplex, or pharmaceutical composition described herein.

Another aspect of the invention is a method for treating prostate cancer in a male patient, the method comprising administering to the male patient a therapeutically effective amount of a polymer, polyplex, or pharmaceutical composition described herein.

Still another aspect is a method for treating lung cancer in a patient, the method comprising administering to the patient a therapeutically effective amount of a polymer, polyplex, or pharmaceutical composition described herein.

Yet another aspect is a method for treating inflammatory bowel disease (IBD) in a patient, the method comprising administering to the patient a therapeutically effective amount of a polymer, polyplex, or pharmaceutical composition described herein.

A further aspect of the invention is a method for inhibiting or reducing metastasis in a patient, the method comprising administering to the patient a polymer, a polyplex, or a pharmaceutical composition described herein.

Yet a further aspect is an imaging method comprising imaging a tissue of a patient using a polymer, a pharmaceutical composition, or a polyplex, wherein the tissue comprises a CXCR4 receptor.

DETAILED DESCRIPTION

Figure 1:
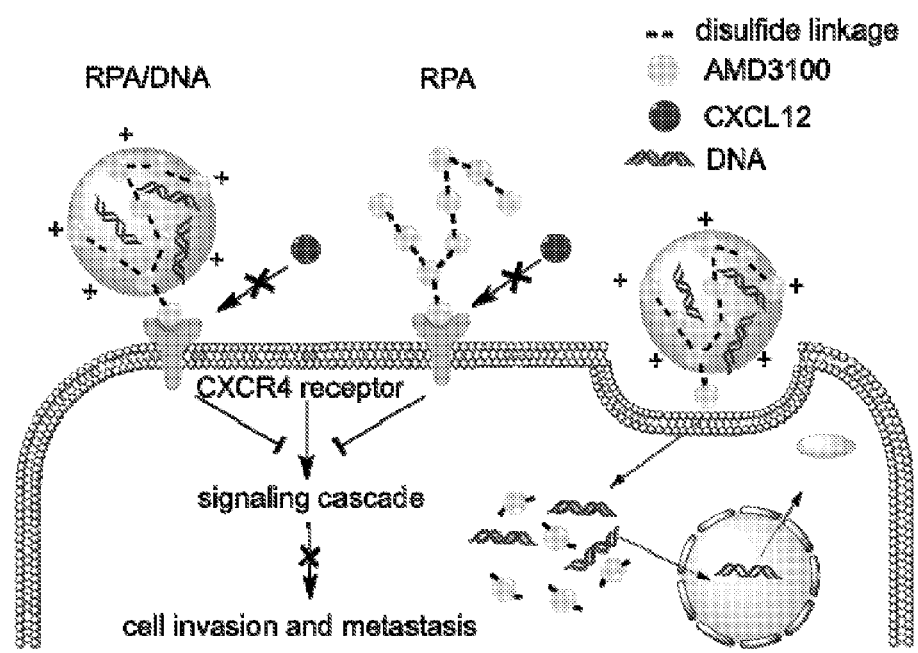
FIG. 1 is a schematic representation of the mechanism of action of CBRP-based polyplexes. Polyplex carriers are assembled from DNA (example: shRNA plasmid) and CBRP polymers and introduced as pharmaceutical formulations. The CXCR4 inhibiting moiety acts as an antagonist to the CXCR4 receptor blocking the CXCL12 ligand and resulting signal cascade pathway. For example, CXCR4 antagonism results in inhibition of cell invasion and metastatic spread of cancer cells. The carrier polyplexes undergo endocytosis and are degraded in the reducing environment of cytoplasm and release the DNA. The released DNA product is then transcribed, (e.g., the shRNA loop is removed by DICER, resulting in processed siRNA). Cells expressing the CXCR4 receptor have increased carrier concentrations surrounding them resulting in enhanced transfection efficiency or more successful gene therapy.

The present invention is directed to polymers that comprise a CXCR4 inhibiting moiety. When these polymers are bioreducible, they are generally called CXCR4 inhibiting bioreducible polymers (CBRPs). These CBRPs can be suitable for delivery of nucleic acids to cells. In addition, polymers that are biodegradable, but are not bioreducible can comprise a CXCR4 inhibiting moiety and can be referred to as NPA. These polymers do not contain a disulfide group. Preferably, the CXCR4 inhibiting moiety is a cyclam derivative. When used for delivery of nucleic acids to cell, the polymers preferably comprise, in addition to the nucleic acids a cRGD for targeting of the polymers to cells. These polymers and their pharmaceutical compositions can be used to treat various conditions including cancers and inflammation conditions, such as breast cancer, prostate cancer, lung cancer, metastasis, and inflammatory bowel disease (IBD). Furthermore, the polymers wherein a metal ion, such as copper(II), zinc(II), cobalt(II) or nickel is complexed with the cyclam monomer or cyclam compound can be used for imaging a tissue of a patient where the tissue comprises a CXCR4 receptor.

The polymer can comprise a reaction product of a polymerization mixture comprising a CXCR4 inhibiting monomer and either (i) a monomer of Formula 1, (ii) a monomer of Formula 2, (iii) monomers of Formulae 1 and 2; (iv) monomer of Formulae 1 and 7, (v) monomers of Formulae 2 and 7, (vi) monomers of Formulae 1 and 8, (vii) monomers of Formulae 2 and 8, (viii) monomers of Formulae 1, 2, and 7, (ix) monomers of Formulae 1, 2, and 8, or (x) monomers of Formulae 1, 2, 7, and 8. The monomers of Formulae 1, 2, 7, and 8 corresponding to the following structures:

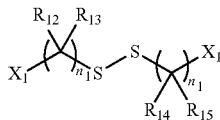

Formula 1

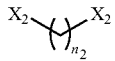

Formula 2

Formula 7

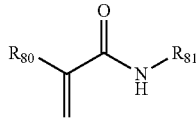

Formula 8 wherein $X_1$ and $X_2$ are independently —NH—C(O)—CH=CH$_2$, —O—C(O)—CH=CH$_2$, —C(O)OH, —C(O)Cl, or —N=C=O; $R_{70}$ is hydrogen or alkyl; $R_{80}$ and $R_{81}$ are independently alkyl or substituted alkyl; $R_{12}$, $R_{13}$, $R_{14}$, $R_{15}$ are independently hydrogen, alkyl, or substituted alkyl; $n_1$ is independently an integer from 1 to 4; and $n_2$ is an integer from 1 to 8.

The polymer can comprise a reaction product of a polymerization mixture comprising a CXCR4 inhibiting monomer and either (i) a monomer of Formula 1, (ii) a monomer of Formula 2, or (iii) monomers of Formulae 1 and 2. When the polymers comprise a monomer of Formula 1, $R_{12}$, $R_{13}$, $R_{14}$, $R_{15}$ are hydrogen.

The polymers can be a bioreducible polymer that is the reaction product of a polymerization mixture that comprises a monomer corresponding to Formula 1. These polymers have an $X_1$ of —NH—C(O)—CH=CH$_2$ or —O—C(O)—CH=CH$_2$; preferably, $X_1$ is —NH—C(O)—CH=CH$_2$. In these polymers, $n_1$ can be 1 to 3, 1 to 2, or 2. Particularly, $n_1$ is 2.

Further, for the monomers of Formula 1, $R_{12}$ and $R_{14}$ are hydrogen and $R_{13}$ and $R_{15}$ are —C(O)O-alkyl. For these monomers, $n_1$ can be 1. Also, the alkyl group can be methyl, ethyl, propyl, butyl, pentyl, or hexyl; preferably, the alkyl group is methyl.

The polymer can also be the reaction product of a polymerization mixture comprising a monomer corresponding to Formula 2. The polymers can have an $X_2$ of —NH—C(O)—CH=CH$_2$ or —O—C(O)—CH=CH$_2$; preferably, $X_2$ is —NH—C(O)—CH=CH$_2$. In these polymers, $n_2$ is an integer from 2 to 8, 3 to 8, 3 to 7, 4 to 7, 5 to 7, or 4 to 6. Particularly, $n_2$ is 6.

Polymers can also comprise monomers corresponding to Formulae 1 and 2.

The polymers described herein can further comprise a monomer of Formula 7. When the polymer comprises a monomer of Formula 7, $R_{70}$ can be hydrogen, methyl, ethyl, or propyl; preferably, $R_{70}$ is hydrogen. $R_{70}$ can also be methyl.

When the polymers comprise a repeat unit derived from a monomer of Formula 8, $R_{80}$ can be methyl, ethyl, propyl, butyl, pentyl, or hexyl. Particularly, $R_{80}$ is methyl. Further, $R_{81}$ can be methyl, ethyl, propyl, butyl, pentyl, hexyl, or substituted methyl, ethyl, propyl, butyl, pentyl, or hexyl. Particularly, $R_{81}$ can be 2-hydroxy propyl.

When the polymer includes a repeat unit derived from a monomer of Formula 7 or 8, the monomers combine to form a block of repeat units. This block of repeat units can comprise from 5 to 60, from 10 to 50, from 20 to 50, from 30 to 50, from 40 to 50, and 45 repeat units. Particularly, the block of repeat units comprises 45 repeat units.

When the polymers of the invention comprise a monomer of Formula 7 or 8, the structural unit derived from the monomer of Formula 7 or 8 can be linked to the structural unit derived from the monomer of Formula 1 or Formula 2 by a linking group. The linking group can comprise a heterocyclo or heteroaryl group. The heterocyclo or heteroaryl group can be benzofuranyl, benzo[d]thiazolyl, benzo[d]thiazolium, isoquinolinyl, isoquinolinium, quinolinyl, quinolinium, thiophenyl, imidazolyl, imidazolium, oxazolyl, oxazolium, furanyl, thiazolyl, thiazolium, pyridinyl, pyridinium, furyl, thienyl, pyridyl, pyrrolyl, pyrrolidinium, indolyl, indolinium, pyrrolidino, pyrrolidinium, piperidino, piperidinium, morpholino, morpholinium, piperazino, piperazinium, succinimide, or a combination thereof.

Further, the linking group can comprise the following structures:

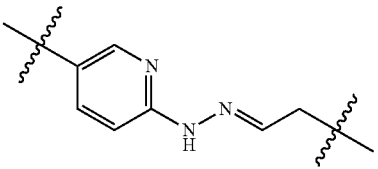

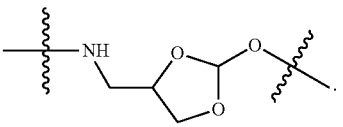

The polymers of the invention can have the CXCR4 inhibiting monomer corresponding to one or more of the following peptide (5-14[C9W, F13-14f] dimer, SDF-1; 1-9 [P2G] dimer, SDF-1; V1 1-9 vMIP-II; T22; T140; T134; ALX40-4C; CGP64222; FC131) or cyclam (AMD3100 or AMD3465) structures:

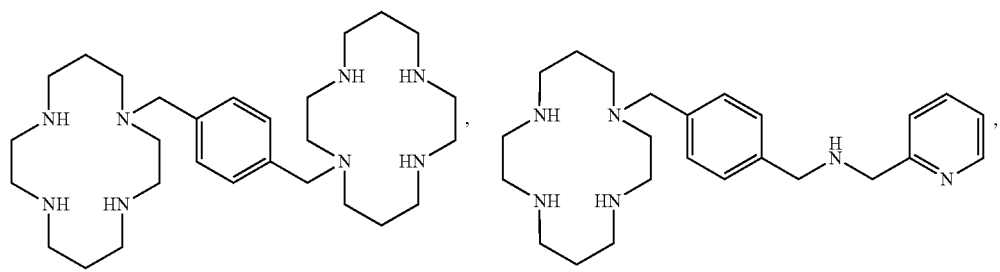
AMD3100, AMD3465
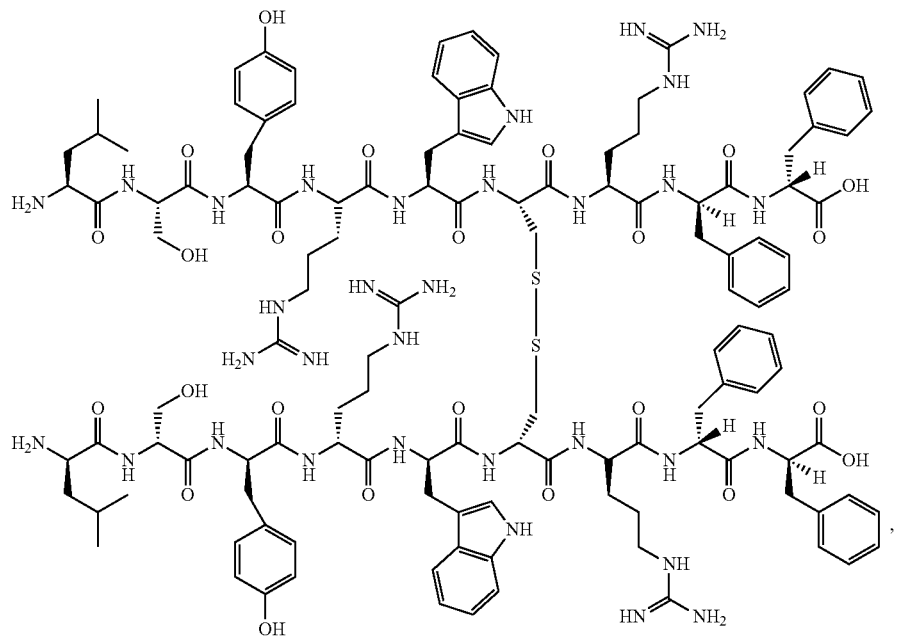
5-14[C9W, F13-14f]
dimer, SDF-1
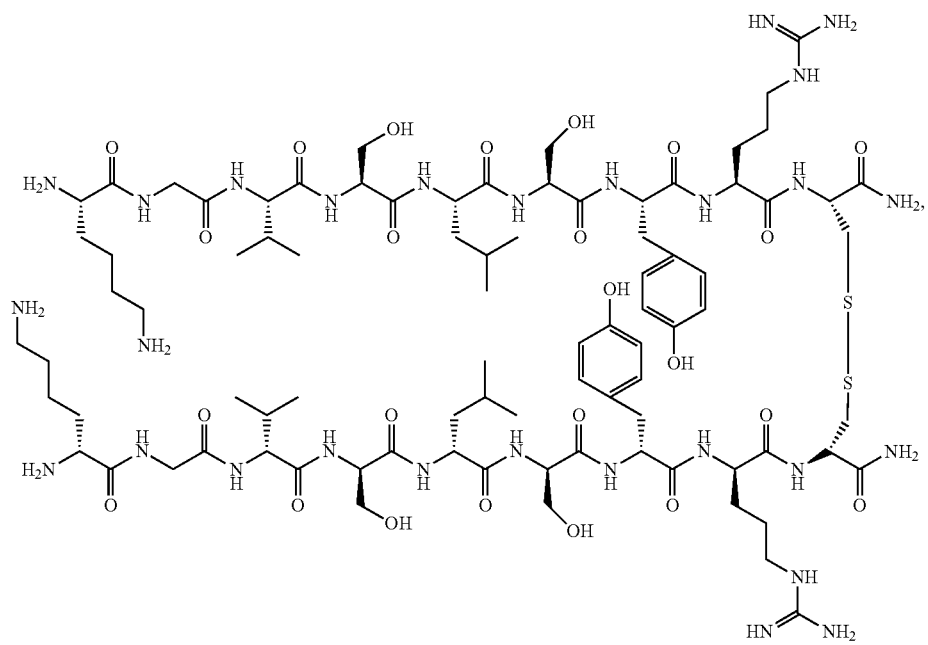
1-9[P2G]dimer
SDF-1

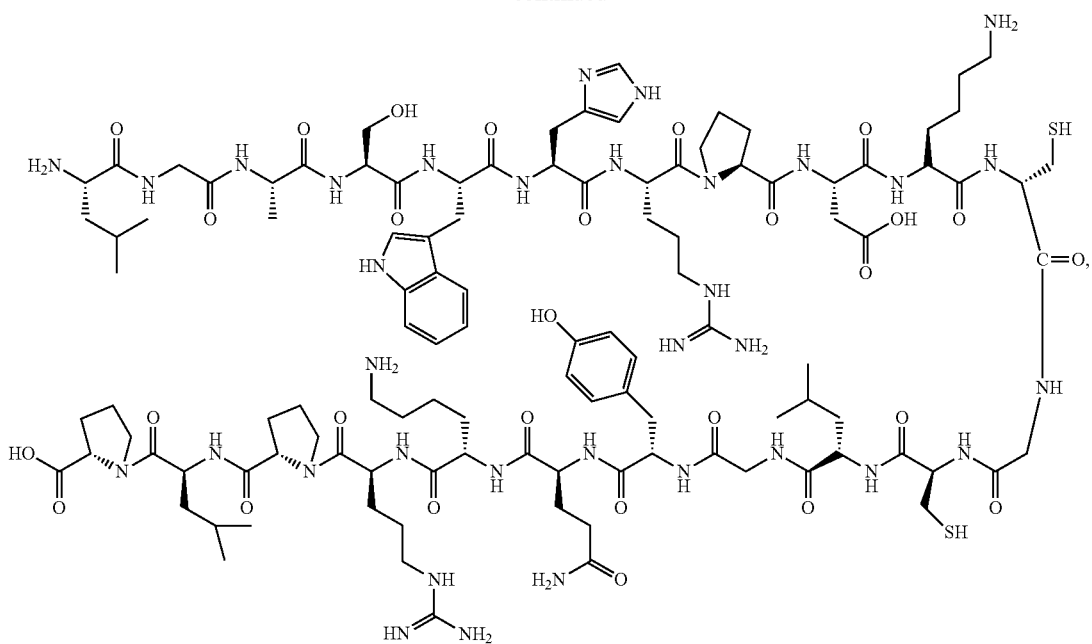
V1
1-9 vMIP-II
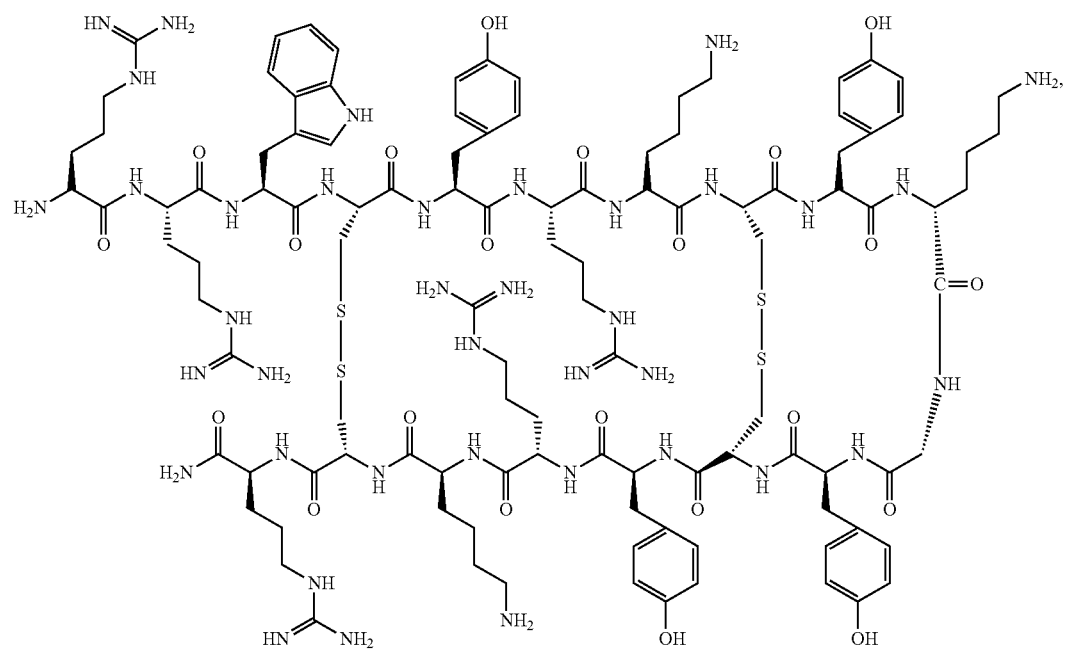
T22

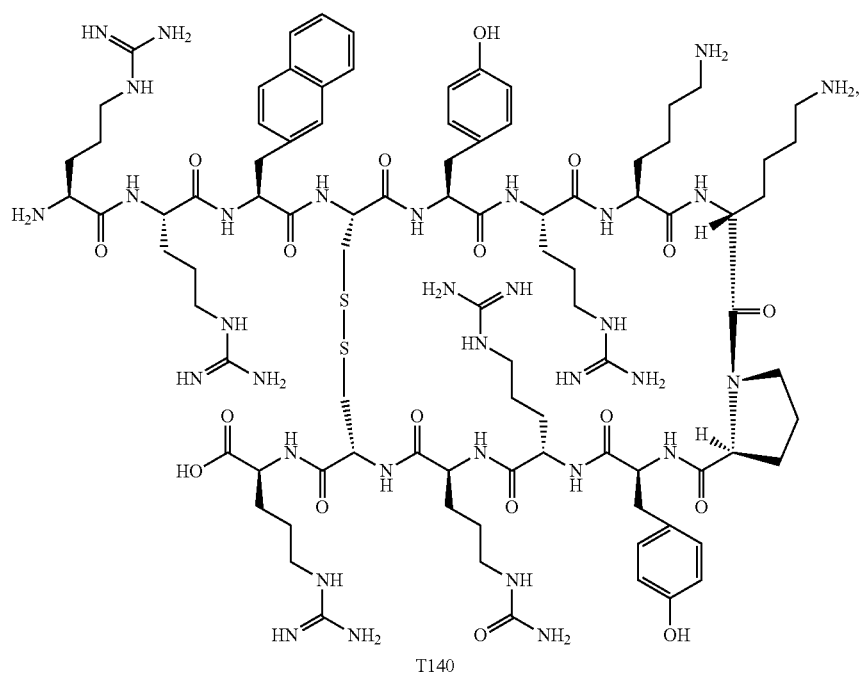
T140
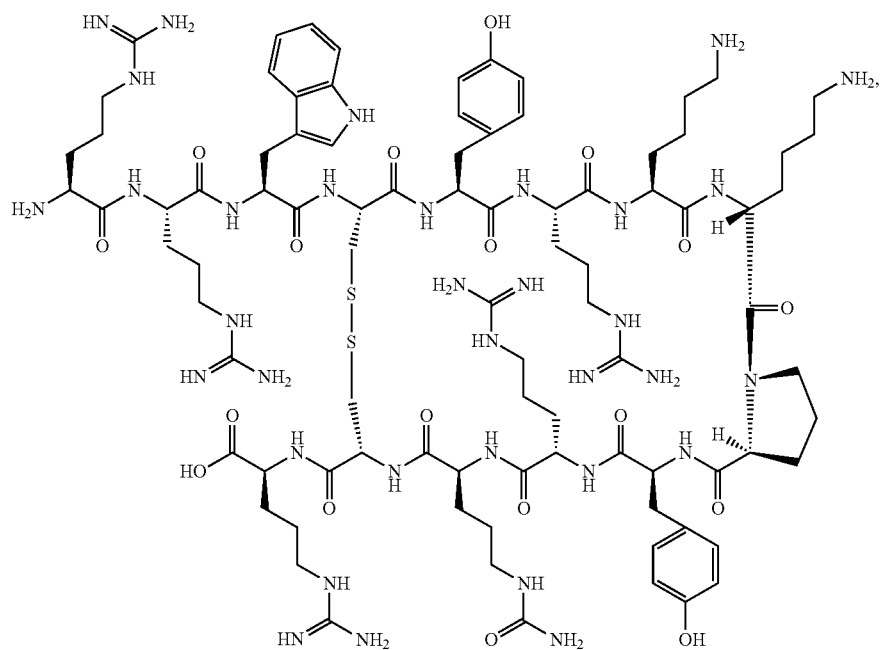
T134

15
16
-continued
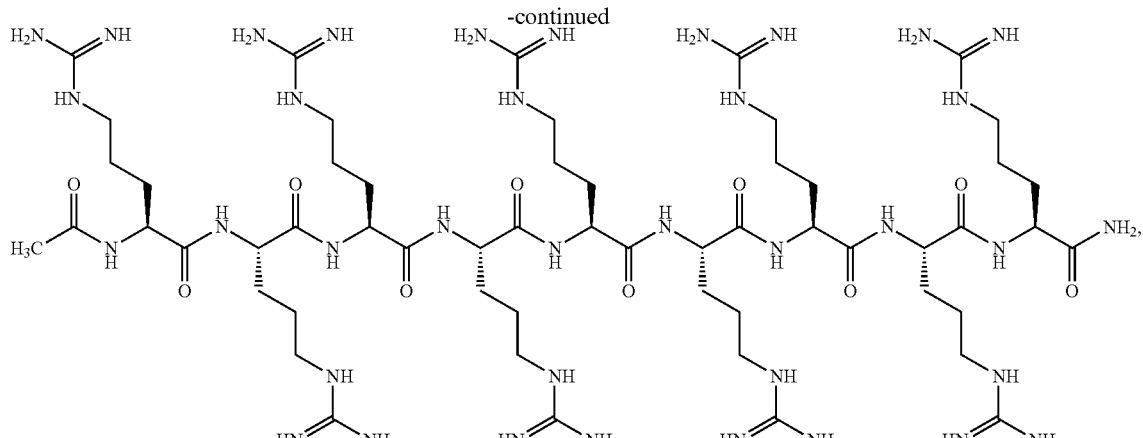
ALX40-4C
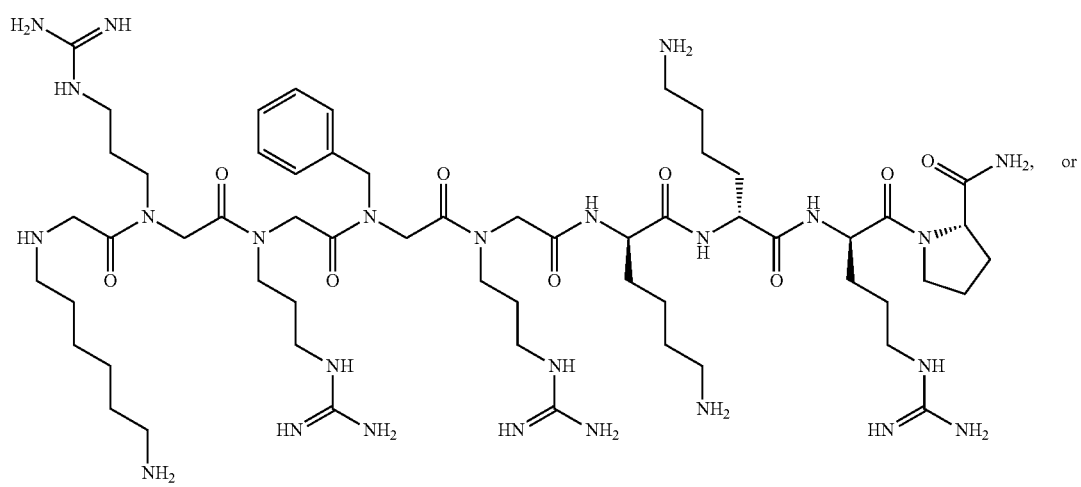
CGP64222
or
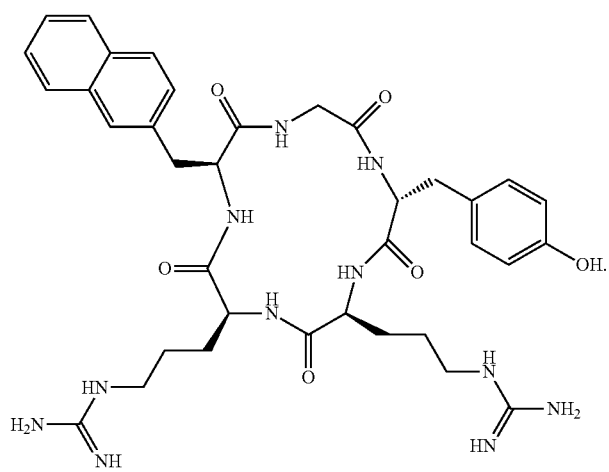
FC131

In other polymers, the CXCR4 inhibiting monomer is a cyclam monomer. In these polymers, the cyclam monomer corresponds to either Formula 5 or Formula 6, wherein Formulae 5 and 6 correspond to the following structures:

Formula 5

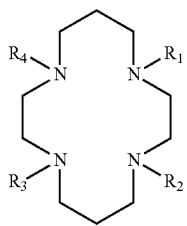

Formula 6

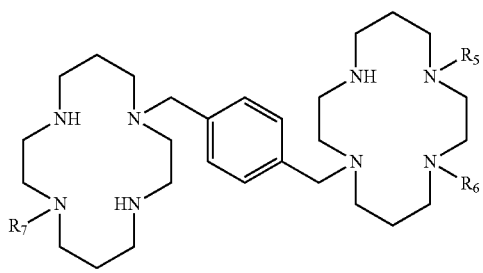

wherein $R_1$, $R_2$, $R_3$, and $R_4$ are independently hydrogen or —$R_8$—$NH_2$; $R_5$, $R_6$, and $R_7$ are independently hydrogen or —$R_8$—$NH_2$; and $R_8$ is independently $C_2$ to $C_{12}$ alkylene, arylene, or $C_2$ to $C_{12}$ alkylene wherein one or more of the —$CH_2$— groups of the alkylene group is replaced with an amide, an amine, a carbonyl, an ether, an ester, a cycloalkyl, an aryl, or a heterocyclo functional group.

These polymers can include a cyclam monomer having a structure corresponding to Formula 5 and at least one of $R_1$, $R_2$, $R_3$, or $R_4$ is —$R_8$—$NH_2$. Other polymers have a cyclam monomer having a structure corresponding to Formula 6 and at least one of $R_5$, $R_6$, or $R_7$ is —$R_8$—$NH_2$. In these polymers having a cyclam monomer corresponding to Formula 5 or 6, $R_8$ is independently —$(CH_2)_2$—O—$(CH_2)_2$—, —$(CH_2)_2$—O—$(CH_2)_2$—O—$(CH_2)_2$—, —$(CH_2)_2$—O—$(CH_2)_2$—O—$(CH_2)_2$—O—$(CH_2)_2$—, —$(CH_2)_2$—N($CH_3$)—$(CH_2)_2$—N($CH_3$)—$(CH_2)_2$—, —$CH_2$—$C_6H_4$—$CH_2$—N($CH_3$)—$(CH_2)_2$—N($CH_3$)—$(CH_2)_2$—, or —$CH_2$—$C_6H_4$—$CH_2$—N($CH_3$)—$CH_2$—$C_5H_3N$—$CH_2$—.
In these polymers having a cyclam monomer corresponding to Formula 5 or 6, $R_8$ is independently —$(CH_2)_2$—O—$(CH_2)_2$—, —$(CH_2)_2$—O—$(CH_2)_2$—O—$(CH_2)_2$—, or —$(CH_2)_2$—O—$(CH_2)_2$—O—$(CH_2)_2$—O—$(CH_2)_2$—.

The polymer of the invention can comprise a structure corresponding to Formula 5 or 6 wherein $R_8$ is independently —$(CH_2)_2$—O—$(CH_2)_2$—, —$(CH_2)_2$—O—$(CH_2)_2$—O—$(CH_2)_2$—, —$(CH_2)_2$—O—$(CH_2)_2$—O—$(CH_2)_2$—O—$(CH_2)_2$—, —$(CH_2)_2$—N($CH_3$)—$(CH_2)_2$—N($CH_3$)—$(CH_2)_2$—, —$CH_2$—$C_6H_4$—$CH_2$—N($CH_3$)—$(CH_2)_2$—N($CH_3$)—$(CH_2)_2$—, —$CH_2$—$C_6H_4$—$CH_2$—N(C(O)Ot-Bu)-$(CH_2)_3$—, —$CH_2$—$C_6H_4$—$CH_2$—N(C(O)Ot-Bu)-$(CH_2)_3$—N(C(O)Ot-Bu)-$(CH_2)_3$—, or —$CH_2$—$C_6H_4$—$CH_2$—N($CH_3$)—$CH_2$—$C_5H_3N$—$CH_2$—. Further, $R_8$ can independently be —$CH_2$—$C_6H_4$—$CH_2$—N(C(O)Ot-Bu)-$(CH_2)_3$— or —$CH_2$—$C_6H_4$—$CH_2$—N(C(O)Ot-Bu)-$(CH_2)_3$—N(C(O)Ot-Bu)-$(CH_2)_3$—.

In a particularly preferred polymer, the polymer is a reaction product of a polymerization mixture comprising a monomer corresponding to Formula 1 wherein $X_1$ is —NH—C(O)—CH=$CH_2$ and $n_1$ is 2, and the CXCR4 inhibiting moiety is a cyclam monomer having a structure corresponding to Formula 6, wherein $R_5$, $R_6$, and $R_7$ are hydrogen.

The polymers can further comprise an amine monomer of Formula 3, the amine monomer of Formula 3 corresponding to the following structure:

$$R_{11}R_{12}N—R_{10}—NH_2 \qquad \text{Formula 3}$$

wherein $R_{10}$ is $C_2$ to $C_{12}$ alkylene, arylene, or $C_2$ to $C_{12}$ alkylene wherein one or more of the —$CH_2$— groups of the alkylene group is replaced with an amine; $R_{11}$ and $R_{12}$ are independently hydrogen, alkyl or aryl. In these polymers, $R_{11}$ and $R_{12}$ are alkyl; preferably, $R_{11}$ and $R_{12}$ are methyl. In these polymers, $R_{10}$ can be butylene. Also, $R_{10}$ can be —$CH_2CH_2CH_2NHCH_2CH_2CH_2$—.

The polymers can comprise structural units of a CXCR4 inhibiting moiety and either (i) a structural unit of Formula 11, (ii) a structural unit of Formula 22, (iii) structural units of Formulae 11 and 22, (vi) structural units of Formulae 11 and 88, (vii) structural units of Formulae 22 and 88, (viii) structural units of Formulae 11, 22, and 77, (ix) structural units of Formulae 11, 22, and 88, or (x) structural units of Formulae 11, 22, 77, and 88); the structural units of Formulae 11, 22, 77, and 88 structural units of Formulae 11, 22, 77, and 88 correspond to the following structures:

Formula 11

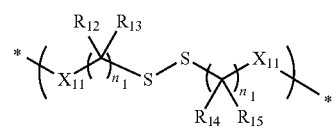

Formula 22

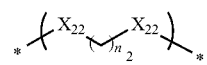

Formula 77

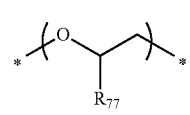

Formula 88

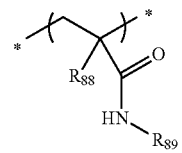

wherein $X_{11}$ and $X_{22}$ are independently —NH—C(O)—$CH_2CH_2$—, —O—C(O)—$CH_2CH_2$—, —C(O)O—, —C(O)—, or —NH—C(O)—; $R_{77}$ is hydrogen or alkyl; $R_{12}$, $R_{13}$, $R_{14}$, $R_{15}$ are independently hydrogen, alkyl, or substituted alkyl; $R_{88}$ and $R_{89}$ are independently alkyl or substituted alkyl; $n_1$ is independently an integer from 1 to 4; and $n_2$ is an integer from 1 to 8.

The polymers can comprise (i) a structural unit of Formula 11, (ii) a structural unit of Formula 22, or (iii) structural units of Formulae 11 and 22. When the polymers comprise a structural unit of Formula 11, $R_{12}$, $R_{13}$, $R_{14}$, $R_{15}$ are hydrogen.

Further, for the structural units of Formula 11, $R_{12}$ and $R_{14}$ are hydrogen and $R_{13}$ and $R_{15}$ are —C(O)O-alkyl. For these monomers, $n_1$ can be 1. Also, the alkyl group can be methyl, ethyl, propyl, butyl, pentyl, or hexyl; preferably, the alkyl group is methyl.

The structural units of Formulae 11, 22, 77, and 88 can also be represented by the structural units of Formulae 11, 22, 77, and 88, which correspond to the following structures:

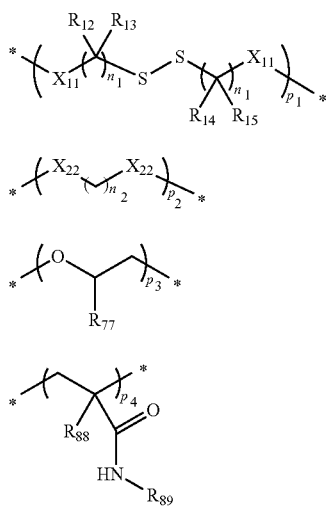

Formula 11A

Formula 22A

Formula 77A

Formula 88A wherein $X_{11}$, $X_{22}$, $R_{12}$, $R_{13}$, $R_{14}$, $R_{15}$, $R_{77}$, $R_{88}$, $R_{89}$, $n_1$, and $n_2$ are defined in connection with Formulae 11, 22, 77, and 88; $p_1$ and $p_2$ are independently integers equal to or greater than 2, 3, 4, 5, 10, 15, 20, 25, 30, 32, 34 or more; and $p_3$ and $p_4$ are independently integers from 5 to 60. Further, $p_1$ and $p_2$ are independently from 2 to 35, from 3 to 35, from 4 to 35, from 5 to 35, from 6 to 35, or from 7 to 35. Also, $p_3$ and $p_4$ are independently integers from 10 to 50, from 20 to 50, from 30 to 50, from 40 to 50, and 45.

Many polymers are bioreducible polymers and comprise a structural unit corresponding to Formula 11. In these polymers, preferably, $X_{11}$ is —NH—C(O)—CH$_2$CH$_2$— or —O—C(O)—CH$_2$CH$_2$—; more preferably, $X_1$ is —NH—C(O)—CH$_2$CH$_2$—. In these polymers, $n_1$ can be 1 to 3, 1 to 2, or 2. Particularly, $n_1$ is 2.

Some polymers comprise a structural unit corresponding to Formula 22. In these polymers, preferably, $X_{22}$ is —NH—C(O)—CH$_2$CH$_2$— or —O—C(O)—CH$_2$CH$_2$—; more preferably, $X_{22}$ is —NH—C(O)—CH$_2$CH$_2$—. In these polymers, $n_2$ is an integer from 2 to 8, 3 to 8, 3 to 7, 4 to 7, 5 to 7, 4 to 6, or 6. Particularly, $n_2$ is 6.

Polymers of the invention can also comprise structural units corresponding to Formulae 11 and 22.

The polymers described herein can further comprise a structural unit of Formula 77. When the polymers comprise a monomer of Formula 77, $R_{77}$ can be hydrogen, methyl, ethyl, or propyl; preferably, $R_{77}$ is hydrogen. $R_{77}$ can also be methyl.

When the polymers comprise a repeat unit of Formula 88, $R_{88}$ can be methyl, ethyl, propyl, butyl, pentyl, or hexyl. Particularly, $R_{80}$ is methyl. Further, $R_{89}$ can be methyl, ethyl, propyl, butyl, pentyl, hexyl, or substituted methyl, ethyl, propyl, butyl, pentyl, or hexyl. Particularly, $R_{89}$ can be 2-hydroxy propyl.

When the polymer includes a repeat unit of Formulae 77 or 88, the monomers combine to form a block of repeat units. This block of repeat units can comprise from 5 to 60, from 10 to 50, from 20 to 50, from 30 to 50, from 40 to 50, and 45 repeat units. Particularly, the block of repeat units comprises 45 repeat units of Formula 77 or 88.

When the polymers of the invention comprise a structural unit of Formula 77 or 88, the structural unit of Formula 77 or 88 can be linked to the structural unit of Formula 11 or Formula 22 by a linking group. The linking group can comprise a heterocyclo or heteroaryl group. The heterocyclo or heteroaryl group can be benzofuranyl, benzo[d]thiazolyl, benzo[d]thiazolium, isoquinolinyl, isoquinolinium, quinolinyl, quinolinium, thiophenyl, imidazolyl, imidazolium, oxazolyl, oxazolium, furanyl, thiazolyl, thiazolium, pyridinyl, pyridinium, furyl, thienyl, pyridyl, pyrrolyl, pyrrolidinyl, indolyl, indolinium, pyrrolidino, pyrrolidinium, piperidino, piperidinium, morpholino, morpholinium, piperazino, piperazinium, succinimide, or a combination thereof.

Further, the linking group can comprise the following structures:

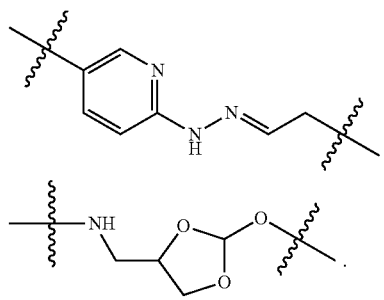

When preparing polymers incorporating a structural unit of Formula 77 or 88, the block of repeat units can be reacted in its polymeric form with the reactive end groups of the structural units of Formulae 11 or 22 or the block of repeat units can be prepared by reacting the monomeric units of Formulae 7 and 8 to form the block of repeat units of Formula 77 or 88.

These polymers can have a molecular weight of from 4 to 20 kilodalton (kDa).

In the polymers described herein, the CXCR4 inhibiting moiety can be derived from one or more of peptide (5-14 [C9W, F13-14f] dimer, SDF-1; 1-9[P2G] dimer, SDF-1; V1 1-9 vMIP-II; T22; T140; T134; ALX40-4C; CGP64222; FC131) or cyclam (AMD3100 or AMD3465) structures described herein above.

For these polymers, the CXCR4 inhibiting moiety is derived from a cyclam compound. The cyclam compound corresponds to the structure of either Formula 5 or Formula 6 as described herein.

Particularly, the polymers comprising a CXCR4 inhibiting moiety can be prepared as follows:

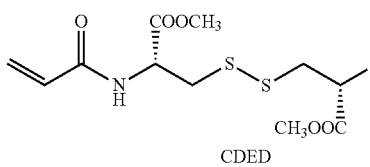

CDED

OR

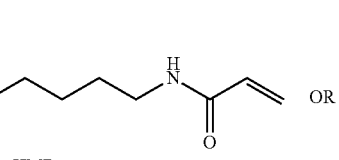

HMBA

OR

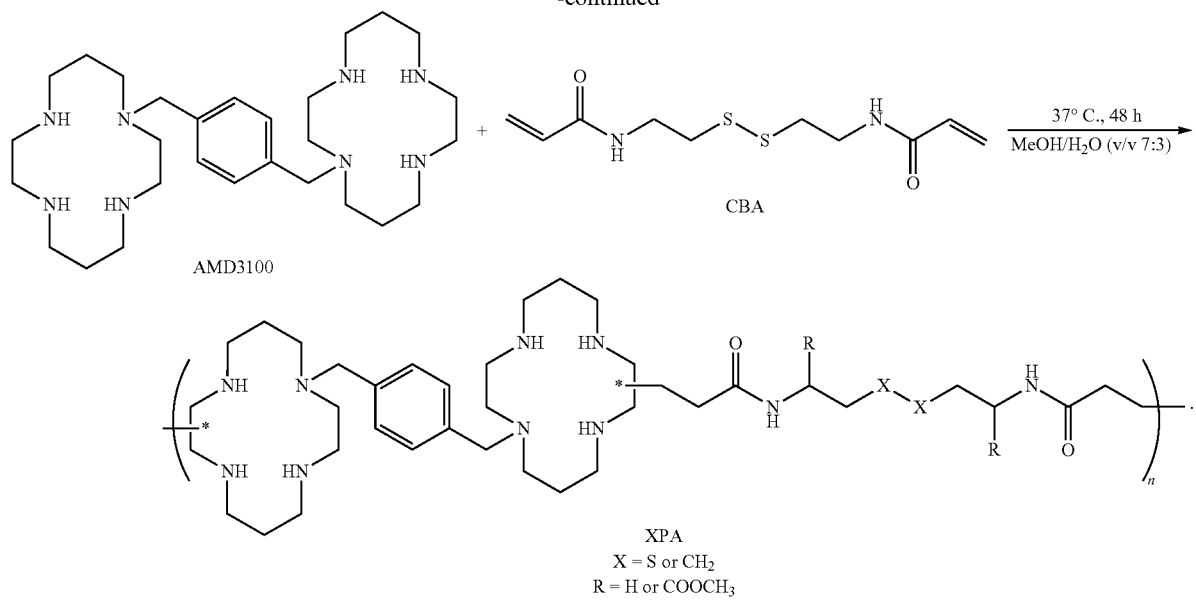
Further, with respect to the synthetic scheme above, the AMD3100 could be substituted with a cyclam of formula 5 as described herein.
For example, a specific polymer known as CopCX can be prepared according to the following synthetic scheme using Michael addition conducted in methanol or methanol/water (7/3 v/v) at 37 C. Molar ratio of PEG to C1 and C2-containing block can be 1:1 or 2:1.
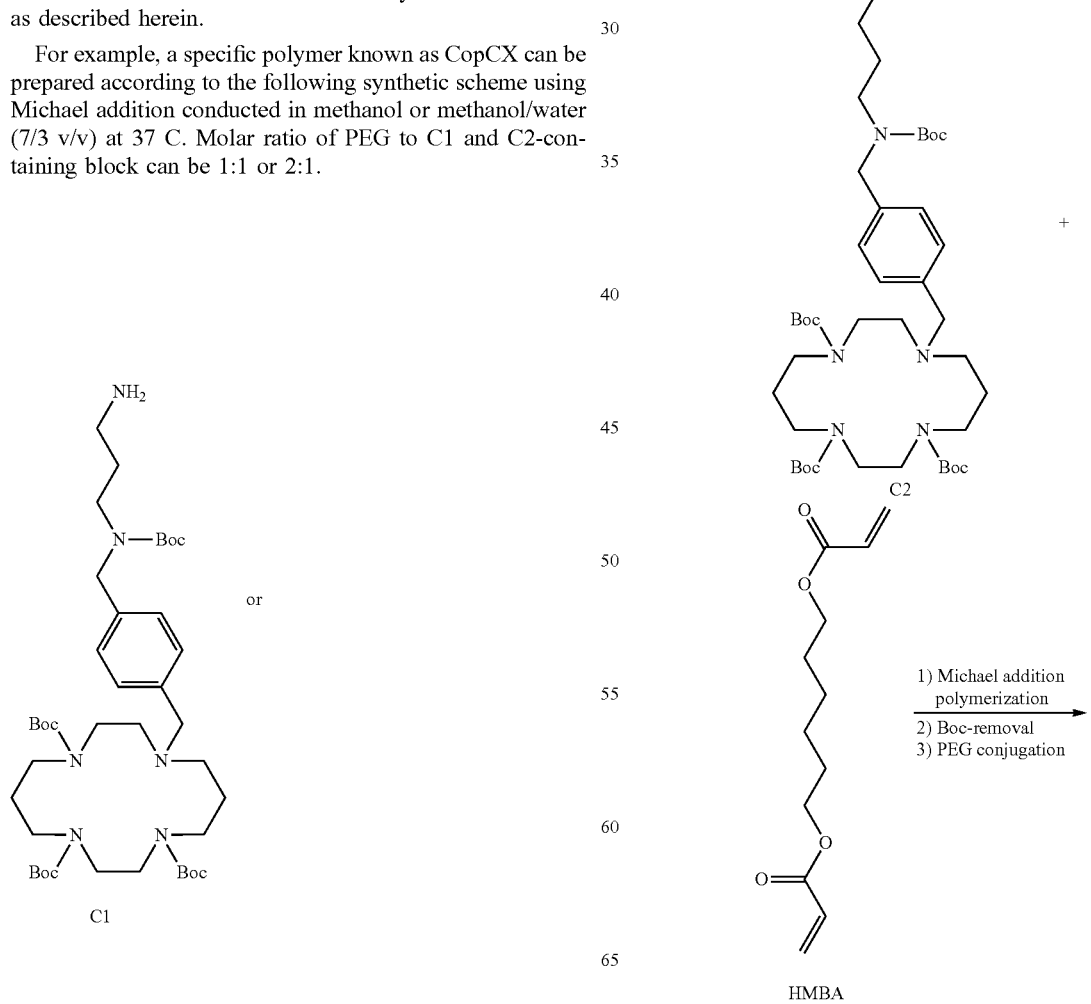

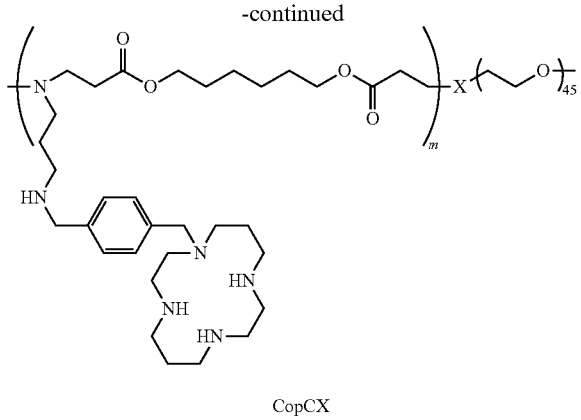

CopCX

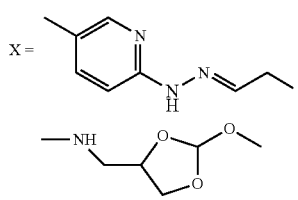

The PEG conjugation can incorporate a polyethylene glycol (PEG) polymer that is already prepared or the polyethylene glycol could be synthesized from an epoxide monomer.

In a particularly preferred polymer, the polymer comprises structural units of Formula 11 wherein $X_1$ is —NH—C(O)—CH$_2$CH$_2$— and $n_1$ is 2, and the CXCR4 inhibiting moiety is derived from a cyclam monomer having a structure corresponding to Formula 66, wherein $R_{65}$, $R_{66}$, and $R_{67}$ are hydrogen.

The polymers can further comprise an amine structural unit of Formula 33. The amine structural unit of Formula 33 corresponds to the following structure:

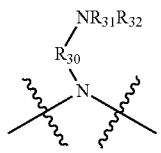

Formula 33 wherein $R_{30}$ is $C_2$ to $C_{12}$ alkylene, arylene, or $C_2$ to $C_{12}$ alkylene wherein one or more of the —CH$_2$— groups of the alkylene group is replaced with an amine; and $R_{31}$ and $R_{32}$ are independently hydrogen, alkyl, or aryl.

In preferred polymers, $R_{31}$ and $R_{32}$ are alkyl; preferably, $R_{31}$ and $R_{32}$ are methyl. For these preferred polymers, $R_{30}$ can be butylene. In other polymers, $R_{30}$ is —CH$_2$CH$_2$CH$_2$NHCH$_2$CH$_2$CH$_2$—.

The polymers of the invention have a weight average molecular weight from about 1.5 kDa to about 20 kDa; preferably, from about 4 kDa to about 15 kDa. For the polymers of the invention, the molar ratio of the CXCR4 inhibiting monomer or CXCR4 inhibiting moiety to the monomer of Formulae 1 or 2 or the structural unit of Formulae 11 or 22 is from about 2:1 to about 1:2; preferably, the molar ratio of the CXCR4 inhibiting monomer or CXCR4 inhibiting moiety to the monomer of Formulae 1 or 2 or the structural unit of Formulae 11 or 22 is from about 1.5:1 to about 1:1.5.

The polymers can further comprise a cyclic RGD peptide. The cyclic RGD peptide can comprise cyclo(Arg-Gly-Asp-D-Phe-Cys), cyclo(Arg-Gly-Asp-D-Phe-Lys), H-Glu[cyclo(Arg-Gly-Asp-D-Phe-Lys)]$_2$, DOTA-Glu-[cyclo(Arg-Gly-Asp-D-Phe-Lys)]$_2$, H-Arg-Gly-Asp-Ser-Lys-OH, cyclo(Arg-Gly-Asp-D-Tyr-Lys), or a combination thereof. Preferably, the cyclic RGD peptide comprises cyclo(Arg-Gly-Asp-D-Phe-Cys).

Additionally, a lipid can comprise a CXCR4 inhibiting moiety and an amine moiety of Formula 9, the amine moiety of Formula 9 corresponding to the following structure:

Formula 9 wherein $R_{81}$, $R_{82}$, and $R_{83}$ are independently alkyl and at least one of $R_{81}$, $R_{82}$, and $R_{83}$ is a $C_{10}$ to $C_{50}$ alkyl. For these lipids, at least one of $R_{81}$, $R_{82}$, and $R_{83}$ can be $C_{10}$ to $C_{30}$ alkyl; at least two of $R_{81}$, $R_{82}$, and $R_{83}$ is a $C_{10}$ to $C_{50}$ alkyl. Preferably, at least two of $R_{81}$, $R_{82}$, and $R_{83}$ is a $C_{10}$ to $C_{30}$ alkyl.

For the lipid comprising an amine moiety of Formula 9, $R_{81}$ can be methyl, ethyl, propyl, or butyl; and $R_{82}$ and $R_{83}$ can be independently $C_{10}$ to $C_{30}$ alkyl. Preferably, $R_{81}$ is methyl and $R_{82}$ and $R_{83}$ are independently $C_{14}$ to $C_{20}$ alkyl.

Specifically, the lipid can have the following formula known as CXLip synthesized by step-wise alkylation of the cyclam with the corresponding oligoamine linker and lipid moiety:

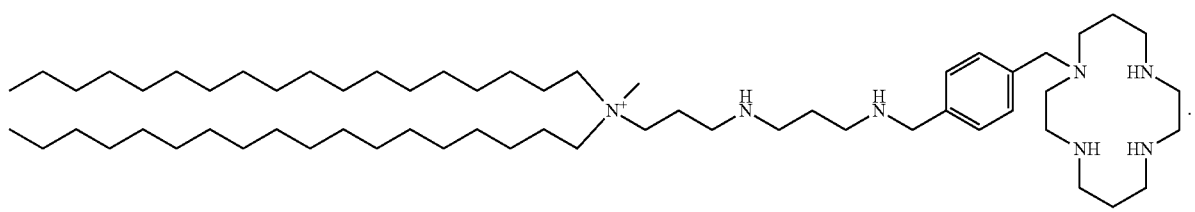 [SMILES: CCCCCCCCCCCCCCCCCC[N+](C)(CCCCCCCCCCCCCCCCCC)CCCNCCCNCc1ccc(CN2CCCNCCNCCCNCC2)cc1]

Further, a lipid can comprise a CXCR4 inhibiting moiety, an amine moiety of Formula 10, and a linker. The amine moiety of Formula 10 corresponds to the following structure:

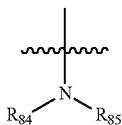

Formula 10 wherein $R_{84}$ and $R_{85}$ are independently alkyl and at least one of $R_{84}$ and $R_{85}$ is a $C_{10}$ to $C_{50}$ alkyl, the linker being a $C_6$ to $C_{15}$ alkylene wherein one or more of the —$CH_2$— groups is replaced by an aryl, an amine, a —C(O)— group, or a combination thereof.

For the lipid comprising Formula 10, $R_{84}$ and $R_{85}$ can independently be $C_{10}$ to $C_{50}$ alkyl. Additionally, the linker is a $C_6$ to $C_{15}$ alkylene wherein two or more of the —$CH_2$— groups is replaced by an amine. Specifically, the linker can be —$CH_2$—$C_6H_4$—$CH_2$—$NR_{86}$—$(CH_2)_o$—$NR_{86}$—$(CH_2)_o$— wherein $R_{86}$ can be hydrogen or alkyl and o can be an integer of 2 or 3. Further, the linker can be —$CH_2$—$C_6H_4$—$CH_2$—$NR_{86}$—$(CH_2)_o$—$NR_{86}$—$(CH_2)_o$—$NR_{86}$—$(CH_2)_o$— wherein $R_{86}$ can be hydrogen or alkyl and o can be an integer of 2 or 3. Preferably, $R_{86}$ is hydrogen. When the linker is substituted with an aryl group, the aryl group can be substituted as a para-phenylene group.

The polymers and lipids can further comprise a polyethylene glycol linking moiety between the cyclic RGD peptide and the polymer or lipid. This polyethylene glycol linking moiety can be derived from a PEG crosslinking moiety having a structure corresponding to Formula 4:

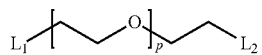

wherein $L_1$ and $L_2$ are independently derived from a sulfhydryl-reactive group or an amine-reactive group. The sulfhydryl-reactive group can be a maleimide group and the amine-reactive group can be a N-hydroxysuccinimide group.

Concerning the above methods, the polymer or lipid and the cyclic RGD peptide can be linked either directly or indirectly. In cases where linking is indirect, a polyethylene glycol (PEG) linking moiety can be used. It is especially useful to use PEG when administration of pharmaceutical compositions is systemic.

The polymers or lipids can further comprise a metal ion complexed with the cyclam monomer or compound. The metal ion can be copper(II), zinc(II), cobalt(II), nickel(II), manganese(II) or a combination thereof. Preferably, the metal ion comprises $^{64}Cu^{2+}$.

The invention is further directed to a polyplex comprising a polymer or lipid described herein and a nucleic acid. The nucleic acid can be plasmid DNA, messenger RNA, antisense oligonucleotides, shRNA, siRNA or microRNA.

The carriers (e.g., polymers or lipids) described herein can also be combined with a pharmaceutically acceptable excipient to form a pharmaceutical composition.

The polymers described herein can generally be synthesized by Michael addition of a CXCR4 inhibiting monomer to a monomer of Formulae 1 or 2 or a combination of Formulae 1 and 2. The monomers are weighed and dissolved in a polar solvent such as methanol/water and allowed to react for up to 48 hours at 37° C. in the dark.

Particularly, a cyclam compound of Formulae 5 or 6 is dissolved in a polar solvent with a monomer of Formula 1 and allowed to react for up to 48 hours at 37° C. in the dark. Once reaction is completed, hydrochloric acid in ethanol (1.25 M) is added to form the HCl salt of the polymers. The precipitated products are centrifuged and washed with ethanol twice to remove extra acid. The products are dried using a vacuum pump and redissolved in water. After dialysis against water for 2 days (MWCO 3,500), the polymers are lyophilized and ready to use. Specifically, the poly(AMD-CBA) can be prepared as described in Scheme 2.

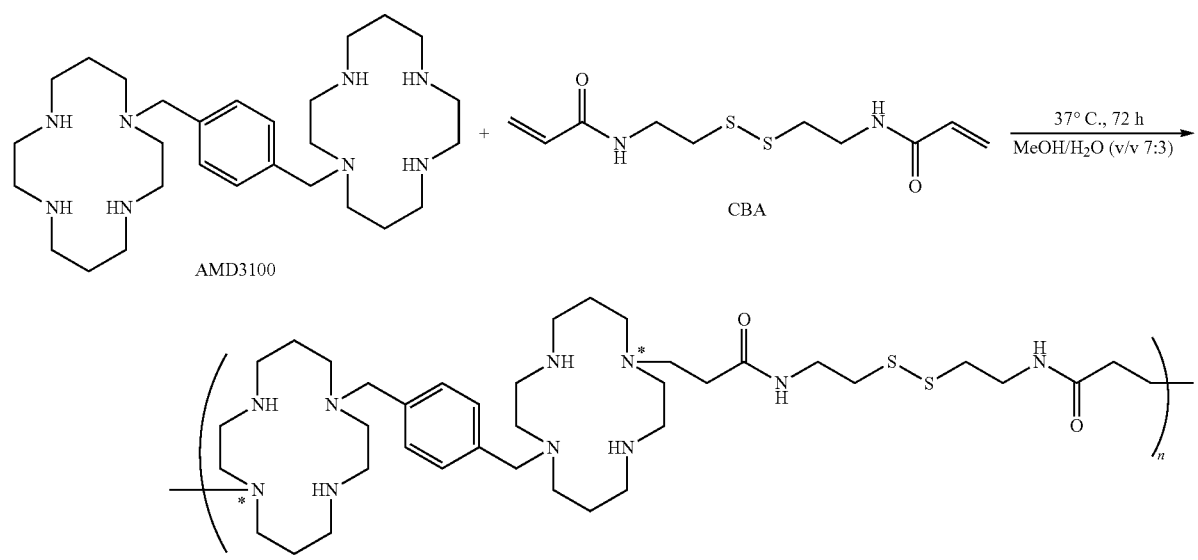

* could be any secondary amine and could have multiple attachments to the same ring Some of the cyclam monomers are commercially available and can be modified according to the following scheme wherein the cyclam reacts with a protecting group (PG) then reacts with an alkyl halide, optionally carrying a functional group such as an amine and then followed by a deprotection reaction.

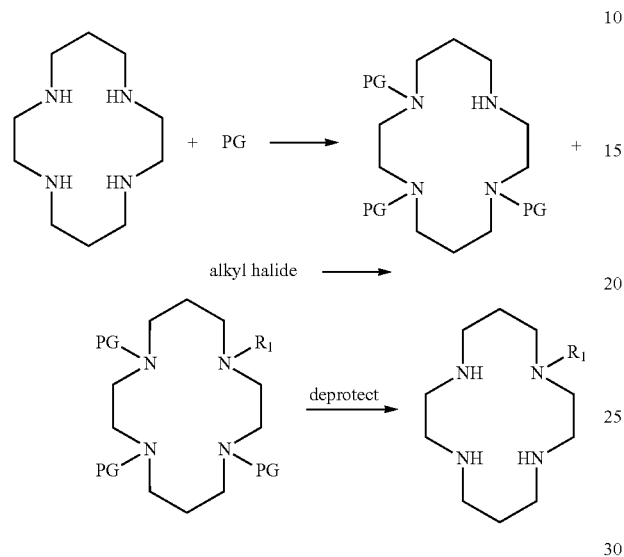

Specifically, these cyclams can be modified as described in more detail in Scheme 3 below.

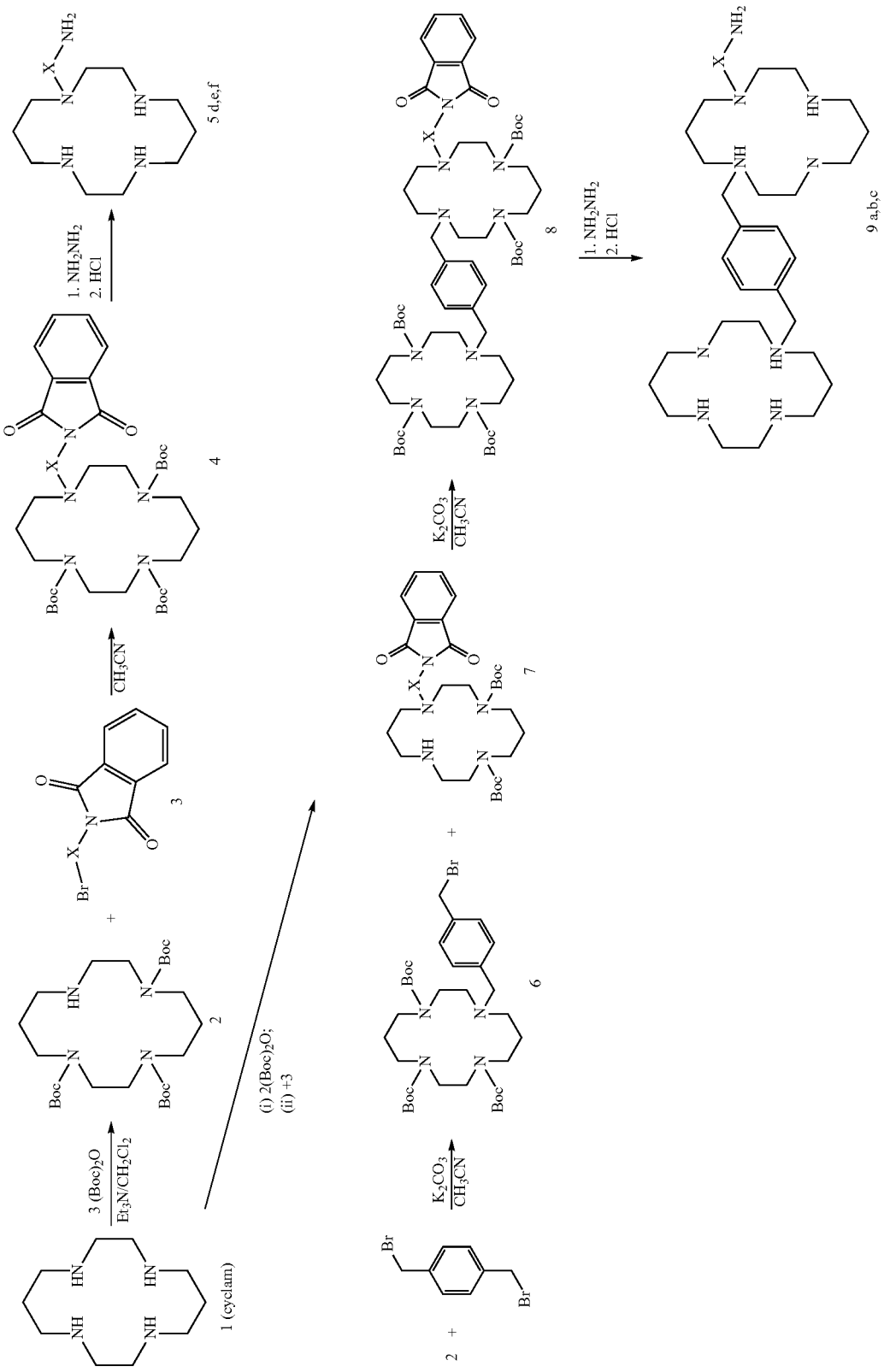

-continued
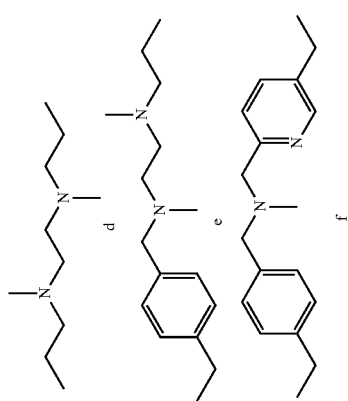
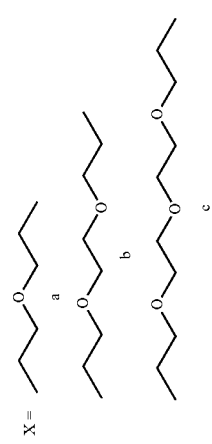

When modifying the cyclam compounds it is useful to consider the amine groups that are needed for binding to the CXCR4 receptor site. These amines are indicated in the following structure in bold blue.

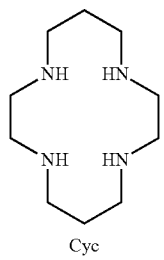
Cyc

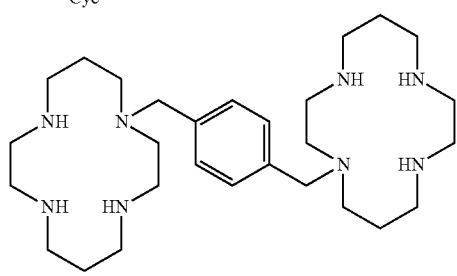
AMD3100

For these polymers there can be different polymer architectures such as hyperbranched cyclam bioreducible polymers (HB-CBRP), linear side chain functionalized CBRP (LSC-CBRP), and linear-terminus-functionalized CBRP (LT-CBRP).

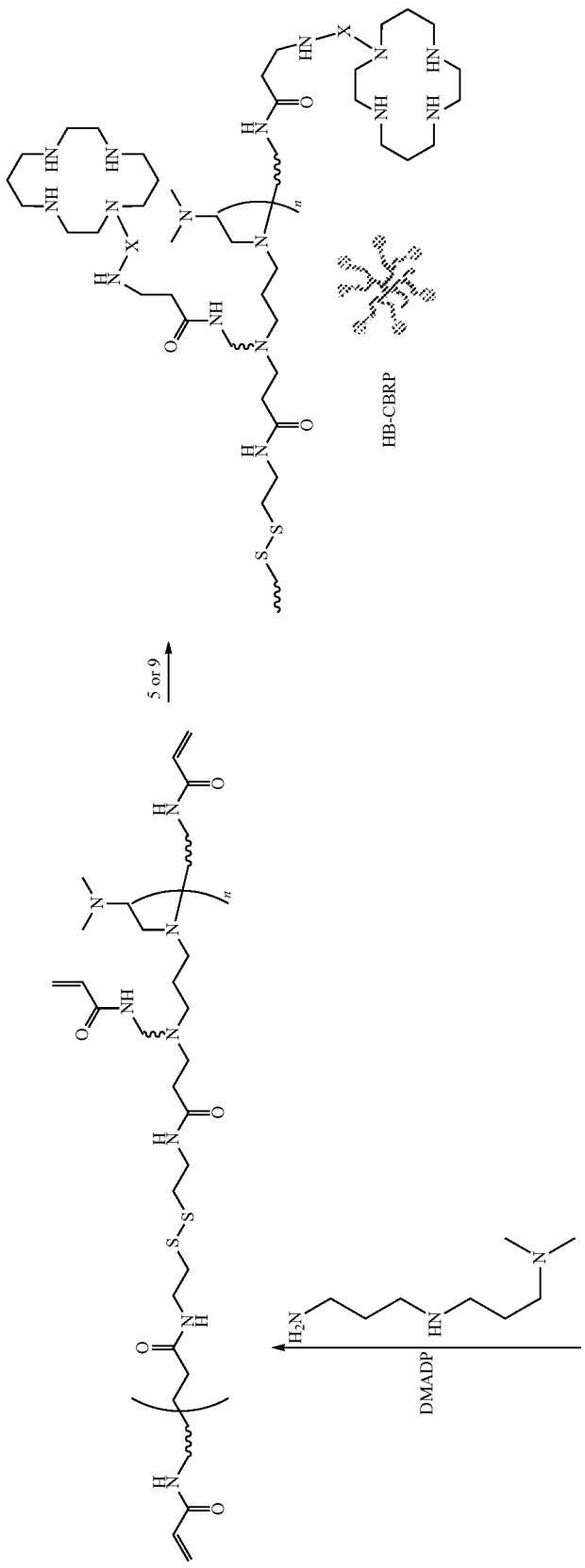
Scheme 4. Synthesis of CBRP with different architecture: hyperbranched (HB-CBRP), linear terminus-functionalized (LT-CBRP), and linear side-chain functionalized (LSC-CBRP). (only monocyclam-based CBRP are shown for simplicity)

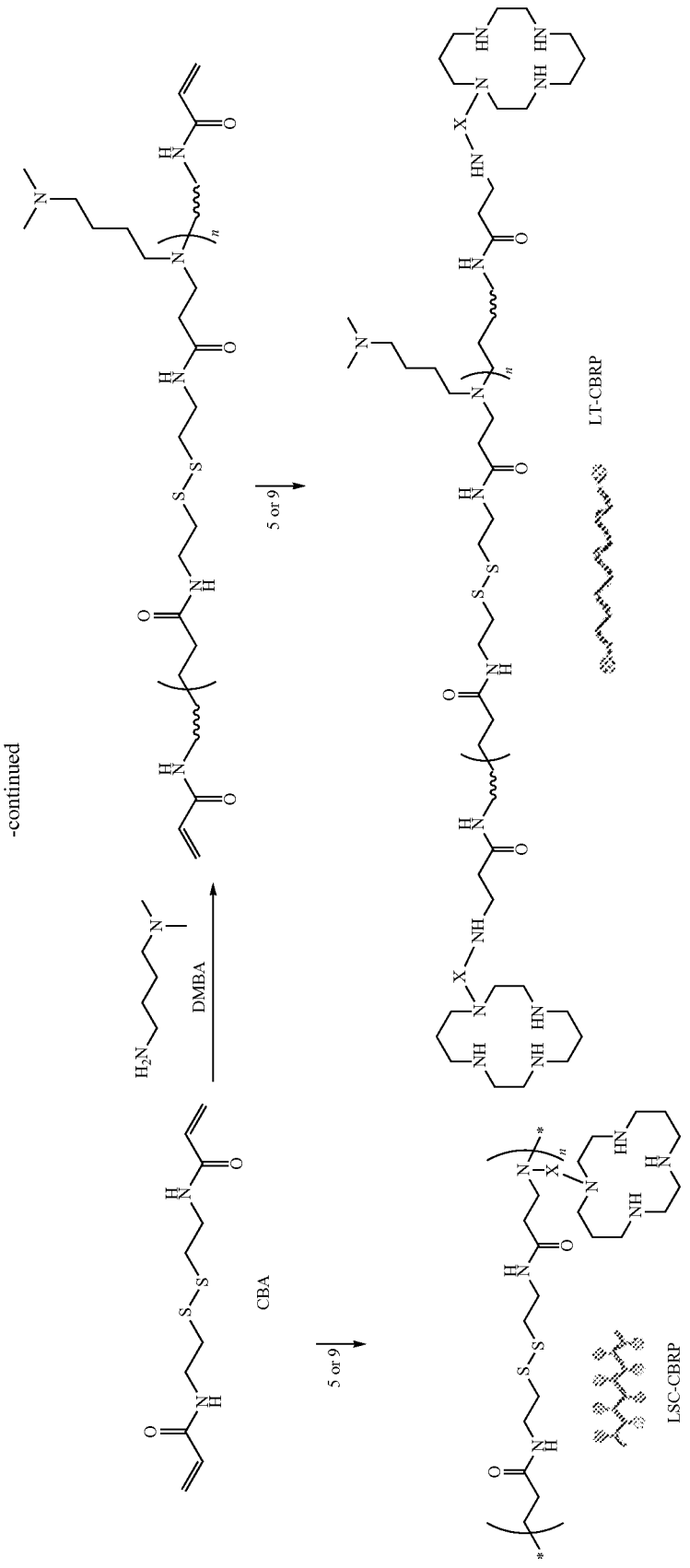

Nucleic Acid Delivery

Synthetic delivery vectors based on self-assembly of nucleic acids and polycations (polyplexes) continue to gain strength as viable alternatives to viral vectors. Significant effort has been devoted to the synthesis of safe and efficient biodegradable polycations. The polymers of the present invention are bioreducible polycations (BRPs) having the benefits of reduced toxicity compared to polycations and better spatial control of disassembly compared to hydrolytically degradable polycations. Improved spatial control of polyplex disassembly and release of DNA that is localized predominantly to the cytoplasm and nucleus have been shown to enhance transfection of several types of nucleic acids (plasmid DNA, mRNA, siRNA) in a number of cancer cell lines. Bioreducible polycations are degraded selectively in the reducing intracellular space (Christensen et al., Bioconjugate Chem, (2006) 17: 1233-1240, Zhang et al., J Controlled Rel, (2010) 143: 359-366). The degradation is mediated by thiol/disulfide exchange reactions with small redox molecules like GSH; possibly with the help of redox enzymes (Biaglow et al., Anal Biochem, (2000) 281: 77-86). GSH is the most abundant intracellular thiol present in mM concentrations inside the cell but only in µM concentrations in the blood plasma (Jones et al., Clin Chim Acta, (1998) 275: 175-84). The majority of GSH is usually found in the cytoplasm (1-11 mM), which is also the principal site of GSH biosynthesis. The most reducing environment is usually found within the nucleus, where it is required for DNA synthesis and repair and to maintain a number of transcription factors in reduced state. Metastatic cancer cells have been shown to have significantly elevated levels of GSH. BRPs are thus particularly promising for nucleic acid delivery to metastatic cancers because significantly elevated levels of GSH are often associated with high metastatic potential of cells.

CXCR4 is a highly conserved transmembrane G-protein-coupled receptor that binds exclusively its ligand CXCL12. It has been shown that common metastatic sites for prostate and breast cancers have high levels of CXCL12 and that metastatic cancer cells overexpress CXCR4 (Muller et al., Nature, (2001) 410: 50-6, Taichman et al., Cancer Res, (2002) 62: 1832-7, Chinni et al., Prostate, (2006) 66: 32-48, Rhodes et al., Cancer Res, (2011) 71: 603-613). CXCR4 expression increases during progression of prostate cancer (PC), and localized prostate carcinoma and bone metastasis tissue express significantly higher levels than benign prostate tissue (Sun et al., J Cell Biochem, (2003) 89: 462-73, Mochizuki et al., Biochem Biophys Res Commun, (2004) 320: 656-63). CXCR4 expression in PC is associated with poor survival (Akashi et al., Cancer Sci, (2008) 99: 539-42) and aggressive types of cancer (Wallace et al., Cancer Res, (2008) 68: 927-36). The chemokine CXCL12 is also overexpressed in PC metastatic tissue compared to normal tissue (Sun et al., supra). At the tumor cellular level, osteoblasts, stromal cells and endothelial cells all express CXCL12 (Taichmann et al., supra, Chinni et al., supra), and contribute to bone metastasis of PC cells. The CXCL12/CXCR4 binding has been shown to play an important role in PC cell proliferation, migration and invasion. In addition to prostate cancer, CXCR4 plays a role in metastasis of various tumor types, including breast cancer.

Cyclams are known to bind to CXCR4 and act as antagonists thereof. While not being bound to a particular theory, it is believed that the multivalent nature of cyclam-based BRPs (CBRPs) results in increased residence time of binding with the CXCR4, which in turn results in enhanced anti-CXCR4 activity. Furthermore, since all CBRPs of the present invention are synthesized to provide polycations with biodegradability in the intracellular reducing environment, they find use not only in reducing or inhibiting metastasis but in increasing the efficiency of transfection of DNA into cells.

Polyplexes are nucleic acids condensed with polycations, which can be used to transfect the nucleic acids into cells. CBRPs of the present invention are particularly useful for forming polyplexes. A vast majority of published reports confirm that polyplexes must be formulated with excess polycations in order to achieve efficient transfection. One of the advantages of using the CBRPs of the present invention to form polyplexes is that the polycation excess provided by CBRPs also has its own pharmacologic function, namely antagonism of CXCR4.

Ability to condense DNA is a prerequisite for successful polyplex gene delivery. FIG. 1 schematically represents this process. While not being bound to a particular theory, it is believed that the accessibility of amines in CBRPs of the present invention allows for efficient interaction with nucleic acids, resulting in their ability to condense DNA and allow for efficient transfection. By way of example, complexes based on cyclam or low molecular weight drug AMD3100 and nucleic acids mediated only background levels of transfection, which was reflective of their poor DNA condensing ability.

Polyethylene glycol (PEG) has been shown to improve colloidal stability of CBRP polyplexes and to reduce non-specific interactions that will enable selective targeting to PC (Pun et al., Bioconjugate Chem, (2002) 13: 630-639). Accordingly, PEG can be attached to CBRPs as a linking moiety between CBRP and a cyclic RGD peptide. For example, substituting the content of CBRP with at least about 5%-30% PEG-BRP and preferably with about 20% of PEG-BRP in the formulation is effective to decrease the rate of aggregation of the polyplexes. The use of PEG also shields the positive surface charge and allows specific targeting of polyplexes when equipped with appropriate targeting ligand, such as a cyclic RGD peptide. While not being bound to a particular theory, it is believed that PEG shielding prevents binding of polyplexes to CXCR4 and that only free polycations (i.e., not complexed with DNA) will be available for CXCR4 binding and inhibition.

The selection of cRGD as the targeting ligand for performing transfections is particularly advantageous as CXCL12 has been shown to stimulate an increase in the expression of activated $\alpha_v\beta_3$ integrin receptors in metastatic prostate cells C4-2B and PC3 (but not in LNCaP, the non-metastatic cell line from which C4-2B is derived) (Sun et al., The Prostate, (2007) 67: 61-73). Integrins are receptors that mediate attachment between a cell and the tissues surrounding it, which may be other cells or the extracellullar matrix (ECM). There are many types of integrins, and many cells have multiple types on their surface. All five αV integrins, two β1 integrins (α5, α8) and αIIbβ3 share the ability to recognize ligands containing an RGD tripeptide active site. The RGD-binding integrins are among the most promiscuous in the family, with β3 integrins in particular binding to a large number of extracellular matrix and soluble vascular ligands. Accordingly, the use of RGD peptides allows for transfection of polyplexes described herein into numerous types of cells, including breast cancer cells, prostate cancer cells, endothelial cells, etc.

When the carriers (including polymers or lipids) of the invention comprise a cRGD, the cyclic RGD peptide can be selected from the group consisting of cyclo(Arg-Gly-Asp-D-Phe-Cys), cyclo(Arg-Gly-Asp-D-Phe-Lys), H-Glu[cyclo (Arg-Gly-Asp-D-Phe-Lys)]$_2$, DOTA-Glu-[cyclo(Arg-Gly-Asp-D-Phe-Lys)]$_2$, H-Arg-Gly-Asp-Ser-Lys-OH, cyclo(Arg-Gly-Asp-D-Tyr-Lys), or a combination thereof. Preferably, the cyclic RGD peptide is cyclo(Arg-Gly-Asp-D-Phe-Cys).

Another advantage of the present invention is that it allows for the use of a wide variety of nucleic acids to be condensed with CBRPs of the present invention. Examples include plasmid DNA, shRNA, siRNA, microRNA, mRNA, and antisense oligonucleotides. Also, the nucleic acids can be plasmid DNA sequences. The nucleic acids can also be double-stranded (ds) RNA sequences involved in RNA interference, such as shRNA, siRNA and microRNA. The amount of DNA used in polyplexes is variable, and is determined by the content of CBRP. Preferably, the molar ratio between the protonizable amines of CBRP and the DNA phosphate groups is at least 0.9:1.

For the polymers of the invention, the cRGD-PEG-CBRP can have the following structure:

anced saline solutions such as Hank's or Earle's balanced salt solutions), 0.4% saline, 0.3% glycine, hyaluronic acid and the like.

The pharmaceutical composition of the present invention can be administered orally, nasally, parenterally, intrasystemically, intraperitoneally, topically (as by drops or transdermal patch), bucally, sublingually or as an oral or nasal spray, or as a pulmonary inhalation.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and non-aqueous excipients, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper

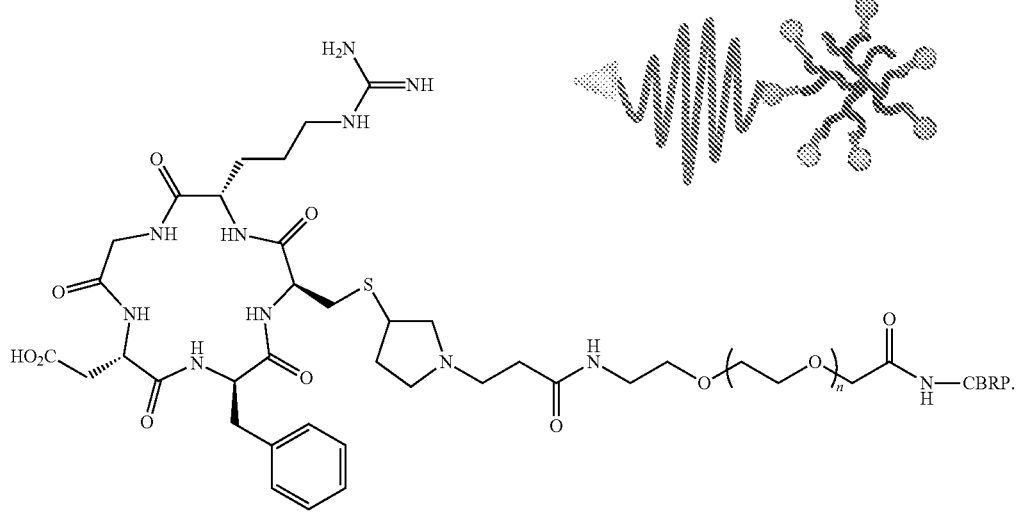

Uses

The carriers (including polymers and lipids) of the present invention can be used for a number of therapeutic applications. For such purposes, they can be formulated as pharmaceutical compositions with a pharmaceutically acceptable excipient.

Pharmaceutical compositions of the present invention are characterized as being at least sterile and pyrogen-free. Methods for preparing pharmaceutical compositions of the invention are within the skill in the art, for example as described in Remington's Pharmaceutical Science, 17th ed., Mack Publishing Company, Easton, Pa., (1985).

The pharmaceutical compositions of the present invention can comprise any of the bioreducible polycation polymers described herein coupled to a CXCR4 inhibiting moiety, wherein a CBRP can also include a cyclic RGD peptide, an optional PEG linker, and can also be condensed with nucleic acids to forma polyplex. The various combinations of these polymers are described in the foregoing sections.

The present pharmaceutical formulations can comprise the polymers, lipids, or combinations thereof disclosed herein.

Preferred physiologically acceptable excipients are water, buffered water, saline solutions (e.g., normal saline or balfluidity can be maintained, for example, by the use of coating materials such as lecithin or PEG, by the maintenance of the required particle size in the case of dispersions, and by the use of surfactants.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

In some cases, to prolong the effect of the pharmaceutical compositions, it is desirable to slow the absorption from subcutaneous or intramuscular injection. This can be accomplished by the use of a liquid suspension of crystalline or amorphous material with poor water solubility. Alternatively, delayed absorption of a parenterally administered pharmaceutical composition form is accomplished by dissolving or suspending the composition in an oil vehicle. Prolonged absorption of the injectable pharmaceutical form can be brought about by the inclusion of agents which delay absorption such as aluminum monostearate and gelatin.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The pharmaceutical compositions of the present invention can also be in a hydrogel, in a micro-encapsulated form, and the like, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof. Alternatively, the composition can be pressurized and contain a compressed gas, such as nitrogen or a liquefied gas propellant. The liquefied propellant medium and indeed the total composition are preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example calcium chloride, calcium ascorbate, calcium gluconate or calcium lactate).

One of ordinary skill in the art will appreciate that effective amounts of the agents of the invention can be determined empirically. It will be understood that, when administered to a human patient, the total daily usage of the agents or composition of the present invention will be decided by the attending physician within the scope of sound medical judgment. The specific therapeutically effective dose level for any particular patient will depend upon a variety of factors: the type and degree of the cellular or physiological response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

One skilled in the art can also readily determine an appropriate dosage regimen for administering the pharmaceutical compositions of the invention to a given subject. For example, they can be administered to the subject once, such as by a single injection or deposition. Alternatively, they can be administered to a subject multiple times daily or weekly, and for prolonged periods of time, if required.

The pharmaceutical compositions of the present invention find use in many different therapeutic applications, such as treatment of breast cancer and prostate cancer. The basis for the therapeutic applications lies in the inventors' discovery that polymers of the present invention once containing a cyclam compound, which acts as a CXCR4 inhibiting moiety, and to a cyclic RGD or another targeting ligand can form complexes with nucleic acids, and allow for efficient transfections of these complexes into cells. While not being bound to a particular theory, CXCR4 antagonism is thought to result in inhibition of cell invasion and metastatic spread of cancer cells. The additional benefit of using cyclam-based bioreducible polycations (CBRPs) is that they provide excess polycations, which have been show to increase the efficiency of transfections. Furthermore, RGD peptides bind to $\alpha_v\beta_3$ integrin receptors expressed on breast and prostate cancer cells, allowing for the complexes to be endocytosed. CBRPs allow for nucleic acids to be released in the cytoplasm or nucleus. Any nucleic acids can be used; however, nucleic acids capable of RNA interference (RNAi) such as microRNAs, siRNAs and shRNAs find particular uses. These short RNA molecules can bind to complementary mRNA transcripts in the cell, and prevent translation of proteins encoded by such mRNAs.

The process of RNAi begins by the presence of a long dsRNA in a cell, wherein the dsRNA comprises a sense RNA having a sequence homologous to the target gene mRNA and antisense RNA having a sequence complementary to the sense RNA. The presence of dsRNA stimulates the activity of a ribonuclease III enzyme referred to as Dicer. Dicer is involved in the processing of the dsRNA into short pieces of dsRNA known as short interfering RNAs (siRNAs) (Berstein et al., 2001, Nature, 409, 363). Short interfering RNAs derived from Dicer activity are typically about 21 to about 23 nucleotides in length and comprise about 19 base pair duplexes (Elbashir et al., 2001, Genes Dev., 15, 188). siRNAs in turn stimulate the RNA-induced silencing complex (RISC) by incorporating one strand of siRNA into the RISC and directing the degradation of the homologous mRNA target.

In research laboratories, two types of siRNA have been widely used to suppress exogenous as well as endogenous gene expression: synthetic siRNA and vector-based siRNA (i.e. in vivo transcribed siRNA). The vector based siRNA is usually generated through short hairpin RNA (shRNA). In this system, RNA polymerase III promoters, such as H1 promoter and U6 promoter are used to drive transcription of shRNA. The shRNA transcript consists of a 19- to 29-bp RNA stem, with the two strands joined by a tightly structured loop. shRNA is processed in the cell into siRNA through the action of the Dicer family of enzymes. Thus, the transcribed products mimic the synthetic siRNA duplexes and are as effective as the synthetic siRNA for suppressing their corresponding genes. In addition to the above-mentioned nucleic acids, antisense oligonucleotides can also be delivered to the cells using RGD-linked CBRPs as described herein.

Accordingly, the present invention provides a method for treating breast cancer in a patient by administering to the patient a therapeutically effective amount of a pharmaceutical composition comprising a bioreducible polycation polymer of the present invention, wherein the CXCR4 inhibiting moiety is a cyclam compound, wherein the polymer is linked to a cyclic RGD peptide, and further comprises a shRNA, siRNA or microRNA directed against survivin RNA.

Survivin, also called baculoviral inhibitor of apoptosis repeat-containing 5 or BIRC5, is a protein that, in humans, is encoded by the BIRC5 gene (Alfieri D C, J. Biol. Chem. 269 (5): 3139-42, February 1994). Survivin is a member of the inhibitor of apoptosis (IAP) family. The survivin protein functions to inhibit caspase activation, thereby leading to negative regulation of apoptosis or programmed cell death. This has been shown by disruption of survivin induction pathways leading to increase in apoptosis and decrease in tumor growth. The survivin protein is expressed highly in most human tumors and fetal tissue, but is completely absent in terminally differentiated cells (Sah et al., Cancer Lett. 244 (2): 164-71, December 2006). This fact therefore makes survivin an ideal target for breast and prostate cancer therapy as cancer cells are targeted while normal cells are not affected by survivin inhibition.

The present invention provides also provides a method for treating breast cancer in a patient by administering to the patient a therapeutically effective amount of a pharmaceutical composition comprising a polymer of the present invention, wherein the CXCR4 inhibiting moiety is a cyclam compound, wherein the polymer is linked to a cyclic RGD peptide, and which further comprises a shRNA, siRNA or microRNA directed against Bcl-2 RNA.

Bcl-2 protein is associated with membranes and membrane activity. Bcl-2 derives its name from B-cell lymphoma 2, as it is the second member of a range of proteins initially described in chromosomal translocations involving chromosomes 14 and 18 in follicular lymphomas. The Bcl-2 protein is a part of a complex system of signaling that controls apoptosis. Apoptosis (cell death) may be induced by a variety of signals including irreparable DNA damage. This form of cellular suicide prevents the expansion of damaged cells. Bcl-2 works to prevent apoptosis. Therefore, its overexpression can prevent apoptosis in cells that are damaged. This can lead to the continued division of the mutated cells lines and eventually cancer. Bcl-2 is localized to the luminal cells of the normal breast, which are considered to be the origin of malignant breast disease.

The present invention can also provide a method for treating breast cancer in a patient by administering to the patient a therapeutically effective amount of a pharmaceutical composition comprising a polymer of the present invention, wherein the CXCR4 inhibiting moiety is a cyclam compound, wherein the polymer is linked to a cyclic RGD peptide, and which further comprises a shRNA, siRNA or microRNA directed against Her2 RNA.

HER2/neu (also known as ErbB-2) stands for "Human Epidermal growth factor Receptor 2" and is a protein giving higher aggressiveness in breast cancers. It is a member of the ErbB protein family, more commonly known as the epidermal growth factor receptor family. HER2/neu has also been designated as CD340 (cluster of differentiation 340) and p185. It is encoded by the ERBB2 gene. HER2 is a cell membrane surface-bound receptor tyrosine kinase and is normally involved in the signal transduction pathways leading to cell growth and differentiation. It is encoded within the genome by HER2/neu, a known proto-oncogene. Approximately 30% of breast cancers have an amplification of the HER2/neu gene or overexpression of its protein product. Overexpression of this receptor in breast cancer is associated with increased disease recurrence and worse prognosis. Accordingly, inhibiting HER2 expression in breast cancer is of great value for treatment success.

The present invention can further provide a method for treating prostate cancer (PC) in a male patient by administering to the male patient a therapeutically effective amount of a pharmaceutical composition comprising a polymer of the present invention, wherein the CXCR4 inhibiting moiety is a cyclam compound, wherein the polymer is linked to a cyclic RGD peptide, and which further comprises a shRNA, siRNA or microRNA directed against survivin RNA.

The present invention can additionally provide a method for treating prostate cancer in a male patient by administering to the patient a therapeutically effective amount of a pharmaceutical composition comprising a polymer of the present invention, wherein the polymer is linked to a cyclic RGD peptide, and which further comprises a shRNA, siRNA or microRNA directed against Bcl-2 RNA. Preferably, the CXCR4 inhibiting moiety is a cyclam compound.

The present invention is also directed to a method for treating prostate cancer in a male patient by administering to the patient a therapeutically effective amount of a pharmaceutical composition comprising a polymer of the present invention, wherein the polymer is linked to a cyclic RGD peptide, and which further comprising a shRNA, siRNA or microRNA directed against Her-2 RNA. Preferably, the CXCR4 inhibiting moiety is a cyclam compound. In addition to breast cancer, HER-2 has also been indicated in other cancers including prostate cancer. While not being bound to a theory, when prostate cancers progress from an androgen-dependent to an androgen-independent phenotype, epidermal growth factor pathways are frequently activated, potentially resulting in Her-2 activation. Prostate cancer, like most hormone dependent cancers becomes refractory to treatment after one to three years, and resumes growth despite hormone therapy. Previously considered "hormone-refractory prostate cancer" or "androgen-independent prostate cancer", the term castration-resistant has replaced "hormone refractory" because while it is no longer responsive to castration treatment (reduction of available androgen/testosterone/DHT by chemical or surgical means), prostate cancer still show reliance upon hormones for androgen receptor activation. Thus, inhibiting HER2 can be especially beneficial for use in castration-resistant prostate cancer.

Also, a therapeutically effective amount of a pharmaceutical composition comprising a polymer of the present invention and which further comprises a shRNA, siRNA or microRNA directed against akt2, PARP or STAT3 can be administered to a patient to treat breast cancer or to a male patient to treat prostate cancer.

The akt2 gene is a putative oncogene that plays an important role in balancing cell survival and apoptosis. Studies have shown that Akt2 overexpression leads to increased metastasis. Akt is the direct downstream effector of PI3K signaling pathway involved in CXCR4-mediated tumor progression and metastasis (Vlahakis et al., "G protein-coupled chemokine receptors induce both survival and apoptotic signaling pathways." J Immunol, 2002, 169(10): p. 5546-54). Akt activation by SDF-1 is required for CXCR4-mediated chemotaxis of breast cancer cells (Zhao, M., B. M. Mueller, R. G. DiScipio, and I. U. Schraufstatter, "Akt plays an important role in breast cancer cell chemotaxis to CXCL12." Breast cancer research and treatment, 2008, 110(2): p. 211-22). CXCR4/SDF-1 axis also promotes VEGF-mediated tumor angiogenesis through Akt signaling pathway (Liang, Z., J. Brooks, M. Willard, K. Liang, Y. Yoon, S. Kang, and H. Shim, "CXCR4/CXCL12 axis promotes VEGF-mediated tumor angiogenesis through Akt signaling pathway." Biochemical and biophysical research communications, 2007, 359(3): p. 716-22). Reduction of Akt expression by siRNA inhibits invasiveness of multiple breast cancer cell lines (Wang, J., W. Wan, R. Sun, Y. Liu, X. Sun, D. Ma, and N. Zhang, "Reduction of Akt2 expression inhibits chemotaxis signal transduction in human breast cancer cells." Cellular signaling, 2008, 20(6): p. 1025-34). Poly(ADP-ribose) polymerase (PARP) is a protein involved in DNA repair, and its overexpression was observed in breast cancer (Goncalves et al., "Poly(ADP-ribose) polymerase-1 mRNA expression in human breast cancer: a meta-analysis." Breast Cancer Res Treat, 2011, 127(1): p. 273-81). Inhibition of PARP has shown promising efficacy for breast cancer treatment (Fogelman et al., "Evidence for the Efficacy of Iniparib, a PARP-1 Inhibitor, in BRCA2-associated Pancreatic Cancer." Anticancer Res, 2011, 31(4): p. 1417-20; Perkins et al., "Novel inhibitors of poly(ADP-ribose) polymerase/PARP1 and PARP2 identified using a cell-based screen in yeast." Cancer Res, 2001, 61(10): p. 4175-83; Yuan et al., "Novel targeted therapeutics: inhibitors of MDM2, ALK and PARP." J Hematol Oncol, 2011, 4(1): p. 16; Goldberg et al., "Nanoparticle-mediated delivery of siRNA targeting Parp1 extends survival of mice bearing tumors derived from Brca1-deficient ovarian cancer cells." Proceedings of the National Academy of Sciences, 2011, 108(2): p. 745-750). Signal transducer and activator of transcription 3 (STAT3) is a transcription factor that is involved in a variety of physiological processes. Constitutive activation of STAT3 is associated with many human cancers, including breast cancer (Buettner et al., "Activated signal transducers and activators of transcription 3 signaling induces CD46 expression and protects human cancer cells from complement-dependent cytotoxicity." Mol Cancer Res, 2007, 5(8): p. 823-32; Cabo et al., "STAT proteins: from normal control of cellular events to tumorigenesis." J Cell Physiol, 2003, 197(2): p. 157-68; Klampfer, L., "The role of signal transducers and activators of transcription in colon cancer." Front Biosci, 2008, 13: p. 2888-99; Nikitakis et al., "Targeting the STAT pathway in head and neck cancer: recent advances and future prospects." Curr Cancer Drug Targets, 2004, 4(8): p. 637-51)). STAT3 is a novel target in cancer therapy (Turkson, J., "STAT proteins as novel targets for cancer drug discovery." Expert Opin Ther Targets, 2004, 8(5): p. 409-22), and its siRNA inhibition has shown promising effects on suppression of cell growth and induction of apoptosis (Gao et al., "Inhibition of STAT3 expression by siRNA suppresses growth and induces apoptosis in laryngeal cancer cells." Acta Pharmacologica Sinica, 2005, 26(3): p. 377-383; Lee et al., "RNA interference targeting Stat3 inhibits growth and induces apoptosis of human prostate cancer cells." Prostate, 2004, 60(4): p. 303-309; Klosek et al, "Stat3 as a molecular target in RNA interference-based treatment of oral squamous cell carcinoma." Oncology Reports, 2008, 20(4): p. 873-878).

Further, the present invention provides a method for treating lung cancer in a patient by administering to the patient a therapeutically effective amount of a pharmaceutical composition comprising a polymer of the present invention, wherein the CXCR4 inhibiting moiety is a cyclam compound, wherein the polymer is linked to a cyclic RGD peptide, and which further comprises a shRNA, siRNA or microRNA directed against any of the RNAs selected from akt2, survivin, PARP, STAT3 and EGFR (epidermal growth factor receptor). The lung cancer can be either a small cell lung cancer (SCLC) or non-small cell lung cancer (NSCLC).

Still further, the present invention is directed to a method for treating inflammatory bowel disease (IBD) in a patient by administering to the patient a therapeutically effective amount of a pharmaceutical composition comprising a polymer of the present invention and further comprises a shRNA, siRNA or microRNA directed against TNF-alpha RNA. Preferably, the CXCR4 inhibiting moiety is a cyclam compound. IBD is a bowel disorder characterized by chronic abdominal pain, discomfort, bloating, and alteration of bowel habits in the absence of any detectable organic cause. There is no specific laboratory or imaging test that can be performed to diagnose IBD. Diagnosis of IBD involves excluding conditions that produce IBD-like symptoms, and then following a procedure to categorize the patient's symptoms. Ruling out parasitic infections, lactose intolerance, small intestinal bacterial overgrowth and celiac disease is recommended for all patients before a diagnosis of irritable bowel syndrome is made. While the cause of IBD is unknown, it has been shown that proinflammatory cytokines, such as TNF-alpha are higher in patient with IBD than in control subjects (Liebregts et al., Gastroenterology 2007 March; 132(3):913-20). Accordingly, while not being bound to a theory, inhibiting TNF-alpha could result in improvement or cure of IBD.

Additionally, the present invention is directed to a method for inhibiting or reducing metastasis, the method comprising administering to a patient a polymer linked to a CXCR4 inhibiting moiety; preferably, the CXCR4 inhibiting moiety is a cyclam compound. As noted in the foregoing sections, CXCR4 is a highly conserved transmembrane G-protein-coupled receptor that binds exclusively its ligand CXCL12. It has also been shown that common metastatic sites for prostate and breast cancers have high levels of CXCL12 and that metastatic cancer cells overexpress CXCR4. Since CXCR4 plays a role in metastasis in a large number of different tumor types, cyclam-based BRPs of the present invention can be used to inhibit or reduce metastasis, regardless of the cancer cell where it originated. For purposes of inhibiting or reducing metastasis, CBRPs of the present invention can be formulated as pharmaceutical compositions.

In all of the above methods, a patient is preferably a human. The pharmaceutical compositions used in the above methods can be administered parenterally. Alternatively, the pharmaceutical compositions can be administered enterally. It may be desirable to administer pharmaceutical compositions used for prostate cancer, breast cancer and for reducing or inhibiting metastasis parenterally whereas it may be desirable to administer compositions used for treating IBD enterally. As mentioned in the previous sections, a PEG linking moiety can be used between the cyclic RGD peptide and the BRP polymer for parenteral administrations.

The invention is also directed to a method for positron emission tomography (PET) or magnetic resonance imaging using the polymers that further comprise a metal ion complexed with the cyclam monomer or compound. PET is a nuclear medicine imaging technique that produces a three-dimensional image or picture of functional processes in the body. The system detects pairs of gamma rays emitted indirectly by a positron-emitting radionuclide (tracer), which is introduced into the body on a biologically active molecule. Three-dimensional images of tracer concentration within the body are then constructed by computer analysis. In modern scanners, three dimensional imaging is often accomplished with the aid of a CT X-ray scan performed on the patient during the same session, in the same machine.

The radioisotopes that can be used for PET imaging are $^{68}$Ga, $^{64}$Cu, $^{48}$V, $^{71}$As, $^{72}$As, $^{76}$Br, or other polyvalent, cationic radiometals that decay by positron emission.

General Methods

Molecular biological techniques, biochemical techniques, and microorganism techniques as used herein are well known in the art and commonly used, and are described in, for example, Sambrook J. et al. (1989), Molecular Cloning: A Laboratory Manual, Cold Spring Harbor and its 3rd Ed. (2001); Ausubel, F. M. (1987), Current Protocols in Molecular Biology, Greene Pub. Associates and Wiley-interscience; Ausubel, F. M. (1989), Short Protocols in Molecular Biology: A Compendium of Methods from Current Protocols in Molecular Biology, Greene Pub. Associates and Wiley-interscience; Innis, M. A. (1990), PCR Protocols: A Guide to Methods and Applications, Academic Press; Ausubel, F. M. (1992), Short Protocols in Molecular Biology: A Compendium of Methods from Current Protocols in Molecular Biology, Greene Pub. Associates; Ausubel, F. M. (1995), Short Protocols in Molecular Biology: A Compendium of Methods from Current Protocols in Molecular Biology, Greene Pub. Associates; Innis, M. A. et al. (1995), PCR Strategies, Academic Press; Ausubel, F. M. (1999), Short Protocols in Molecular Biology: A Compendium of Methods from Current Protocols in Molecular Biology, Wiley, and annual updates; Sninsky, J. J. et al. (1999), PCR Applications: Protocols for Functional Genomics, Academic Press; Special issue, and the like. Relevant portions (or possibly the entirety) of each of these publications are herein incorporated by reference.

Any technique may be used herein for introduction of a nucleic acid molecule into cells, including, for example, transformation, transduction, transfection, and the like. Such a nucleic acid molecule introduction technique is well known in the art and commonly used, and is described in, for example, Ausubel F. A. et al., editors, (1988), Current Protocols in Molecular Biology, Wiley, New York, N.Y.; Sambrook J. et al. (1987) Molecular Cloning: A Laboratory Manual, 2nd Ed. and its 3rd Ed., Cold Spring Harbor Laboratory Press, Cold Spring Harbor, N.Y.; Special issue, and the like. Gene introduction can be confirmed by method as described herein, such as Northern blotting analysis and Western blotting analysis, or other well-known, common techniques.

DEFINITIONS AND ABBREVIATIONS

"Treatment" or "treating" refers to a therapeutic intervention that ameliorates a sign or symptom of a disease or pathological condition, such a sign or symptom of cancer. Treatment can also induce remission or cure of a condition.

The term "patient" includes any human or animal subject who is in need of treatment for an indication as claimed herein.

The phrase "therapeutically-effective" is intended to qualify the amount of each agent which will achieve the goal of improvement in disorder severity and the frequency of incidence over no treatment.

"RGD peptide" refers to an amino acid sequence Arginine-Glycine-Aspartic acid ("RGD" is the one-letter amino acid code, as is standardly expressed in the art).

"Small interfering RNA" (siRNA) refers to double-stranded RNA molecules from about 10 to about 30 nucleotides long that are named for their ability to specifically interfere with protein expression. The length of the siRNA molecule is based on the length of the antisense strand of the siRNA molecule.

A "shRNA" is an abbreviation for short hairpin RNA.

"Transfection" is the term used to describe the introduction of foreign material such as foreign DNA into eukaryotic cells. It is used interchangeably with "transformation" and "transduction" although the latter term, in its narrower scope refers to the process of introducing DNA into cells by viruses, which act as carriers. Thus, the cells that undergo transfection are referred to as "transfected," "transformed" or "transduced" cells.

A "CBRP" is a CXCR4 inhibiting bioreducible polymer and examples of those polymers are referred to herein as P(AMD-CBA), RPA, and the like.

Biodegradable, but not bioreducible polymers are known as NPA and examples of these polymers are P(AMD-HMBA), CopCX, and the like.

A "RHB" polymer is a control polymer that is a bioreducible polymer that does not comprise a CXCR4 inhibiting moiety.

Unless otherwise indicated, the alkyl groups described herein are preferably lower alkyl containing from one to eight carbon atoms in the principal chain and up to 20 carbon atoms. Alkyls may be substituted or unsubstituted and straight or branched chain. Examples of unsubstituted alkyls include methyl, ethyl, n-propyl, i-propyl, n-butyl, i-butyl, s-butyl, t-butyl, n-pentyl, i-pentyl, s-pentyl, t-pentyl, and the like. The term "substituted," as in "substituted alkyl," means that various heteroatoms such as oxygen, nitrogen, sulfur, phosphorus, and the like can be attached to the carbon atoms of the alkyl group either in the main chain or as pendant groups. For example, the substituted alkyl groups can have —C—X—C— fragments in the main chain wherein the X is a heteroatom. Further, the substituted alkyl groups can have at least one hydrogen atom bound to a carbon atom replaced with one or more substituent groups such as hydroxy, alkoxy, alkylthio, phosphino, amino, halo, silyl, nitro, esters, ketones, heterocyclics, aryl, and the like.

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The term "-ene" as used as a suffix as part of another group denotes a bivalent radical in which a hydrogen atom is removed from each of two terminal carbons of the group, or if the group is cyclic, from each of two different carbon atoms in the ring. For example, alkylene denotes a bivalent alkyl group such as methylene (—CH$_2$—) or ethylene (—CH$_2$CH$_2$—), and arylene denotes a bivalent aryl group such as o-phenylene, m-phenylene, or p-phenylene. For clarity, addition of the -ene suffix is not intended to alter the definition of the principal word other than denoting a bivalent radical. Thus, continuing the example above, alkylene denotes an optionally substituted linear saturated bivalent hydrocarbon radical.

The term "hydrocarbon" as used herein describes a compound or radical consisting exclusively of the elements carbon and hydrogen.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON(R$_A$)(R$_B$), wherein R$_A$ and R$_B$ are independently hydrogen, alkyl, or aryl), amino(—N(R$_A$)(R$_B$), wherein R$_A$ and R$_B$ are independently hydrogen, alkyl, or aryl), halo (fluoro, chloro, bromo, or iodo), silyl, nitro (—NO$_2$), an ether (—OR$_A$ wherein R$_A$ is alkyl or aryl), an ester (—OC(O)R$_A$ wherein R$_A$ is alkyl or aryl), keto (—C(O)R$_A$ wherein R$_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heteroaryl," as used herein alone or as part of another group, denotes an optionally substituted monovalent monocyclic or bicyclic aromatic radical of 5 to 10 ring atoms in protonated or unprotonated form, where one or more, preferably one, two, or three, ring atoms are heteroatoms independently selected from N, O, and S, and the remaining ring atoms are carbon. Exemplary heteroaryl moieties include benzofuranyl, benzo[d]thiazolyl, benzo[d]thiazolium, isoquinolinyl, isoquinolinium, quinolinyl, quinolinium, thiophenyl, imidazolyl, imidazolium, oxazolyl, oxazolium, furanyl, thiazolyl, thiazolium, pyridinyl, pyridinium, furyl, thienyl, pyridyl, pyrrolyl, pyrrolidinium, indolyl, indolinium, and the like.

The term "heterocyclo," as used herein alone or as part of another group, denotes a saturated or unsaturated monovalent monocyclic group of 4 to 8 ring atoms in protonated or unprotonated form, in which one or two ring atoms are heteroatom(s), independently selected from N, O, and S, and the remaining ring atoms are carbon atoms. Additionally, the heterocyclic ring may be fused to a phenyl or heteroaryl ring, provided that the entire heterocyclic ring is not completely aromatic. Exemplary heterocyclo groups include the heteroaryl groups described above, pyrrolidino, pyrrolidinium, piperidino, piperidinium, morpholino, morpholinium, piperazino, piperazinium, succinimide, and the like. In some cases, the heterocyclo can be a bivalent radical wherein the hydrogen is removed from each of two atoms in the heterocyclo group.

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis of Cyclam Monomer with Ethyleneoxide Linker

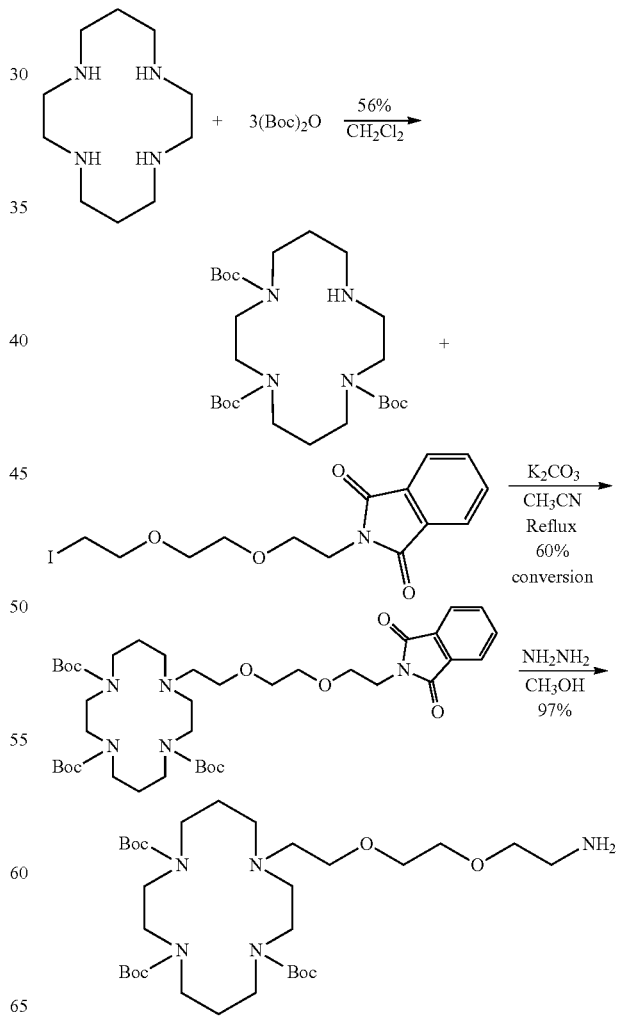

Tri Boc Cyclam.

A solution of t-butyl dicarbonate (Boc₂O) (2.96 g, 13.1 mmol) in 80 mL of methylene chloride (CH₂Cl₂) was added dropwise over a period of 2 hours to a solution of cyclam (0.88 g, 4.4 mmol) in CH₂Cl₂ at 0° C. The mixture was allowed to warm to room temperature and stirred overnight. The mixture was concentrated and purified by chromatography (ethyl acetate (AcOEt)→10:1 AcOEt:methanol (CH₃OH)) to give cyclam-Boc₄ (0.91 g, 35%) as a white set foam and cyclam-Boc₃ (1.22 g, 56%) as a light yellow set foam. Tri Boc cyclam: $^1$H NMR (CDCl₃) δ 1.46 (s, 27H), 1.65-1.76 (m, 2H), 2.00-1.80 (m, 2H), 2.62 (bt, J=5.6 Hz, 2H), 2.79 (t, J=4.8 Hz, 2H), 3.31 (t, J=6.4 Hz, 8H), 3.47-3.34 (m, 4H). (see Schickaneder, C.; Heinemann, F. W.; Alsfasser, R. "Copper II Complexes of the Tetraazamacrocyclic Tertiary Amide Ligand Alanyl-Cyclam," *Eur. J. Chem.* 2006, 2357-2363)

N-(2-(2-(Chloroethoxy)ethoxy)ethyl)phthalimide

A mixture of potassium phthalimide (3.00 g, 15.9 mmol) and 1,2-bis(2-chloroethoxy)ethane (25 mL, 30 g, 160 mmol) was heated at 130° C. overnight. The excess 1,2-bis(2-chloroethoxy)ethane was distilled under high vacuum to leave a yellow semi-solid. This was mixed with CH₂Cl₂ (50 mL) and the insoluble material removed by filtration. The filtrate was concentrated to give a yellow liquid and purified by chromatography (2:1 Hexanes:AcOEt) to give (4.40 g, 93%) as a colorless liquid. $^1$H NMR (CDCl₃) δ 3.55 (t, J=6.0 Hz, 2H), 3.68-3.61 (m, 4H), 3.69 (t, J=6.0 Hz, 2H), 3.76 (t, J=6.0 Hz, 2H), 3.92 (t, J=6.0 Hz, 2H), 7.73 (dd, J=5.2, 2.4 Hz, 2H), 7.86 (dd, J=5.2, 2.4 Hz, 2H). (see Lukyanenko, N. G.; Kirichenko, T. I.; Shcherbakov, S. V. "Synthesis of Lariat Diazacrown Ethers with Terminal Amino Groups in the Side Chains," *Chem. Heterocycl. Compd.* 2004, 40: 343-350.)

N-(2-(2-(Iodoethoxy)ethoxy)ethyl)phthalimide

A mixture of N-(2-(2-(chloroethoxy)ethoxy)ethyl)phthalimide (4.0 g, 13 mmol), NaI (4.6 g, 31 mmol) and acetonitrile (CH₃CN) (30 mL) was refluxed overnight. After cooling it was concentrated to give a brown orange semi solid that was mixed with CH₂Cl₂ (50 mL) and the insoluble material removed by filtration. The filtrate was washed with 5% sodium thiosulfate (Na₂S₂O₃) (10 mL) until all of the brown color disappeared. The layers were separated and the aqueous layer extracted with CH₂Cl₂. The combined CH₂Cl₂ layers were dried with anhydrous magnesium sulfate (MgSO₄) and concentrated to give a yellow liquid. This was purified by chromatography (2:1 Hexanes:AcOEt) to give (5.15 g, 100%) as a light orange liquid. $^1$H NMR (CDCl₃) δ 3.15 (t, J=6.4 Hz, 2H), 3.63-3.56 (m, 4H), 3.66 (t, J=6.8 Hz, 2H), 3.74 (t, J=6.0 Hz, 2H), 3.89 (t, J=5.6 Hz, 2H), 7.70 (dd, J=5.2, 2.4 Hz, 2H), 7.8 (dd, J=5.2, 2.4 Hz, 2H).

Tri Boc cyclam N-(2-(2-ethoxyethoxy)ethyl)phthalimide

A mixture of tri Boc cyclam (0.50 g, 1.0 mmol), N-(2-(2-(Iodoethoxy)ethoxy)ethyl)phthalimide (0.78 g, 2.0 mmol), anhydrous potassium carbonate (K₂CO₃) (0.34 g, 2.5 mmol) and CH₃CN (10 mL) was refluxed overnight. After cooling it was concentrated to give a light yellow semi solid that was mixed with hot AcOEt (25 mL) and the insoluble material removed by filtration. The filtrate was concentrated to give a yellow liquid and purified by chromatography (AcOEt→10:1 AcOEt:CH₃OH) to give (0.45 g, 98% based on 60% conversion) as a colorless liquid and (0.20 g) of unreacted tri Boc cyclam. $^1$H NMR (CDCl₃) δ 1.45 (s, 18H), 1.46 (s, 9H), 1.72-1.59 (m, 2H), 1.94-1.82 (m, 2H), 2.45-2.36 (m, 2H), 2.58 (t, J=6.4 Hz, 4H), 3.21-3.15 (m, 2H), 3.41-3.22 (m, 10H), 3.45 (t, J=6.4 Hz, 2H), 3.51 (t, J=4.8 Hz, 2H), 3.64-3.60 (m, 2H), 3.73 (t, J=6.0 Hz, 2H), 3.89 (t, J=6.0 Hz, 2H), 7.72 (dd, J=5.6, 2.4 Hz, 2H), 7.85 (dd, J=4.8, 2.4 Hz, 2H).

Tri Boc cyclam 2-(2-ethoxyethoxy)ethanamine

To a solution of triBoc cyclam phthalimide (0.45 g, 0.59 mmol) in CH₃OH (10 mL), hydrazine (NH₂NH₂) (0.19 mL, 0.19 g, 6.0 mmol) was added and stirred overnight. The mixture was concentrated to give a white solid that was mixed with hot CH₂Cl₂ (25 mL) and the insoluble material removed by filtration. The filtrate was concentrated to give a yellow liquid and purified by chromatography (10:1 CH₂Cl₂:CH₃OH+0.5% NH₃) to give (0.36 g, 97%) as a yellow set liquid. $^1$H NMR (CDCl₃) δ 1.46 (s, 27H), 1.72-1.60 (m, 2H), 1.94-1.82 (m, 2H), 2.53-2.41 (m, 2H), 2.72-2.53 (m, 4H), 3.12-3.02 (m, 2H), 3.25-3.16 (m, 2H), 3.45-3.25 (m, 10H), 3.55-3.50 (m, 2H), 3.60-3.55 (m, 2H), 3.65-3.60 (m, 2H), 3.70-3.65 (m, 2H), 5.11 (bs, 2H).

Example 2

Synthesis of P(AMD-CBA) (Also Referred to Herein as RPA)

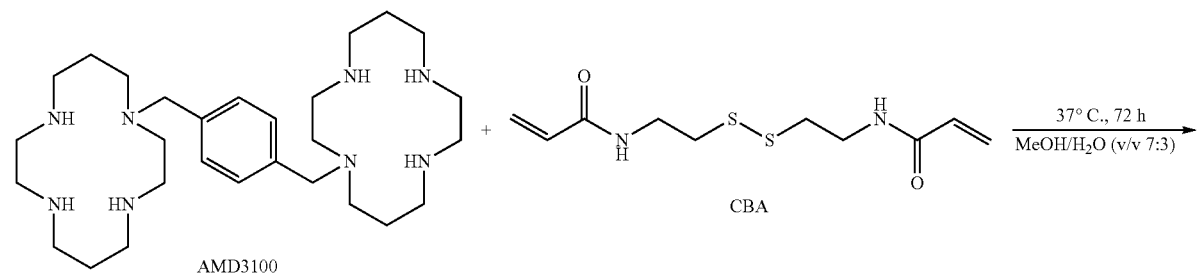

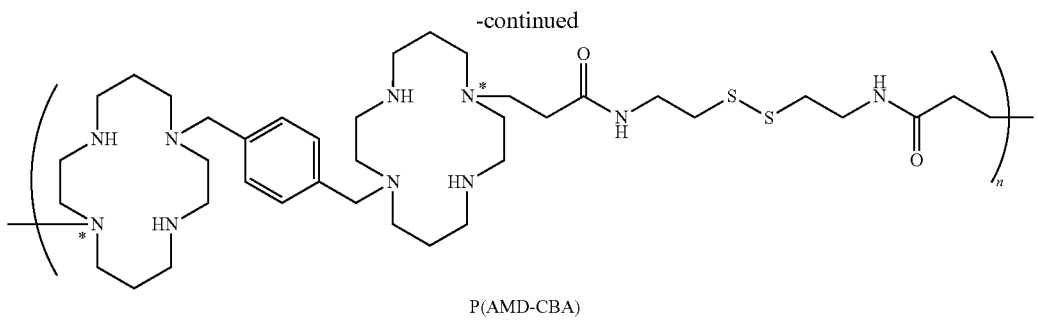

P(AMD-CBA)

\* could be any secondary amine and could have multiple attachments to the same ring
Synthetic route of P(AMD-CBA) *Exact location of the AMD3100 attachment could not be determined.
Any of the secondary amines of either of the rings are susceptible to modification.

P(AMD-CBA) was synthesized by Michael addition of 1,1'-[1,4-Phenylenebis(methylene)]bis[1,4,8,11-tetraazacyclotetradecane] (AMD3100) and N',N'-cystamine bisacrylamide (CBA) at molar ratio of 1:1. Calculated amounts of AMD3100 (200.8 mg, 0.4 mmol) and CBA (104 mg, 0.4 mmol) were weighed and dissolved in methanol/water mixture (4 mL, v/v 7:3) to make soluble RPA. Polymerization was allowed to proceed under nitrogen protection in the dark at 37° C. for 72 hours before gelation. Then, an additional 20 mg of AMD3100 was added to the reaction mixture to consume any residual acrylamide groups and the mixture was stirred for another 6 hours. The reaction mixture was added dropwise to an excess 1.25 M HCl in ethanol and the pH of the mixture was kept at about 3. The resulting precipitated HCL salt of the RPA was centrifuged and washed with ethanol twice to remove the extra acid. The products were then dried using a vacuum pump and redissolved in water. After dialysis against water for 2 days (MWCO 3,500), the polymers were freeze dried and ready to use.

Example 3

Characterization of P(AMD-CBA)

Figure 2:
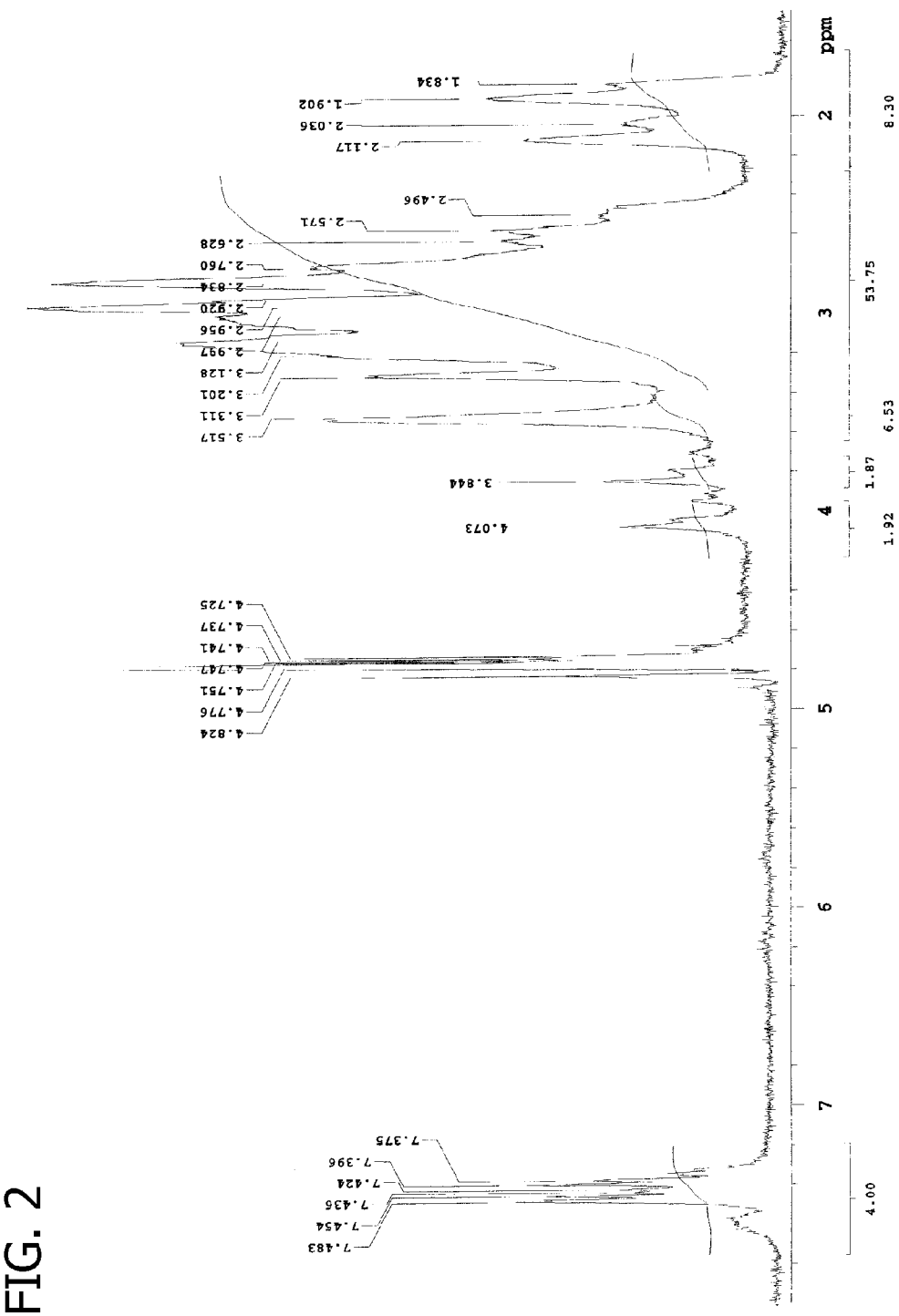
FIG. 2 is a $^1$H NMR of a polymer prepared from 1,1'-[1,4-Phenylenebis(methylene)]bis[1,4,8,11-tetraazacyclotetradecane] (AMD3100) and N,N'-Cystamine bisacrylamide (CBA).

The composition of the polymers was analyzed by $^1$H NMR. Molecular weight of the polymers was determined by Gel Permeation Chromatography (GPC) (Malvern Instruments). Sodium acetate (0.3 M, pH 5) was used as an eluent at flow rate of 0.3 mL/minute. Number average molecular weight ($M_n$) of P(AMD-CBA) was 12,553, Weight average ($M_w$) molecular weight of P(AMD-CBA) was 13,756, and PDI was 1.096. See FIG. 2.

Example 4

Figure 3:
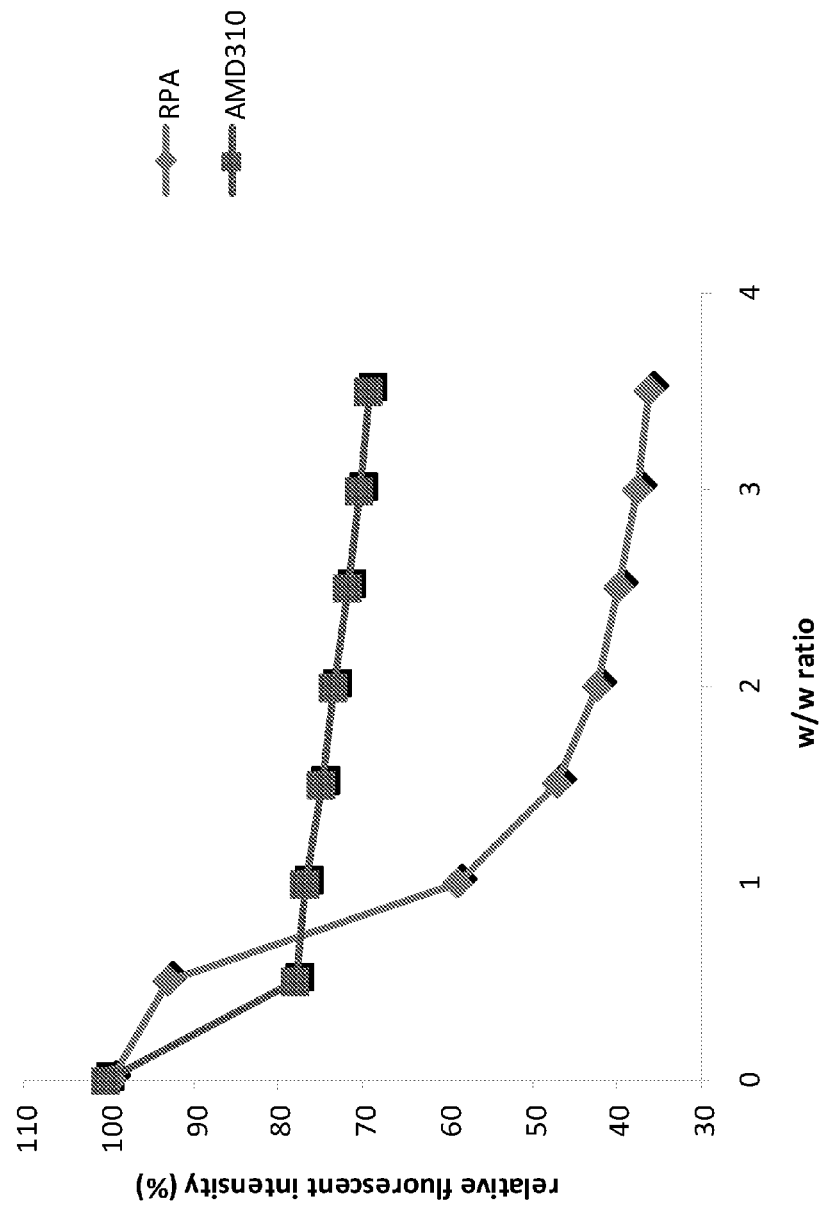
FIG. 3 is a graph of relative fluorescence intensity versus weight/weight ratio that shows pDNA condensation of a polymer prepared from 1,1'-[1,4-Phenylenebis(methylene)]bis[1,4,8,11-tetraazacyclotetradecane] (AMD3100) and N,N'-Cystamine bisacrylamide (CBA) (P(AMD-CBA or RPA) and AMD3100 by ethidium bromide exclusion assay.

Condensation of Plasmid DNA to Show that P(AMD-CBA) Forms Complexes with DNA The ability of P(AMD-CBA) to condense pDNA was determined by ethidium bromide exclusion (EtBr) assay by measuring the changes in EtBr/pDNA fluorescence. pDNA solution at a concentration of 20 μg/mL was mixed with EtBr (1 μg/mL) and fluorescence was measured and set to 100% using an excitation wavelength of 540 nm and an emission wavelength of 590 nm. Fluorescence readings were taken following a stepwise addition of the polycation solution, and the condensation curve for each polycation was constructed. See FIG. 3.

Example 5

Size and Zeta Potential of P(AMD-CBA) Complexes with Plasmid DNA (Polyplexes)

Luciferase plasmid DNA (gWiz-Luc pDNA, Aldevron) solution at a concentration 20 μg/mL was prepared in 10 mM HEPES buffer (pH 7.4). Polyplexes were formed by adding a predetermined volume of polymer to achieve the desired weight/weight ratio (polymer/pDNA) and mixed by vigorous vortexing for 10 seconds. Polyplexes were further allowed to stand for 30 minutes prior to use. The determination of hydrodynamic diameters and zeta potentials of polyplexes was performed by Dynamic Light Scattering (DLS). Results were expressed as mean±standard deviation (SD) of three independent experiments with 3 runs each.

TABLE 1

Size and zeta-potential of P(AMD-CBA) polyplexes at different polymer/DNA w/w ratio.

| w/w | Size (nm) | Zeta-potential (mV) |
|---|---|---|
| 5 | 55.8 ± 0.4 | 25.2 ± 4.6 |
| 10 | 69.9 ± 5.5 | 18.4 ± 4.4 |
| 15 | 56.7 ± 1.1 | 30.6 ± 4.1 |
| 20 | 61.7 ± 4.2 | 33.0. ± 3.2 |
| 25 | 57.5 ± 0.2 | 25.5 ± 3.9 |

Example 6

Figure 4:
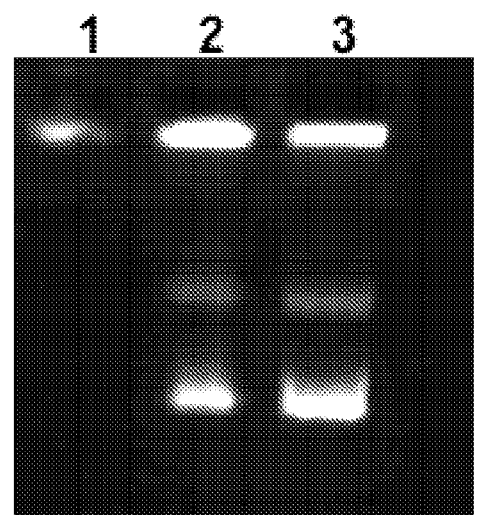
FIG. 4 is an electrophoresis gel that shows polyplex disassembly and pDNA release with 20 mM glutathione (GSH)−/+150 mM NaCl. The polyplexes were prepared at w/w 5. Lane 1: polyplexes alone, Lane 2: +20 mM GSH, Lane 3: +20 mM GSH+NaCl.

Ability of P(AMD-CBA)DNA Polyplex to Disassemble and Release Plasmid DNA in a Reducing Environment The redox-sensitivity and stability of the polyplexes were examined by agarose gel electrophoresis. Polyplexes were prepared at P(AMD-CBA)/pDNA w/w ratio=5 and incubated under indicated conditions of 20 mM GSH with or without the presence of 150 mM NaCl at 37° C. for 1 hour. Samples were then loaded onto a 0.8% agarose gel containing 0.5 μg/mL ethyl bromide (EtBr) and run for 75 minutes at 120 V in 0.5× Tris/Borate/ethylene diamine tetraacetic acid (EDTA) (TBE) running buffer. The gel was visualized under UV. See FIG. 4.

Example 7

Figure 5:
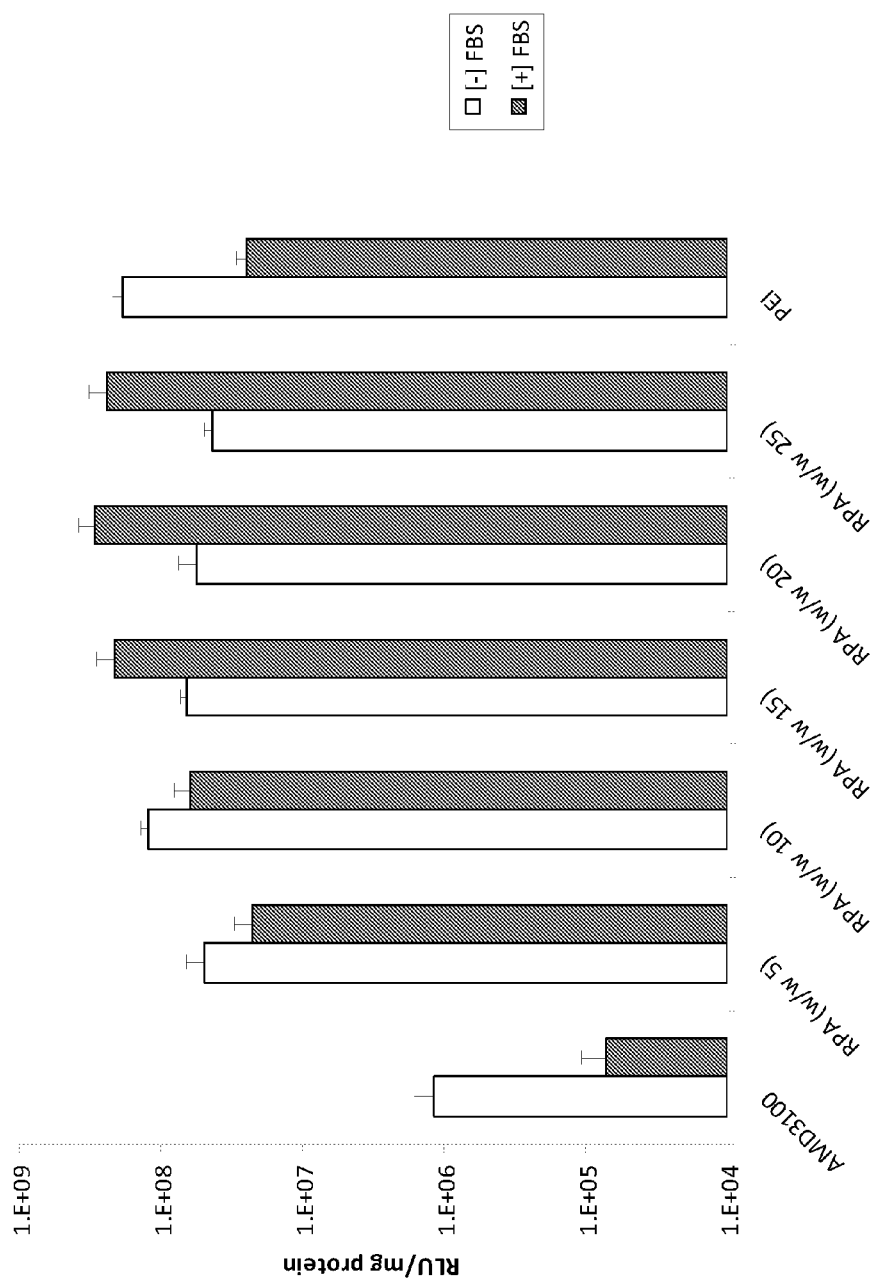
FIG. 5 is a graph of the relative light units (RLU)/mg protein versus weight/weight ratio that shows transfection efficiency of P(AMD-CBA) polyplexes prepared using different w/w ratio in B16F10 cells.

Transfection Efficiency of the Complexes of P(AMD-CBA) with Luciferase Reporter Gene Plasmid DNA B16F10 cells were seeded in 48 well plate at a density of 40,000 cells/well 24 hours prior to transfection. The cells were incubated with the polyplexes (DNA dose: 0.5 µg/well) in 175 µL of medium with or without 10% v/v fetal bovine serum (FBS). Wherever indicated, 100 µM of chloroquine was present in the media to improve the endosomal escape. After 4 hours incubation, polyplexes were completely removed and the cells were cultured in complete culture medium for 24 hours. The medium was then discarded and the cells were lysed in 100 µL of 0.5× cell culture lysis reagent buffer (Promega, Madison, Wis.) for 30 minutes. To measure the luciferase content, 100 µL of 0.5 mM luciferin solution was automatically injected into each well of 20 µL of cell lysate and the luminescence was integrated over 10 seconds using BioTek Synergy 2 Microplate Reader. Total cellular protein in the cell lysate was determined by the BCA protein assay using calibration curve constructed with standard bovine serum albumin solutions (Pierce, Rockford, Ill.). See FIG. 5.

Example 8

Synthesis of P(Cyc-CBA)

A series of three P(Cyc-CBA) was synthesized by Michael addition of different molar ratio of cyclam and N',N'-Cystamine bisacrylamide (CBA). Calculated amounts of cyclam and CBA were weighed and dissolved in methanol/water mixture (v/v 7:3). Polymerization was allowed to proceed in the dark at 37° C. for 24-72 hours before gelation. HCl in ethanol (1.25 M) was then added to form the HCl salt of the polymers. The precipitated products were centrifuged down and washed with ethanol twice to remove the extra acid. The products were then dried using vacuum pump and redissolved in water. After deep dialysis against water for 2 days (MWCO 1,000 for P(Cyc-CBA)/3 and MWCO 3,500 for P(Cyc-CBA/2 and 1.8), the polymers were lyophilized and ready to use.

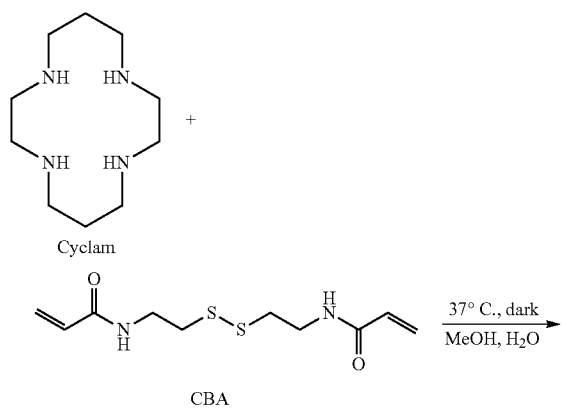

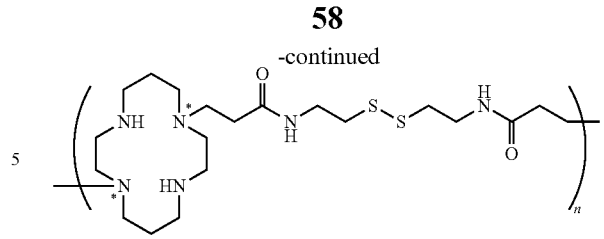

P(Cyc-CBA)

* could be any secondary amine and could have multiple attachments to the same ring
Synthetic route of P(Cyc-CBA) * Exact loacation of the CBA attachment could not be determined. Any of the secondary amines of either of the rings are susceptible to modification.

Example 9

Characterization of P(Cyc-CBA)

Figure 6:
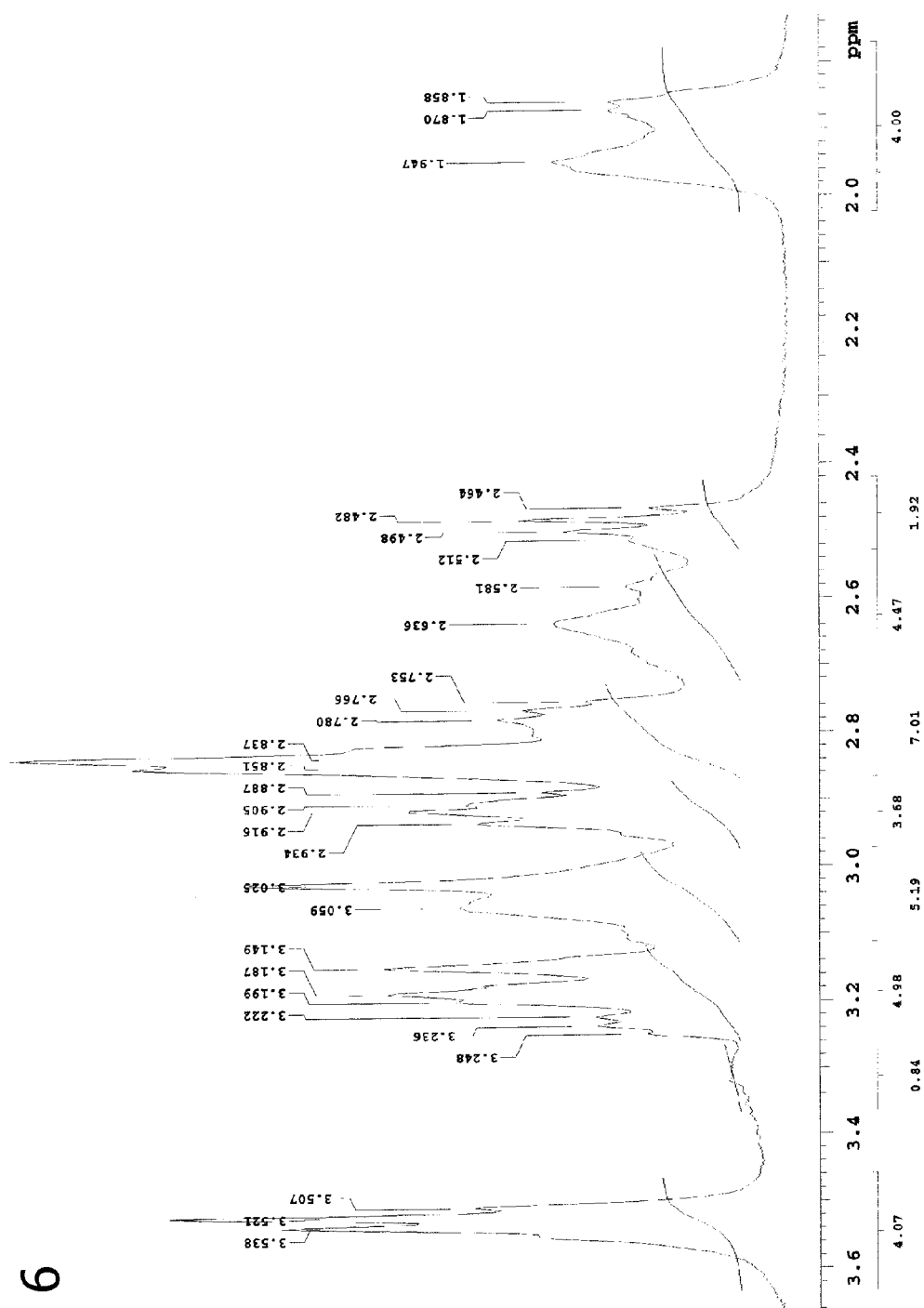
FIG. 6 is a $^1$H NMR of one of the polymers prepared from the polymerization of cyclam (Cyc) and N,N'-Cystamine bisacrylamide (CBA) (P(Cyc-CBA)).

The composition of the polymers was analyzed by $^1$H NMR. Molecular weight of the polymers was determined by Gel Permeation Chromatography (GPC) (Malvern Instruments). Sodium acetate (0.3 M, pH 5) was used as an eluent at a flow rate of 0.3 mL/minute. See FIG. 6.

TABLE 2

Characterization of P(Cyc-CBA).

| | Molar Ratio | Feeding Ratio | Cyclam % | Mn | Mw | PDI |
|---|---|---|---|---|---|---|
| P(Cyc-CBA)/3 | 1.5 | 3 | 56.6 | 3,131 | 4,420 | 1.412 |
| P(Cyc-CBA)/2 | 1 | 2 | 49.6 | 12,030 | 13,714 | 1.14 |
| P(Cyc-CBA)/1.8 | 0.9 | 1.8 | 47.8 | 12,912 | 13,751 | 1.065 |

Example 10

Condensation of Plasmid DNA by P(Cyc-CBA)

Figure 7:
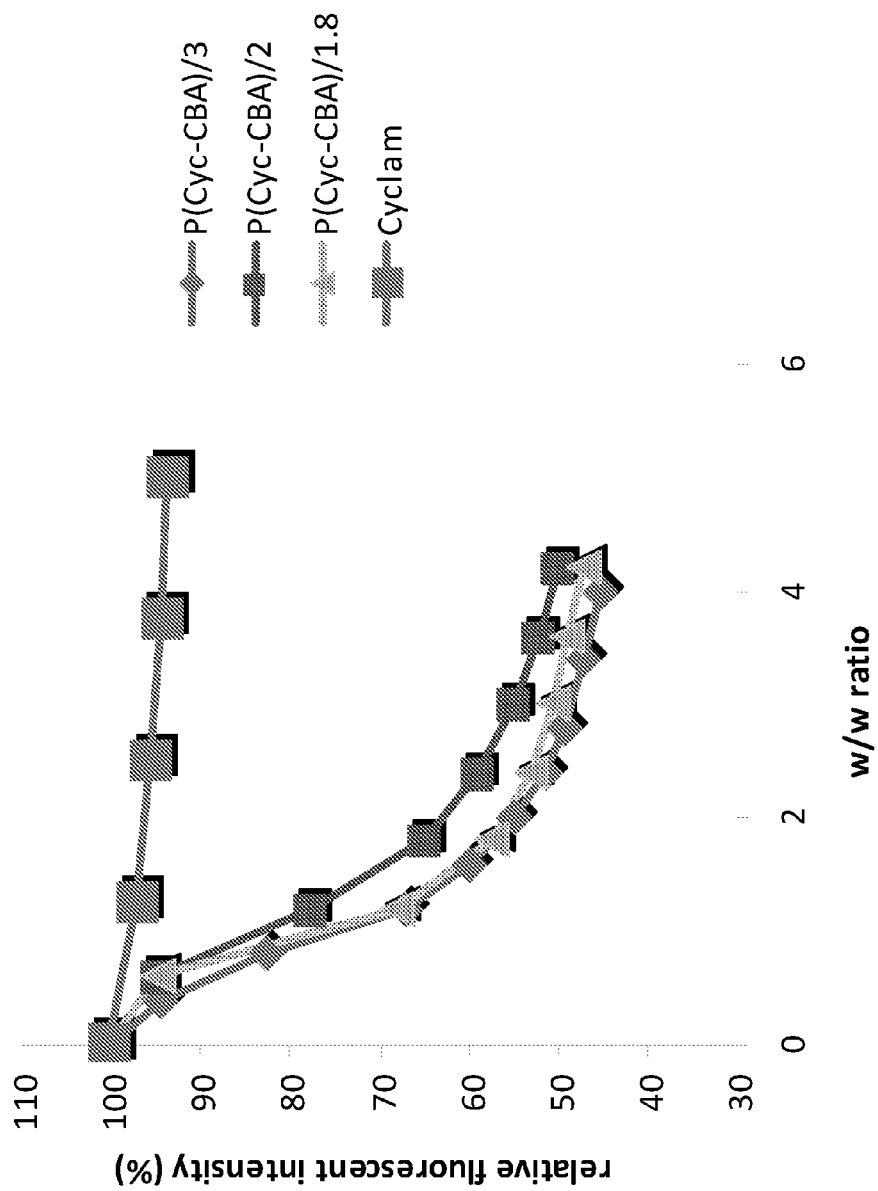
FIG. 7 is a graph of relative fluorescence intensity versus weight/weight ratio that shows pDNA condensation of P(Cyc-CBA) polymer and Cyclam by EtBr exclusion assay.

The ability of P(Cyc-CBA) to condense pDNA was determined by ethidium bromide exclusion (EtBr) assay by measuring the changes in EtBr/pDNA fluorescence. pDNA solution at a concentration of 20 µg/mL was mixed with EtBr (1 µg/mL) and fluorescence was measured and set to 100% using an excitation wavelength of 540 nm and an emission wavelength of 590 nm. Fluorescence readings were taken following a stepwise addition of the polycation solution, and the condensation curve for each polycation was constructed. See FIG. 7.

Example 11

Preparation and Physical Characterization of P(Cyc-CBA) Polyplexes with Plasmid DNA gWiz-Luc pDNA solution (Aldevron) at a concentration 20 µg/mL was prepared in 10 mM HEPES buffer (pH 7.4). Polyplexes were formed by adding predetermined volume of polymer to achieve the desired weight/weight ratio (polymer/pDNA) and mixed by vigorous vortexing for 10 seconds. Polyplexes were further allowed to stand for 30 minutes prior to use. The determination of hydrodynamic diameters and zeta potentials of polyplexes was performed by Dynamic Light Scattering (DLS). Results were expressed as mean±standard deviation (SD) of three independent experiments with 3 runs each.

TABLE 3

Size and zeta-potential of P(Cyc-CBA) polyplexes at different w/w ratio.

| Polymer | w/w | Size (nm) | Zeta-potential (mV) |
| --- | --- | --- | --- |
| P(Cyc-CBA)/3 | 5 | 101.7 ± 1.7 | 13.3 ± 1.3 |
|  | 10 | 124.4 ± 6.6 | 13.9 ± 1.9 |
|  | 15 | 111.0 ± 1.1 | 17.0 ± 5.4 |
|  | 20 | 113.8 ± 3.6 | 14.7 ± 3.2 |
|  | 25 | 125.3 ± 1.8 | 17.3 ± 2.7 |
| P(Cyc-CBA)/2 | 5 | 119.2 ± 1.9 | 21.4 ± 3.7 |
|  | 10 | 124.9 ± 2.2 | 26.1 ± 2.1 |
|  | 15 | 204.9 ± 9.0 | 16.0 ± 2.0 |
|  | 20 | 167.0 ± 2.6 | 17.0 ± 2.1 |
|  | 25 | 163.0 ± 2.8 | 15.5 ± 2.7 |
| P(Cyc-CBA)/1.8 | 5 | 87.4 ± 1.5 | 16.3 ± 2.3 |
|  | 10 | 89.5 ± 3.3 | 22.7 ± 3.8 |
|  | 15 | 121.3 ± 3.3 | 28.6 ± 2.8 |
|  | 20 | 80.9 ± 2.9 | 19.8 ± 1.8 |
|  | 25 | 79.9 ± 1.1 | 17.1 ± 1.8 |

Example 12

Disassembly and pDNA Release from P(Cyc-CBA) Polyplexes

Figure 8:
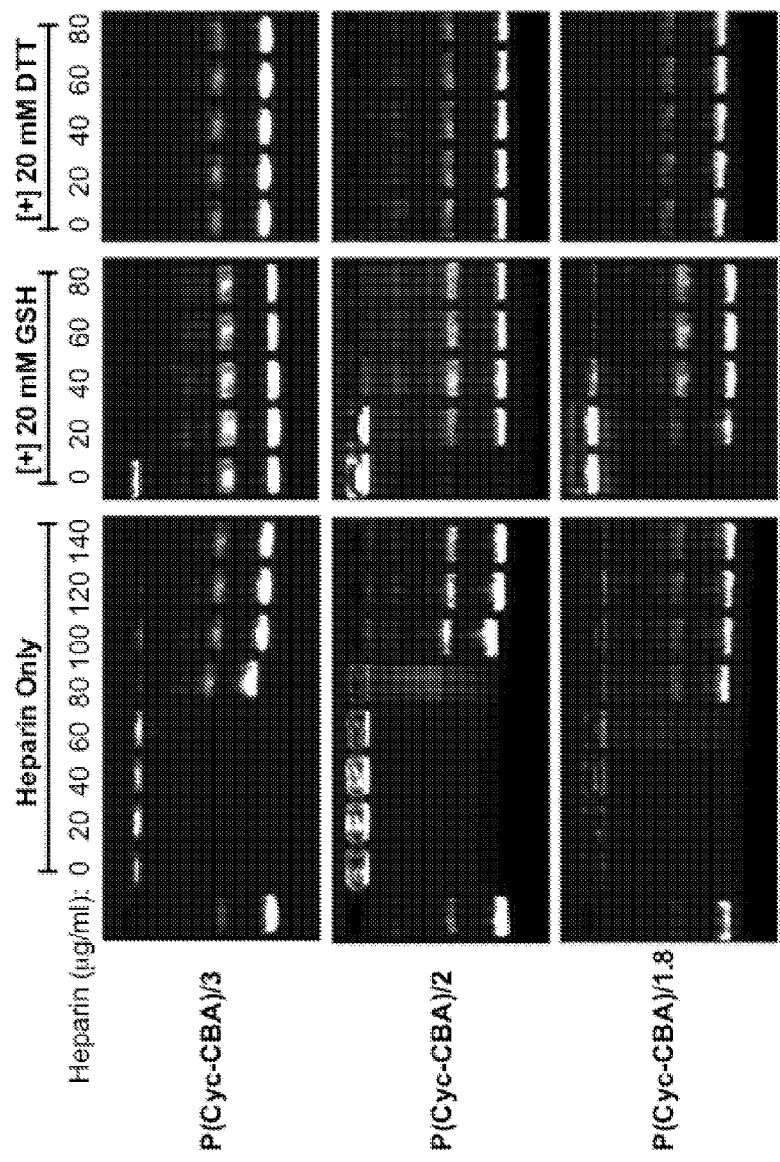
FIG. 8 is a series of electrophoresis gels that show polyplex disassembly and pDNA release with heparin −/+20 mM GSH or DTT. The polyplexes were prepared at w/w 5.

The redox-sensitivity and stability of the polyplexes were examined by agarose gel electrophoresis. Polyplexes were prepared at P(Cyc-CBA)/pDNA w/w ratio=5 and incubated under indicated conditions of different concentrations of heparin with or without a reducing agent (either GSH or DTT) at 37° C. for 1 hour. Samples were then loaded onto a 0.8% agarose gel containing 0.5 μg/mL EtBr and run for 75 minutes at 120 V in 0.5× Tris/Borate/EDTA (TBE) running buffer. The gel was visualized under UV. See FIG. 8.

Example 13

Transfection Efficiency of the Complexes of P(Cyc-CBA) with Luciferase Reporter Plasmid Human breast cancer cell line MDA-MB-231 was a kind gift from Dr. Jing Li, Karmanos Cancer Institute (Detroit, Mich.). The cells were maintained in RPMI1640 medium supplemented with 10% FBS. Murine melanoma cell line B16F10 and human hepatocellular carcinoma cell line Hep G2 were purchased from ATCC (Manassas, Va.). B16F10 cells were maintained in DMEM media supplemented with 10% FBS and Hep G2 cells were maintained in MEM media supplemented with 10% FBS. All the cells were cultured at 37° C. in 5% CO2 atmosphere.

All transfection experiments were conducted in 48-well plates with cells at logarithmic growth phase following a previously published protocol (Read, Singh et al. 2005). Cells were seeded at a density of 40,000 cells/well 24 h prior to transfection. On the day of transfection, cells were incubated with the polyplexes (DNA conc. 2.35 μg/mL) in 170 μL of serum-free or 10% FBS-containing media. After 4 h incubation, polyplexes were completely removed and the cells were cultured in complete culture medium for 24 h prior to measuring luciferase expression. The medium was discarded and the cells were lysed in 100 μL of 0.5× cell culture lysis reagent buffer (Promega, Madison, Wis.) for 30 min. To measure the luciferase content, 100 μL of 0.5 mM luciferin solution was automatically injected into each well of 20 μL of cell lysate and the luminescence was integrated over 10 s using Synergy 2 Microplate Reader (BioTek, VT). Total cellular protein in the cell lysate was determined by the Bicinchoninic acid protein assay using calibration curve constructed with standard bovine serum albumin solutions (Pierce, Rockford, Ill.). Transfection activity was expressed as relative light units (RLU)/mg cellular protein±SD of quadruplicate samples.

Figure 9A:
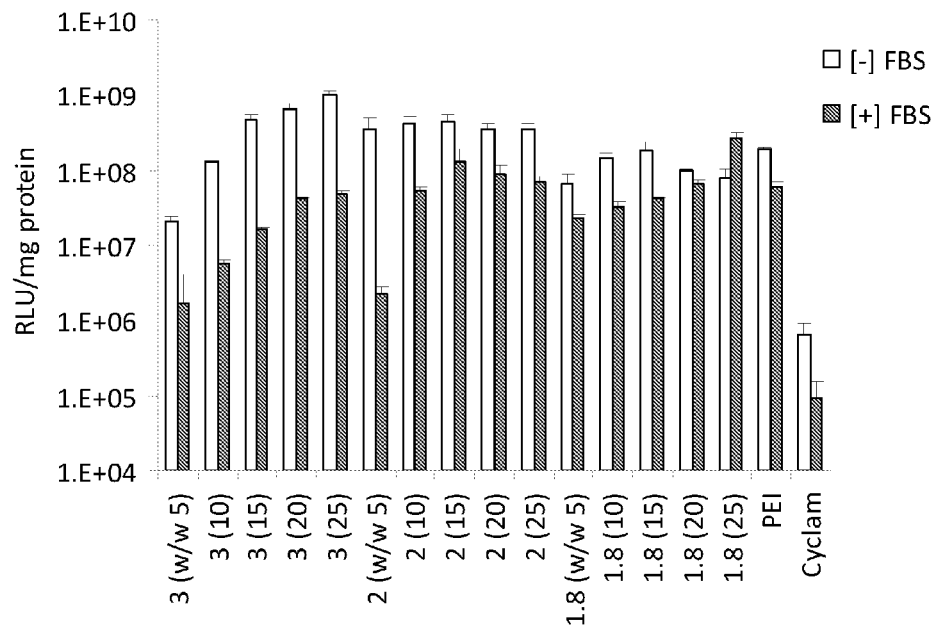
FIG. 9 are graphs of the relative light units (RLU)/mg protein versus weight/weight ratio that show transfection efficiency of P(Cyc-CBA) polyplexes prepared using different w/w ratio in (A) B16F10 cells and (B) MDA-MB-231 cells.
Figure 9B:
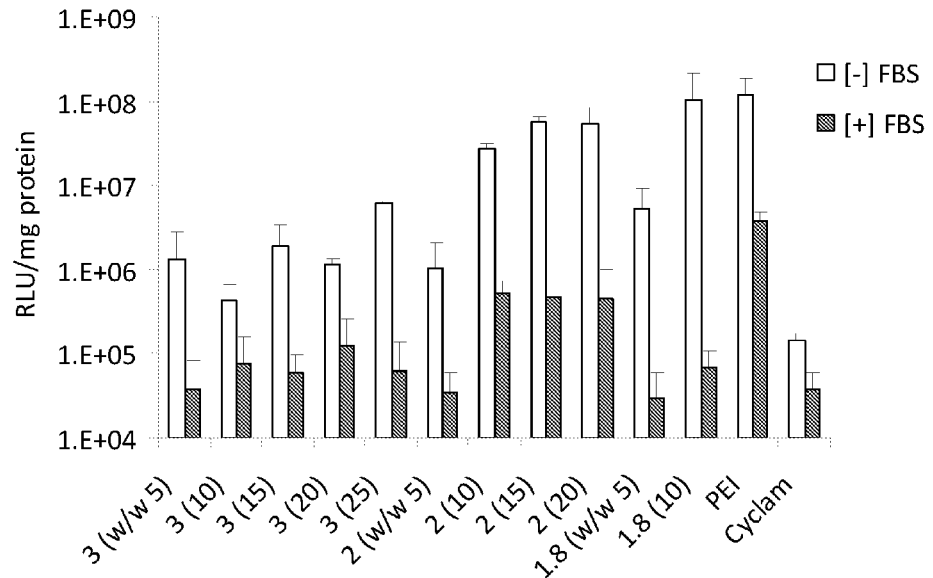

B16F10 cells were seeded in 48 well plate at a density of 40,000 cells/well 24 hours prior to transfection. The cells were incubated with the polyplexes (DNA dose: 0.5 μg/well) in 175 μL of medium with or without 10% v/v FBS. Wherever indicated, 100 μM of chloroquine was present in the media to improve the endosomal escape. After 4 hours incubation, polyplexes were completely removed and the cells were cultured in complete culture medium for 24 hours. The medium was then discarded and the cells were lysed in 100 μL of 0.5× cell culture lysis reagent buffer (Promega, Madison, Wis.) for 30 minutes. To measure the luciferase content, 100 μL of 0.5 mM luciferin solution was automatically injected into each well of 20 μL of cell lysate and the luminescence was integrated over 10 seconds using BioTek Synergy 2 Microplate Reader. Total cellular protein in the cell lysate was determined by the BCA protein assay using calibration curve constructed with standard bovine serum albumin solutions (Pierce, Rockford, Ill.). See FIG. 9.

Example 14

Cytotoxicity of P(Cyc-CBA)

Figure 10:
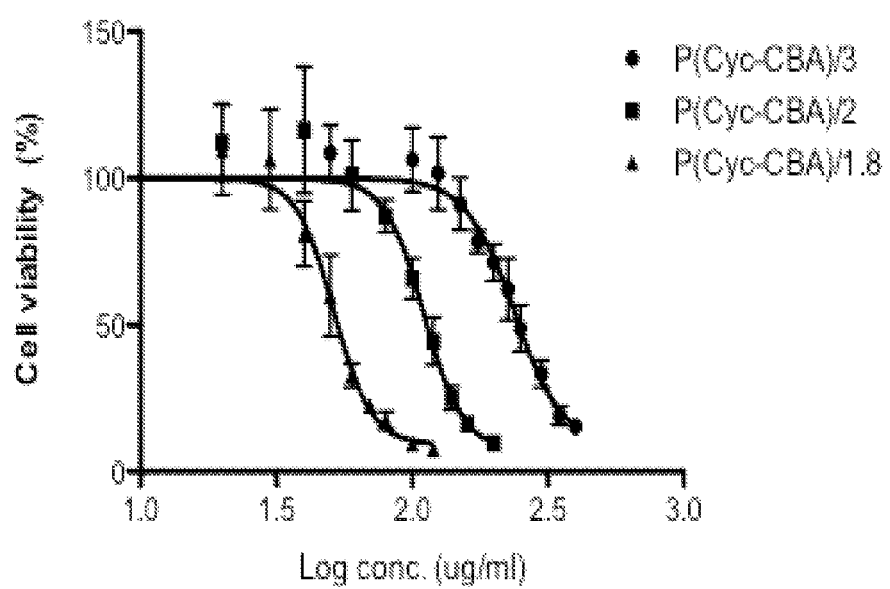
FIG. 10 is a graph or the percent cell viability versus the Log of the concentration for P(Cyc-CBA) by MTS assay. $IC_{50}$ values for P(Cyc-CBA)/3, P(Cyc-CBA)/2 and P(Cyc-CBA)/1.8 in MDA-MB-231 cells are 247.6±15.9 μg/ml, 113.6±12.0 μg/ml and 53.3±3.9 μg/ml, respectively

Cytotoxicity of P(Cyc-CBA) in MDA-MB-231 cells was determined by MTS assay using a commercially available kit (CellTiter 96® Aqueous Cell Proliferation Assay, Promega). 20,000 cells were seeded per well in 96-well plates 24 hours ahead. The culturing medium was first removed and then replaced with 150 μL of medium containing increasing concentration of the polycations. After 24 hours, the incubation medium was removed and a mixture of 100 μL of fresh serum-free medium and 20 μL of MTS reagent solution was added to each well. The cells were incubated for at 37° C. in CO$_2$ incubator for 2 hours. The absorbance at wavelength 505 nm was then measured to determine cell viability. IC$_{50}$ values were calculated by Prism Graphpad Software. See FIG. 10.

Toxicity of polycations was also evaluated by MTS assay in Hep G2 cells and CXCR4+U2OS cells. HepG2 were purchased from ATCC (Manassas, Va.). Hep G2 cells were maintained in MEM supplemented with 10% FBS. Human epithelial osteosarcoma U2OS cells stably expressing human CXCR4 receptor fused to the N-terminus of enhanced green fluorescent protein were purchased form Fisher Scientific. The cells were cultured in DMEM supplemented with 2 mM L-Glutamine, 10% FBS, 1% Pen-Strep and 0.5 mg/ml G418. The cells were plated into 96-well microtiter plates at a density of 20,000 cells/well. After 24 h, culture medium was replaced by 150 μl of serial dilutions of a polymer in serum-supplemented medium and the cells were incubated for 24 h. Polymer solutions were aspirated and replaced by a mixture of 100 μl serum-free media and 20 μl of MTS reagent (CellTiter 96® AQueous Non-Radioactive Cell Proliferation Assay, Promega). After 2 h incubation, the absorbance was measured spectrophotometrically in Synergy 2 Microplate Reader (BioTek, VT) at a wavelength of 490 nm. The relative cell viability (%) was calculated as [A]sample/[A]untreated×100%. The IC50 were calculated as polymer concentration, which inhibits growth of 50% of cells relative to untreated cells. The IC50 values were calculated based on "log(inhibitor) vs.

response-absolute IC50" curve fitting procedure in Graph-Pad Prism, with constrains of Fifty=50, Top=100 and a formula Y=Bottom+(Top−Bottom)/(1+10^((Log IC50−X)*HillSlope+Log((Top−Bottom)/(Fifty−Bottom)−1))). In both cell lines RPA had remarkably low toxicity compared with 25-kDa poly(ethyleneimine) (PEI) control. The IC50 of RPA was almost 50 times higher than that of PEI in Hep G2 cells (599 vs. 12 μg/mL) and 116 times higher in U2OS cells (464 vs. 4 μg/mL). The IC50 of control polymer RHB was 57 μg/mL in Hep G2 cells.

Example 15

Transition Metal Complexes of P(Cyc-CBA)

Figure 11A:
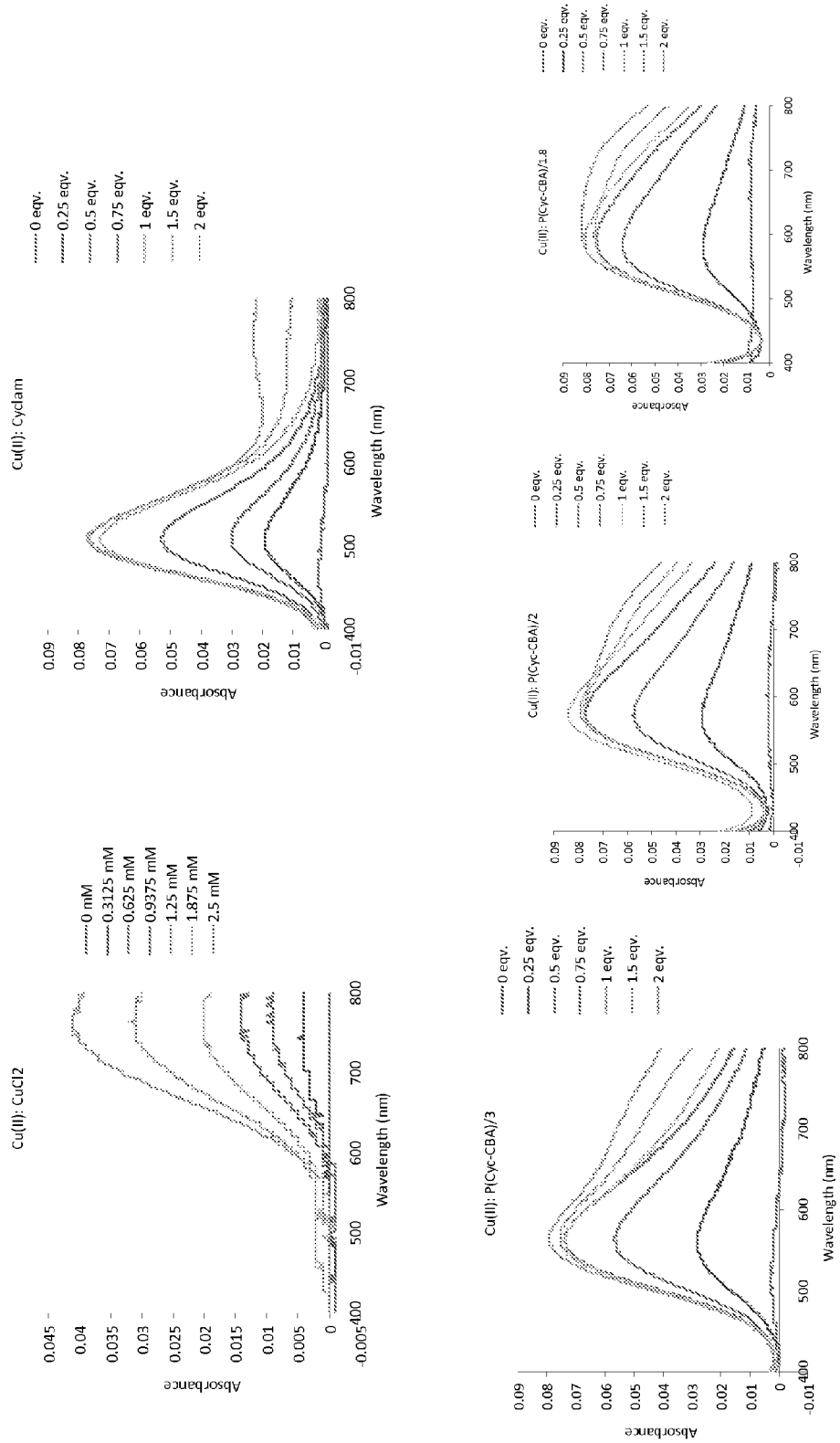
FIG. 11 is a series of graphs of absorbance versus wavelength (nm) for metal complexation of P(Cyc-CBA). (A) Copper(II) complexation; (B) Zn(II) complexation; (C) Co(II) complexation. The absorption spectrums were obtained by UV-vis spectroscopy.
Figure 11B:
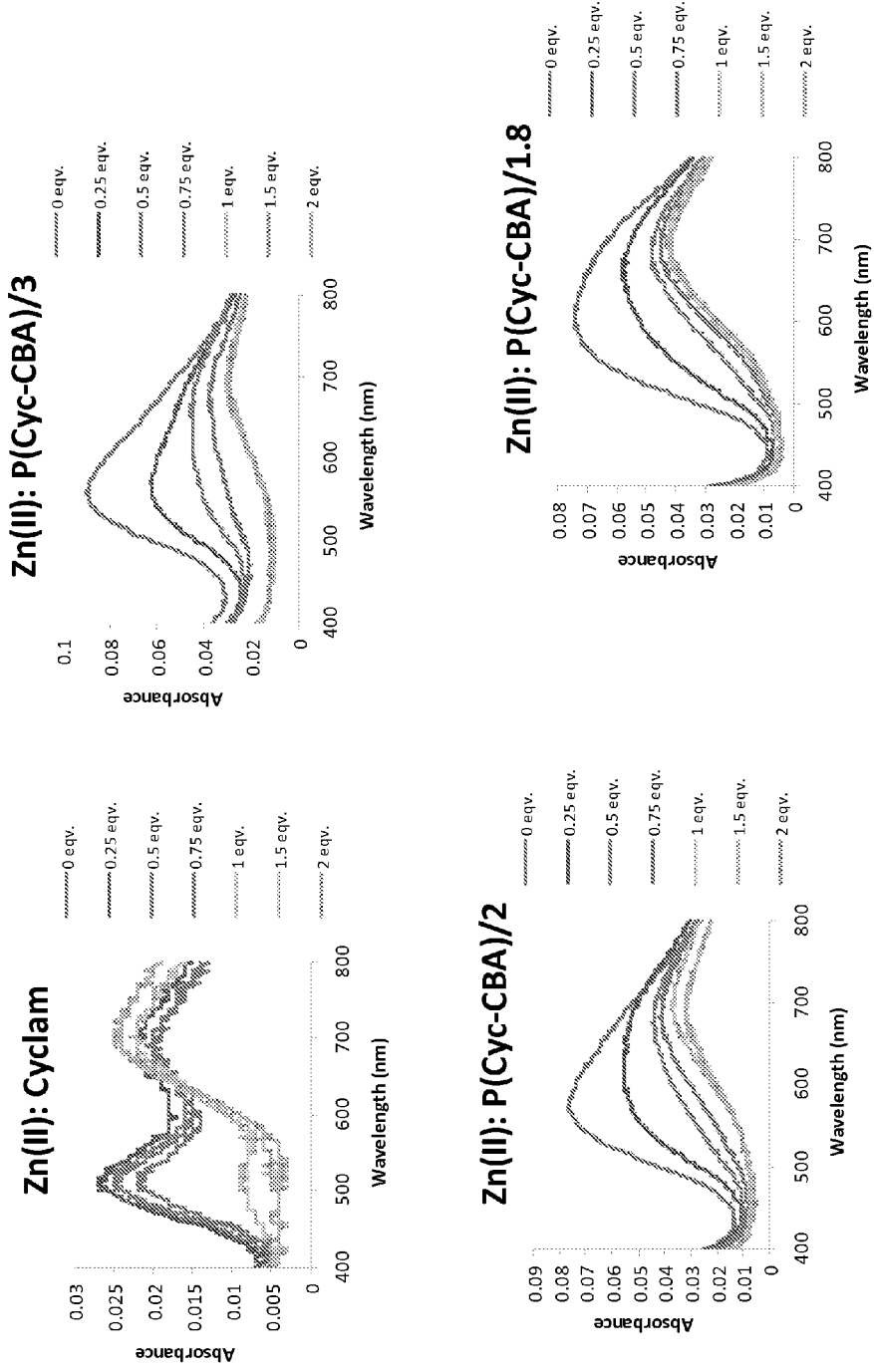
Figure 11C:
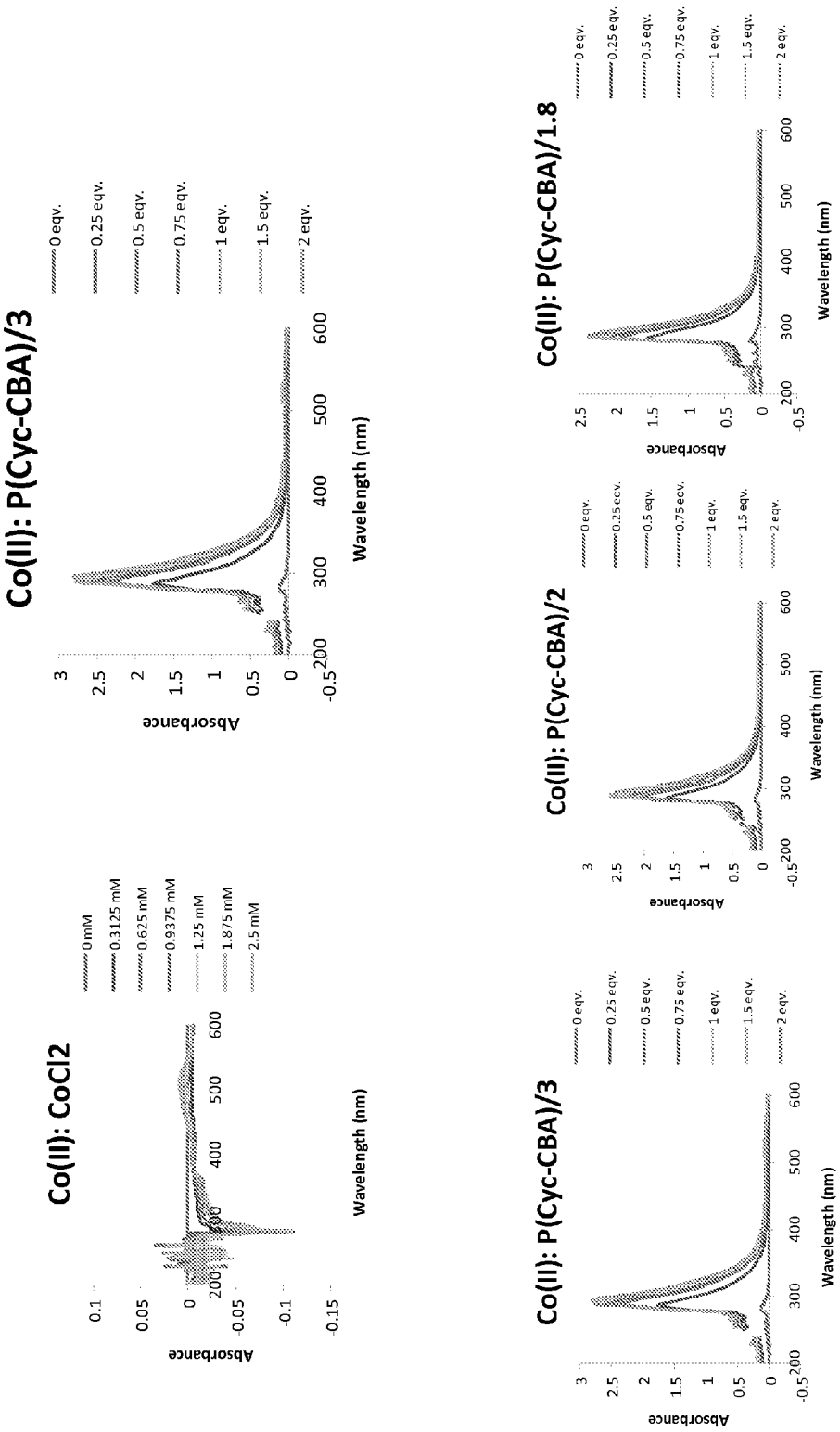

Metal complexes of P(Cyc-CBA) polymers were formed by incubating polymer solutions with 10 mM $CuCl_2$, $ZnCl_2$ or $CoCl_2$ at 37° C. for 1 hours. For Cu(II) complexation, cyclam (1.25 M) or P(Cyc-CBA) polymers (0.5 mg/ml) were incubated with different concentration of $CuCl_2$ (1 equivalent=1.25 M) in sodium acetate buffer (pH 6) at room temperature for 1 h. For Zn(II) complexation, cyclam (1.25 M) or P(Cyc-CBA) polymers (0.5 mg/mL) were incubated with different concentration of $ZnCl_2$ (1 equivalents=1.25 M) in cacodylate buffer (pH 7.4) at room temperature for 1 hours and then 1 equivalent of $CuCl_2$ were added. For Co(II) complexation, cyclam (1.25 M) or P(Cyc-CBA) polymers (0.5 mg/mL) were incubated with different concentration of $CoCl_2$ (1 equivalent=1.25 M) in HEPES buffer (pH 7.4) at room temperature for 1 hours. All the absorption spectrums were obtained by UV-vis spectroscopy. See FIG. 11.

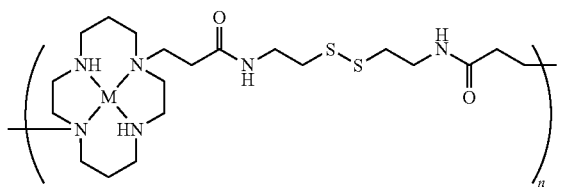

M = Cu(II), Zn(II), Co(II), Mn(II) etc.

Example 16

Figure 12:
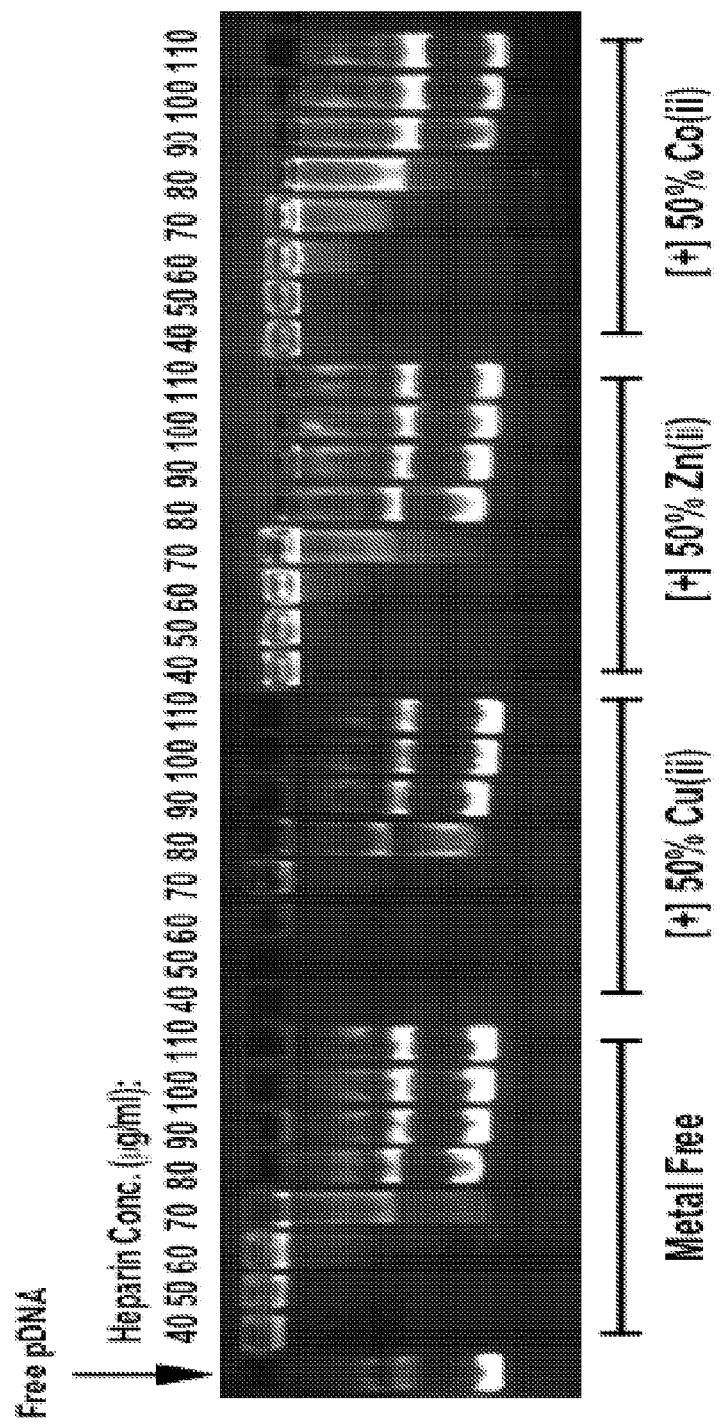
FIG. 12 is a series of electrophoresis gels showing stability of metal complexes of P(Cyc-CBA) against heparin disassembly using P(Cyc-CBA) with 50% metal complexation.

Stability of Plasmid DNA Polyplexes of the P(Cyc-CBA) Metal Complexes pDNA polyplexes were prepared at w/w 5 and incubated under indicated conditions of different concentrations of heparin at 37° C. for 1 hour. Samples were then loaded onto a 0.8% agarose gel containing 0.5 μg/mL EtBr and run for 75 minutes at 120 V in 0.5× Tris/Borate/EDTA (TBE) running buffer. The gel was visualized under UV. See FIG. 12.

Example 17

Transfection Efficiency of the Polyplexes of Luciferase Plasmid DNA with the Metal Complexes of P(Cyc-CBA)

Figure 13A:
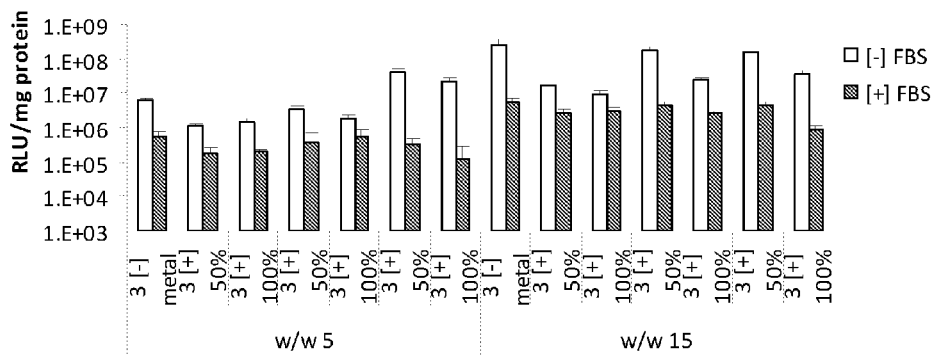
FIG. 13 is a series of graphs of the RLU/mg protein versus weight/weight ratio showing transfection efficiency of metal complexes of P(Cyc-CBA) in B16F10 cells. (A) P(Cyc-CBA)/3; (B) P(Cyc-CBA)/2; (C) P(Cyc-CBA)/1.8.
Figure 13B:
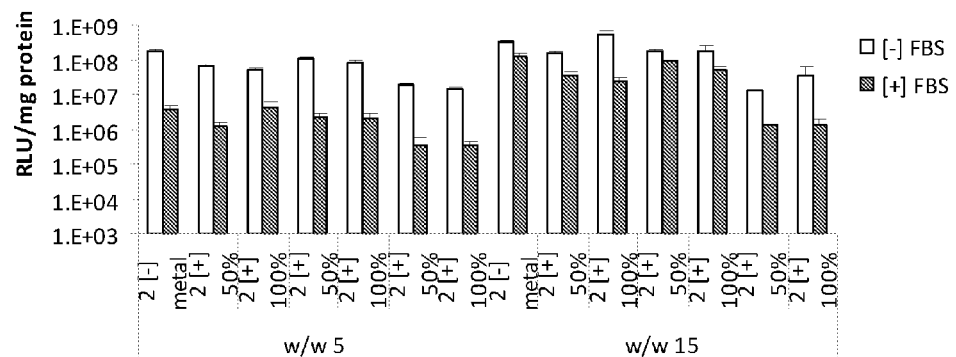
Figure 13C:
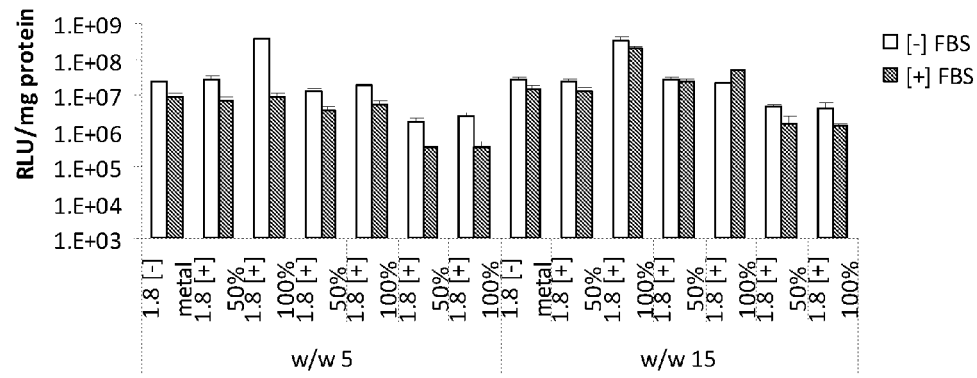

B16F10 cells were seeded in 48 well plate at a density of 40,000 cells/well 24 hours prior to transfection. The cells were incubated with the polyplexes of luciferase plasmid DNA with the metal complexes of P(Cyc-CBA) (DNA dose: 0.5 μg/well) in 175 μL of medium with or without 10% v/v FBS. Wherever indicated, 100 μM of chloroquine was present in the media to improve the endosomal escape. After 4 hours incubation, polyplexes were completely removed and the cells were cultured in complete culture medium for 24 hours. The medium was then discarded and the cells were lysed in 100 μL of 0.5× cell culture lysis reagent buffer (Promega, Madison, Wis.) for 30 minutes. To measure the luciferase content, 100 μL of 0.5 mM luciferin solution was automatically injected into each well of 20 μL of cell lysate and the luminescence was integrated over 10 seconds using BioTek Synergy 2 Microplate Reader. Total cellular protein in the cell lysate was determined by the BCA protein assay using calibration curve constructed with standard bovine serum albumin solutions (Pierce, Rockford, Ill.). See FIG. 13.

Example 18

Cytotoxicity of the Metal Complexes of P(Cyc-CBA)

Cytotoxicity of metal complexes of P(Cyc-CBA) in MDA-MB-231 cells was determined by MTS assay using a commercially available kit (CellTiter 96® Aqueous Cell Proliferation Assay, Promega). 20,000 cells were seeded per well in 96-well plates 24 hours ahead. The culturing medium was first removed and then replaced with 150 μL of medium containing increasing concentration of the polycations. After 24 hours, the incubation medium was removed and a mixture of 100 μL of fresh serum-free medium and 20 μL of MTS reagent solution was added to each well. The cells were incubated for at 37° C. in $CO_2$ incubator for 2 hours. The absorbance at wavelength 505 nm was then measured to determine cell viability. $IC_{50}$ values were calculated by Prism Graphpad Software.

TABLE 4

| $IC_{50}$ values of metal complexes of P(Cyc-CBA). | | | |
|---|---|---|---|
| w/w | P(Cyc-CBA)/3 | P(Cyc-CBA)/2 | P(Cyc-CBA)/1.8 |
| Metal Free | 247.6 ± 15.9 | 113.6 ± 12.0 | 53.31 ± 3.9 |
| 50% Cu | 319.2 ± 15.1 | 132.9 ± 13.2 | 64.37 ± 4.4 |
| 100% Cu | 143.8 ± 10.9 | 83.9 ± 3.2 | 34.7 ± 2.6 |
| 50% Zn | 204.0 ± 20.1 | 106.6 ± 8.8 | 36.8 ± 4.7 |
| 100% Zn | 166.4 ± 30.8 | 104.4 ± 11.2 | 41.4 ± 1.0 |
| 50% Co | 138.1 ± 18.8 | 110.4 ± 16.9 | 71.0 ± 4.3 |
| 100% Co | 129.8 ± 9.7 | 74.4 ± 5.4 | 53.0 ± 2.2 |

Example 19

P(AMD-CBA) Antagonizes CXCL12

Figure 14:
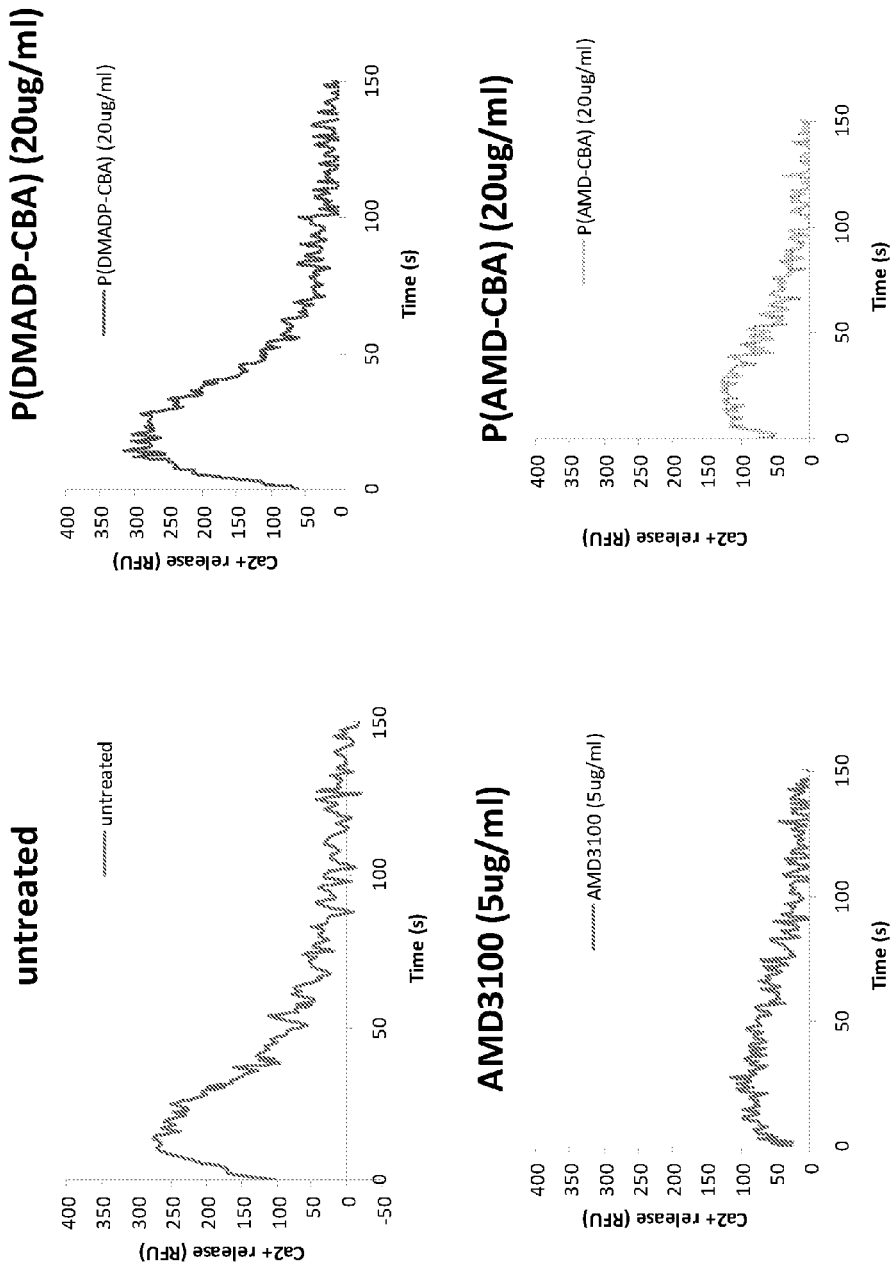
FIG. 14 is a series of graphs of the $Ca^{2+}$ release versus time showing that P(AMD-CBA) and AMD3100 are CXCL12 antagonists.

Binding of chemokine CXCL12 to its receptor CXCR4 triggers an intracellular signal transduction cascade comprising a transient increase in cytosolic free calcium. The antagonist AMD3100 is unable to trigger the calcium flux and therefore inhibits the chemokine-induced calcium signaling.[71] We used fluorescent calcium indicator Fluo-3 to monitor the intracellular calcium flux induced by CXCL12 (FIG. 14). Cells untreated with any of the tested agents exhibited a rapid increase in intracellular calcium after CXCL 12 stimulation, confirming activation of the CXCR4 by CXCL12 binding. Treatment with AMD3100 and P(AMD-CBA) had a strong antagonistic effect on this signaling pathway. In contrast, the control non-cyclam polycation P(DMADP-CBA) failed to block the CXCR4-mediated signaling pathway showing similar levels of calcium flux as control cells. This demonstrates that P(AMD-CBA) is CXCR4 antagonist.

Example 20

Low Toxicity of P(AMD-CBA)

Figure 15:
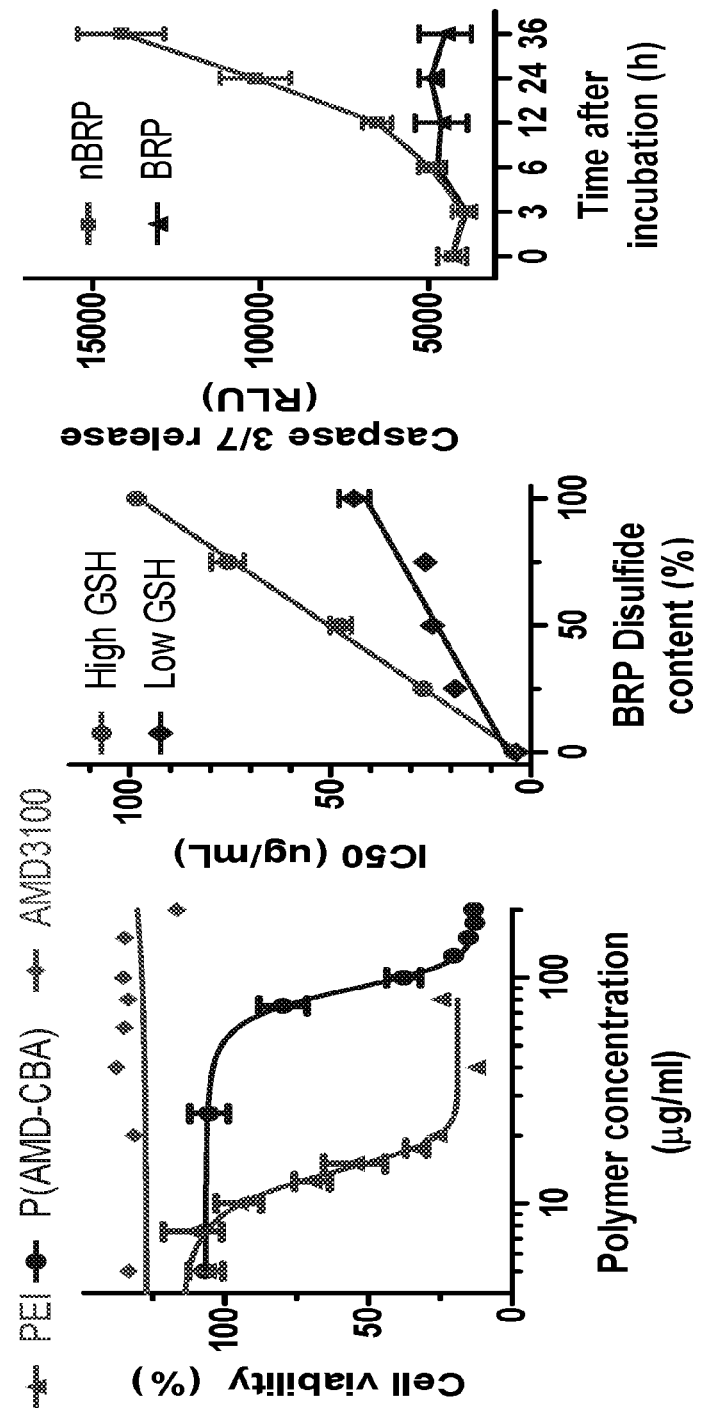
FIG. 15 is a series of graphs showing decreased toxicity of bioreducible polycations based on polymers prepared from CBAP(AMD-CBA).

The cytotoxicity of P(AMD-CBA) was determined by MTS assay as described above in example 14. See FIG. 15. Using BRP with different disulfide content, synthesized as described in Chen, J., C. Wu, and D. Oupicky, "Bioreducible Hyperbranched Poly(amido amine)s for Gene Delivery." *Biomacromolecules*, (2009) 10: 2921-2927), the toxicity of BRP is a direct function of the disulfide content and intracellular GSH concentration. This is shown by the increasing $IC_{50}$ with increasing disulfide content and by steeper $IC_{50}$ vs. disulfide content dependence in cells with higher GSH content. See FIG. 15 middle. Non-degradable nBRP induce apoptosis as soon as 12 hours after incubation, no significant apoptosis induction was observed for BRP for up to 36 hours. See FIG. 15 right. This study provides additional information about the safety of bioreducible polycations.

Example 21

Colloidal Stabilization of P(AMD-CBA) Polyplexes

Figure 16:
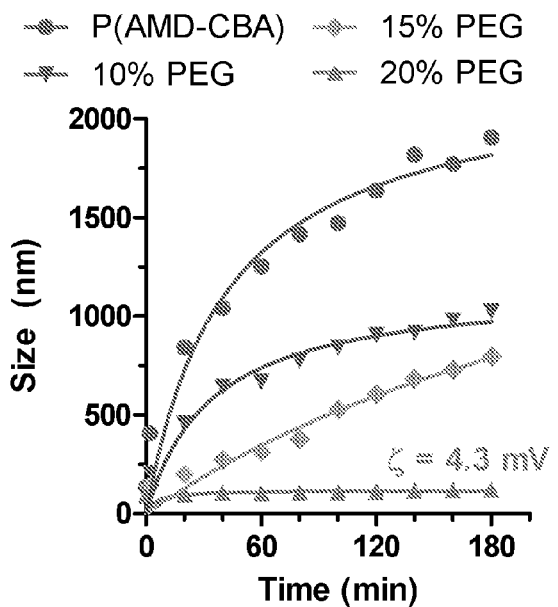
FIG. 16 is a graph of the size of polyplexes versus time that shows the colloidal stability of the polyplexes.

The colloidal stability of P(AMD-CBA) polyplexes was increased by formulating the polyplexes with a mixture of P(AMD-CBA) and PEG-BRP copolymer See FIG. 16. The polyplexes were formed generally using the procedure described in example 11. Increasing the content of PEG-BRP in the formulation decreased the rate of aggregation of the polyplexes in 0.15 M NaCl. The colloids were stable for at least 3 hours when the formulation included 20% PEG-BRP.

Example 22

Evaluation of P(AMD-CBA) Complexes with Copper

Figure 17:
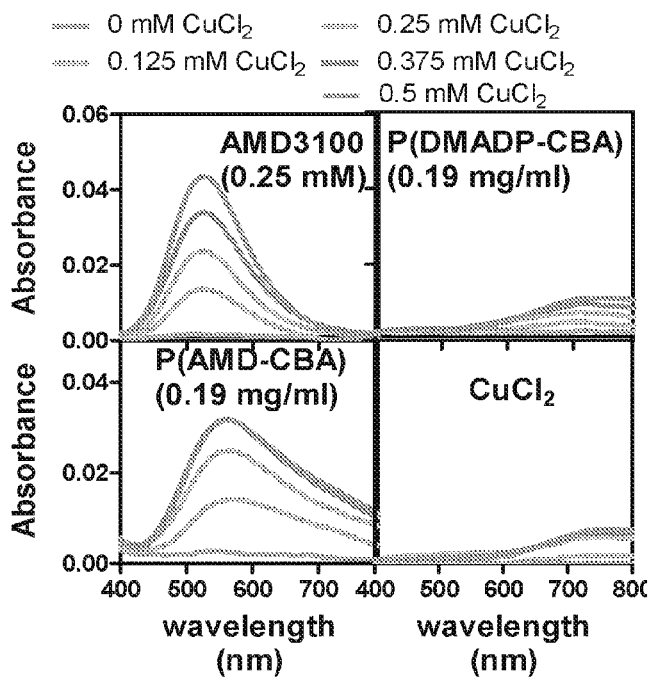
FIG. 17 is a series of graphs of absorbance versus wavelength (nm) for metal complexation of AMD3100, P(DMADP-CBA) control, P(AMD-CBA), and $CuCl_2$. The absorption spectrums were obtained by UV-vis spectroscopy.

Complexes of AMD3100 with positron emitting $^{64}$Cu ($t_{1/2}$ 12.7 h) have been used to image CXCR4 positive cancers using PET. (Nimmagadda, S., M. Pullambhatla, K. Stone, G. Green, Z. M. Bhujwalla, and M. G. Pomper, "Molecular Imaging of CXCR4 Receptor Expression in Human Cancer Xenografts with [Cu-64]AMD3100 Positron Emission Tomography." *Cancer Res*, (2010) 70: 3935-3944). We first compared the copper binding ability of P(AMD-CBA) to AMD3100 and control non-cyclam polycation P(DMADP-CBA) in a titration experiment with $CuCl_2$. See FIG. 17. The procedure was similar to that described in example 15. Absorption at 550 nm showed formation of the copper complexes with AMD3100 and P(AMD-CBA) but not with the control P(DMADP-CBA) where DMADP is N,N-dimethyldipropylenetriamine. Analysis of the titration data that not all cyclam rings in the polycation can bind copper (most likely due to reduced accessibility of some cyclam rings in the polymer and electrostatic repulsion). Since P(AMD-CBA) form copper complexes, they are suitable for PET imaging studies.

Example 23

Condensation of Plasmid DNA by Copper Complexes of P(AMD-CBA)

Figure 18:
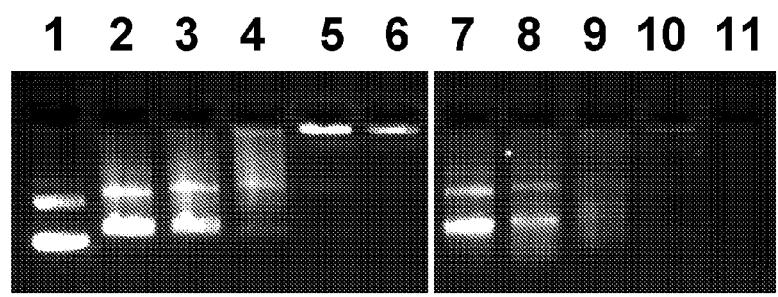
FIG. 18 is electrophoresis gel showing DNA condensation by Cu—P(AMD-CBA).
Figure 19:
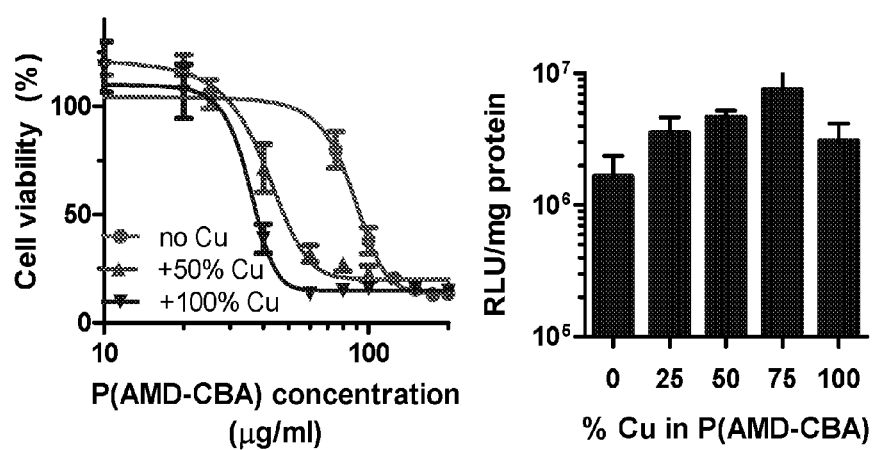
FIG. 19 is a series of graphs showing the effect of copper complexation on toxicity (left) and transfection activity (right).

Copper complexation increased the overall charge of P(AMD-CBA) and provided more effective DNA condensation using the procedure generally described in example 10. See FIG. 18. However, this increased charge also increased toxicity of the polycation with increasing copper content as determined using the procedure described in example 14. See FIG. 19. No toxicity was seen for equivalent concentration of $CuCl_2$, confirming that the toxicity was the result of increased cationic character of P(AMD-CBA). The luciferase transfection of the copper complexes of P(AMD-CBA) increased with increasing copper content and reached maximum when 75% of the cyclam moieties were complexed with copper as determined using the procedure of example 13. See FIG. 19. However, since the amount of copper needed for microPET imaging is negligible, no adverse effects on toxicity are anticipated.

Example 24

Formation and Characterization of RPA Polyplexes gWiz-Luc DNA solution in 10 mM HEPES (pH 7.4) was prepared to give a DNA concentration in the final polyplexes=20 µg/mL. Polyplexes were formed by adding predetermined volume of polymer to achieve the desired polycation/DNA weight/weight (w/w) ratio and mixed by vigorous vortexing for 10 seconds. Polyplexes were further allowed to stand for 30 min prior to use. The determination of hydrodynamic diameters and zeta potentials of polyplexes was performed by Dynamic Light Scattering following previously published method. Results were expressed as mean±standard deviation (S.D.) of 3-10 experimental runs.

Example 25

CXCR4 Redistribution Assay

CXCR4+U2OS cells were plated in 96-well plate 18-24 h before the experiment at a seeding density of 8,000 cells per well. The cells were first washed with 100 µL assay buffer (DMEM supplemented with 2 mM L-Glutamine, 1% FBS, 1% Pen-Strep and 10 mM HEPES) twice and then incubated with different concentrations of the polycations or AMD3100 in assay buffer containing 0.25% DMSO at 37° C. for 30 min. In experiments with RPA/DNA and RHB/DNA polyplexes (wherein RPA is P(AMD-CBA) and RHB is P(DMADP-CBA), DNA concentration was 0.5 µg/mL. Human SDF-1α (CXCL-12) was then added to each well to make final concentration 10 nM. DMSO alone was used as the negative control, and hSDF-1α alone was used as the positive control. After 1 h incubation at 37° C., the cells were fixed with 4% formaldehyde at room temperature for 20 min followed by 4-time washing with PBS. All the images were taken by EVOS fl microscope at 20×.

The quantification of the receptor redistribution was conducted by ImageXpressMicro high throughput imaging system by Molecular Devices (Sunnyvale, Calif.). The system enables high-quality imaging of 96-well plates based on automatic focusing of fluorescently labeled cell nuclei (by DAPI or Hoechst dye) followed by image analysis by MetaXpress software (High Throughput Mode) based on the average green fluorescent granule intensity (internalized GFP-CXCR4). Untreated cells U2OS cells stimulated with 10 nM CXCL12 were used as negative control (100% CXCR4 translocation) and 300 nM AMD3100 treated cells were used as positive controls (0% CXCR4 translocation). The method was verified by establishing a dose response curve of AMD3100 and its calculated EC50 was comparable with cell line data sheet from Fisher Scientific. The operation of the instrument and analysis of the data were conducted with the help of Steve Swaney at the Center for Chemical Genomics of Life Sciences Institute, University of Michgan (Ann Arbor, Mich.).

Example 26

Cell Invasion Assay

The upper sides of the transwell inserts were coated with 40 µl Matrigel diluted in serum-free medium (v/v 1:3) per insert. The 24-well plates with coated inserts were then placed in 37° C. incubator for 2 h. CXCR4+U2OS cells were trypsinized and resuspended in different concentrations of drugs in serum-free medium for 30 min before adding to the inserts at a final concentration of 10,000 cells in 300 µl medium per insert. 20 nM CXCL12 in serum-free medium as the chemo-attractant was then added to corresponding wells in the companion plate. After 16 h, the non-invaded cells on the upper surface of the inserts were removed with a cotton swab. The invaded cells were then fixed and stained by dipping the inserts into Diff-Quick solution. The images were taken by EVOS ×1 microscope. Five 20× imaging areas were randomly selected for each insert and each sample was conducted in triplicate. Statistical significance of the observed differences in cell invasion was analyzed using non-parametric ANOVA with Dunn's multiple comparison test using GraphPad InStat (v. 3.10). P<0.05 was considered significant.

All transfection experiments were conducted in 48-well plates with cells at logarithmic growth phase. Cells were seeded at a density of 40,000 cells/well 24 h prior to transfection. On a day of transfection, the cells were incubated with the polyplexes (DNA conc. 2.35 µg/ml) in 170 µL of serum-free or 10% FBS containing media. After 4 h incubation, polyplexes were completely removed and the cells were cultured in complete culture medium for 24 h prior to measuring luciferase expression. The medium was discarded and the cells were lysed in 100 µL of 0.5× cell culture lysis reagent buffer (Promega, Madison, Wis.) for 30 min. To measure the luciferase content, 100 µL of 0.5 mM luciferin solution was automatically injected into each well of 20 µL of cell lysate and the luminescence was integrated over 10 s using Synergy 2 Microplate Reader (BioTek, VT). Total cellular protein in the cell lysate was determined by the Bicinchoninic acid protein assay using calibration curve constructed with standard bovine serum albumin solutions (Pierce, Rockford, Ill.). Transfection activity was expressed as RLU/mg cellular protein±SD of quadruplicate samples.

Example 27

Intracellular Distribution of RPA/DNA Polyplexes

Luciferase DNA was labeled with Label IT-Tracker™ CX-Rhodamine Kit (Mirus, Madison, Wis.) according to manufacturer's protocol. 120,000 CXCR4+U2OS cells were plated in glass-bottom dish (MatTek P35GC-0-14-C) 24 h before the experiment. The cells were incubated with RPA/DNA polyplexes prepared at w/w 5 (2.35 µg/mL DNA) for 3 h before adding 10 nM hCXCL12. The cells were incubated for another 1 h before a PBS wash, fixation and imaging by Perkin Elmer Spinning Disk confocal microscope.

Example 28

Physicochemical Characterization of RPA/DNA Polyplexes

Figure 20:
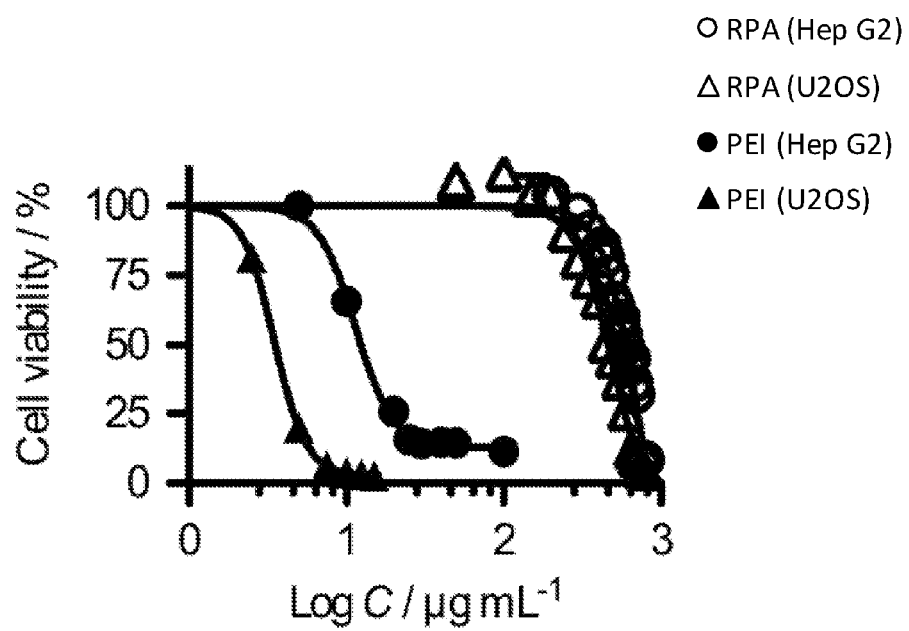
FIG. 20 is a comparison graph of cytotoxicity of RPA and PEI 25 kDa in HepG2 cells (RPA: ○, PEI: ●) and CXCR4+U2OS cells (RPA: Δ, PEI: ▲) determined by MTS.
Figure 21A:
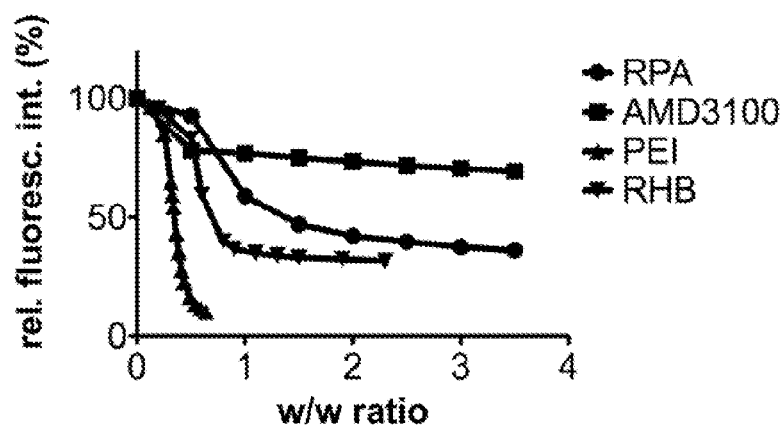
FIG. 21 depicts (a) DNA condensation by EtBr Exclusion assay; (b) reduction triggered DNA release from RPA/DNA polyplexes (polyplexes were prepared at w/w 5).
Figure 21B:
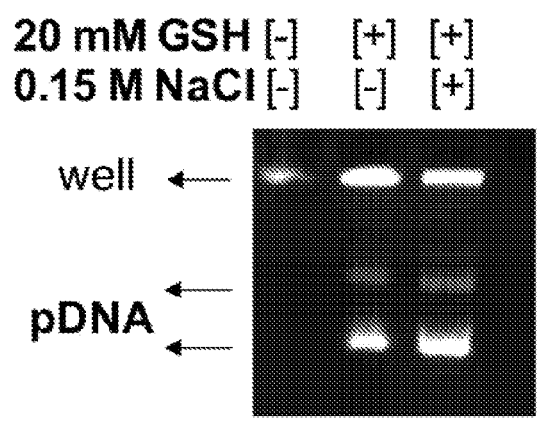

DNA condensation ability of RPA was first compared with PEI, RHB, and AMD3100 by EtBr exclusion assay (FIG. 21a). The condensation curves for all three polycations displayed typical sigmoidal shape, characteristic of DNA condensation by polycations. At pH 7.4, a w/w ratio above 2 was required for RPA to fully condense the DNA, which was higher than that required in case of RHB (w/w 1) and PEI (w/w 0.5). AMD3100 has six secondary amines and two tertiary amines and is thus, to a very limited extent, also able to condense DNA as demonstrated by a decrease in EtBr fluorescence by about 30%. The redox stability of RPA/DNA polyplexes was tested by agarose gel electrophoresis after GSH treatment. As shown in FIG. 21b, 20 mM GSH triggered DNA release form RPA/DNA polyplexes due to the depolymerization of RPA, which decreased its affinity to DNA.

Example 29

CXCR4 Antagonism of RPA

Figure 22:
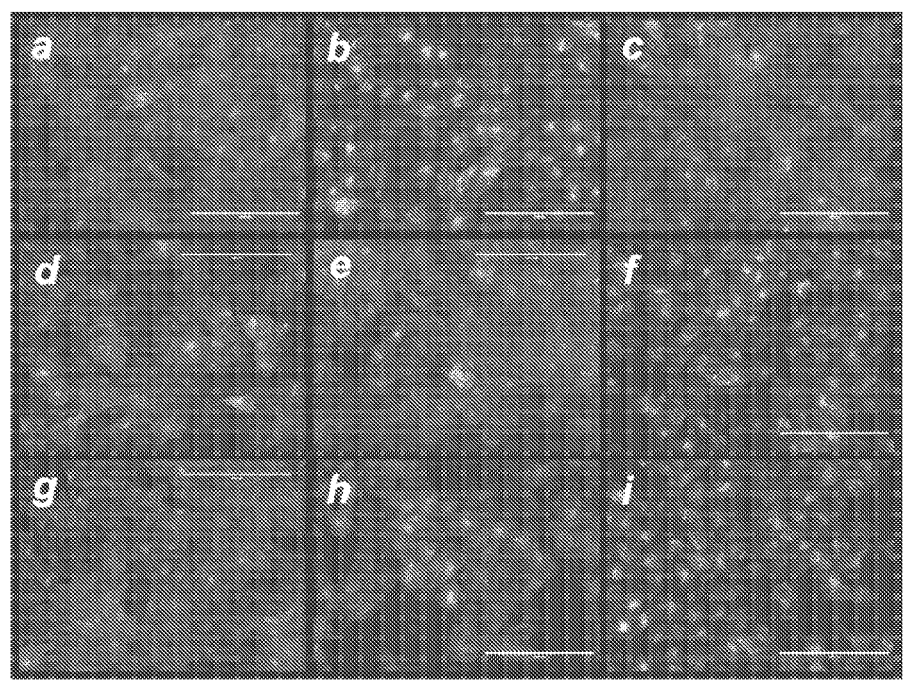
FIG. 22 depicts CXCR4 antagonism of RPA and RPA/DNA polyplexes. CXCR4 receptor redistribution assay was conducted in U2OS cells expressing GFP tagged CXCR4 (a). Before stimulation with 10 nM CXCL12, the cells were treated for 30 min with (b) no drug; (c) 0.24 μg/mL AMD3100.8HCl; (d) 1.5 μg/ml RPA.HCl; (e) 2.5 μg/ml RPA.HCl; (f) 1.5 μg/ml RHB.HCl; (g) RPA/DNA polyplexes (w/w 5, total RPA conc. 2.5 μg/ml); (h) RPA/DNA polyplexes (w/w 1, total RPA conc. 0.5 μg/ml); and (i) RHB/DNA polyplexes (w/w 5, total RHB conc. 2.5 μg/ml). The scale bars for all the images are 200 μm.

When CXCL12 binds to CXCR4 it induces downstream signaling through multiple pathways, including Ras and PI3 kinase. Treatment with CXCR4 antagonists not only prevents the CXCL12-induced downstream signaling but it also inhibits endocytosis of the receptor (Forster, Kremmer et al. 1998; Orsini, Parent et al. 1999; Hatse, Princen et al. 2002; Dar, Goichberg et al. 2005). To evaluate CXCR4 antagonism by RPA and RPA/DNA, CXCR4 receptor redistribution assay was conducted (FIG. 22). The assay used U2OS cells stably expressing human CXCR4 receptor fused to the N-terminus of enhanced green fluorescent protein (EGFP). The assay monitors cellular translocation of the GFP-CXCR4 receptors in response to stimulation with human CXCL12. Here, the internalization of the CXCR4 receptors into endosomes in CXCL12-stimulated cells was observed, as suggested by the punctate distribution of the GFP fluorescence (FIG. 22b) away from the original diffuse pattern in non-stimulated cells (FIG. 22a). To exclude the possibility that the observed effect was caused by nonspecific electrostatic binding of RPA to the negatively charged binding site of the CXCR4 receptor, control polycation RHB without AMD3100 moiety was also tested, but no CXCR4 antagonistic properties was observed (FIG. 22f). Next, a study was done to determine whether polyplexes themselves exhibit CXCR4 antagonism. CXCR4 internalization was inhibited more efficiently by RPA/DNA prepared at w/w 5 (2.5 µg/mL total RPA) than at w/w 1 (FIGS. 22g and h). DNA was not fully condensed in polyplexes at w/w 1 (FIG. 21a); thus, the formulation contained only a minimum amount of free RPA. The findings at w/w 1 thus suggest that the polyplexes themselves may inhibit CXCR4 to some extent. Similar to RHB polymer, no CXCR4 antagonism was observed with RHB/DNA polyplexes (FIG. 22i), confirming that the specific CXCR4 antagonism of RPA and RPA/DNA is due to the AMD3100 moiety in RPA.

Figure 23A:
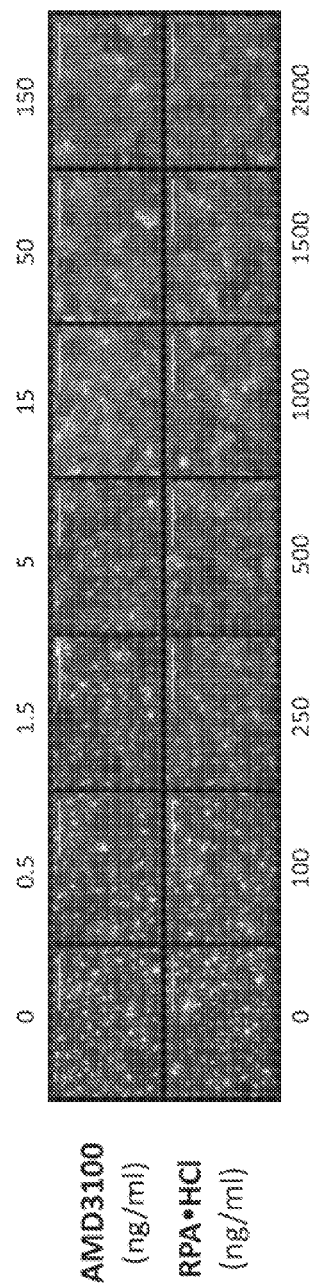
FIG. 23 depicts dose-dependent CXCR4 antagonistic ability of AMD3100 and RPA.HCl. (a) Representative images of redistribution of CXCR4 receptors on U2OS cells treated with increasing concentrations of AMD3100 and RPA; (b) Dose-response curve of CXCR4 inhibition (% receptor translocation) and calculated EC50 value based on images obtained from (a).
Figure 23B:
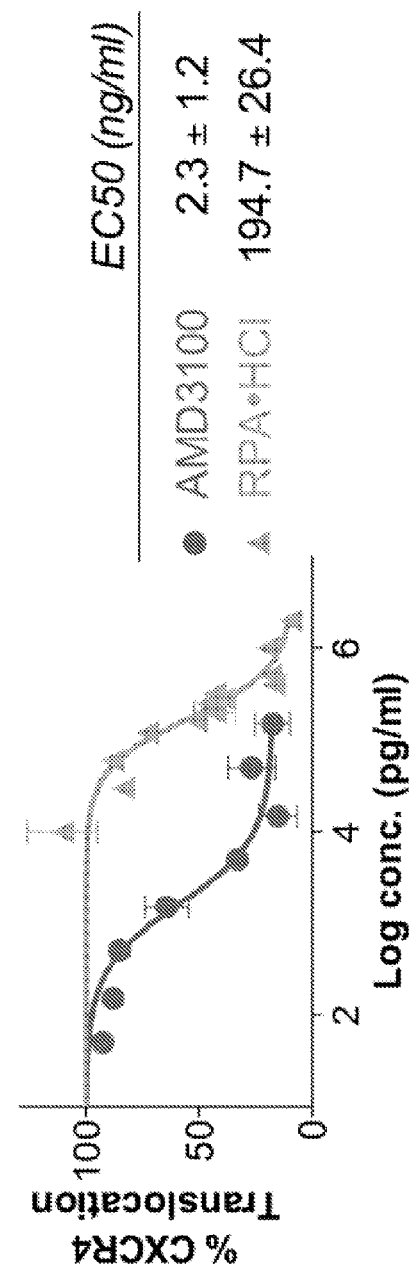

To determine the half-inhibitory (EC50) concentrations of RPA, the CXCR4+U2OS cells were treated with increasing concentrations of RPA.HCl before stimulating them with human CXCL12. AMD3100 was used as positive control. The level of CXCR4 antagonism was evaluated by quantifying the fluorescent intensity of granules (endocytosed GFP-CXCR4) in the individual images. The dose-response curves for AMD3100 and RPA.HCl were established based on % CXCR4 translocation and EC50 values were calculated accordingly (FIG. 23). Based on the results of elemental analysis (data not shown), the equivalent AMD3100 content in RPA could be obtained (60% weight of RPA.HCl).

Example 30

Antimetastatic Ability of RPA by Cell Invasion Assay

Figure 24A:
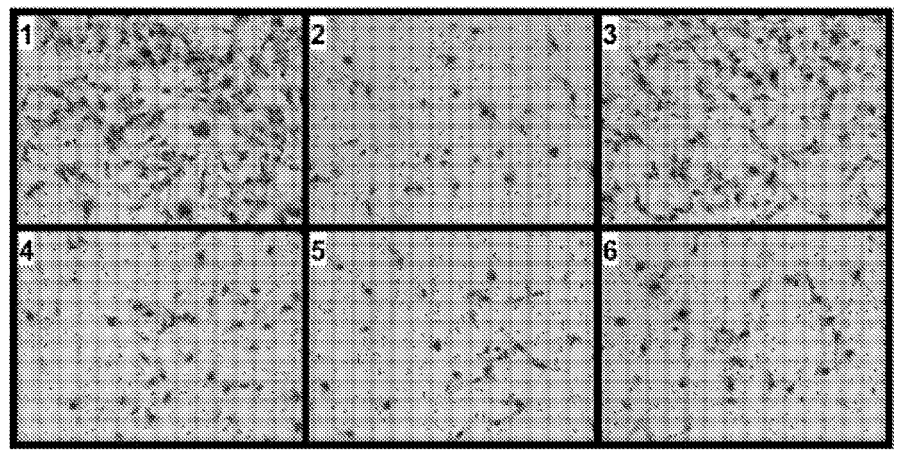
FIG. 24 depicts inhibition of cancer cell invasion by RPA and RPA/DNA polyplexes. (a) Cell invasion assay with CXCR4+U2OS cells treated with 1) no drug; 2) 0.24 μg/mL AMD3100.8HCl; 3) 2 μg/ml RHB.HCl; 4) 2 μg/ml RPA.HCl; 5) 5 μg/ml RPA.HCl and 6) RPA/DNA polyplexes (w/w 5, total RPA conc, 5 μg/ml). Cells were seeded in Matrigel-coated inserts and allowed to invade towards CXCL12-containing medium for 16 h before fixation and imaging. (b) Average number of invaded cells in 20× imaging area.
Figure 24B:
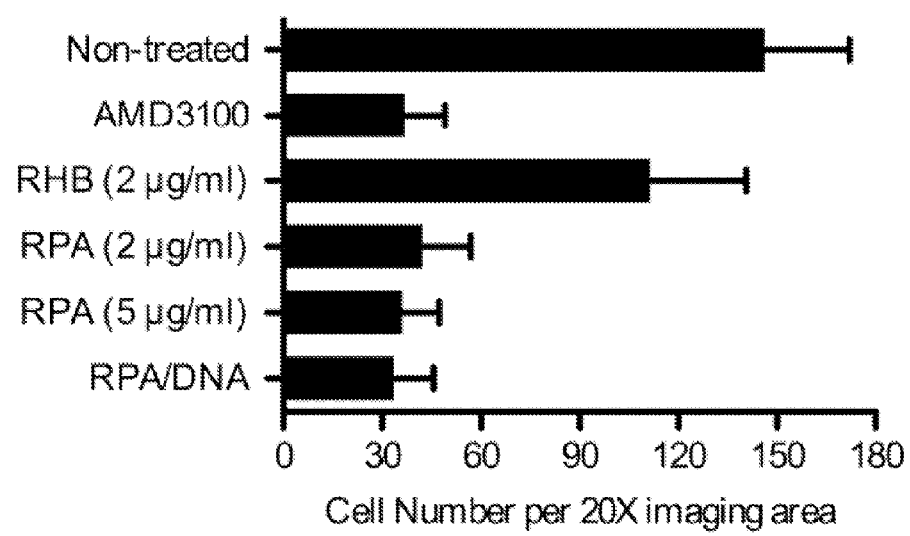

The CXCR4/CXCL12 axis plays a critical role in cancer metastasis due to its function in trafficking and homing of cancer cells to organs that express high levels of CXCL12. Blocking the CXCR4/CXCL12 interactions with small-molecule antagonists suppresses metastasis in a variety of cancers (Yoon, Liang et al. 2007; Liang, Zhan et al. 2012). To further confirm the CXCR4 antagonism of RPA and RPA/DNA polyplexes, the anti-metastatic ability was evaluated by a Matrigel cell invasion assay. As shown in FIG. 24, RPA and RPA/DNA polyplexes effectively blocked CXCL12-mediated invasion of CXCR4+U2OS cells. Both free RPA and RPA/DNA blocked invasion of 71-77% of cells, similar to that of AMD3100 (75%). The DNA dose used in the experiment with the polyplexes (1 µg/mL DNA) was in the range of typical doses used in transfection experiments. The observed decrease in cell invasion with control RHB/DNA polyplexes was not statistically significant ($p>0.05$). At the same time, the differences between RPA and RPA/DNA polyplexes vs. untreated controls were highly significant with $P<0.001$, based on non-parametric ANOVA analysis with Dunn's multiple comparison test. The slight decrease in the number of invaded cells with RHB treatment could also be attributed by higher toxicity of RHB compared with RPA. The membrane damage caused by the treatment with RHB may affect the motility of the cells and thus decrease their ability to invade through the extracellular matrix.

Example 31

Transfection of RPA/DNA Polyplexes

Figure 25A:
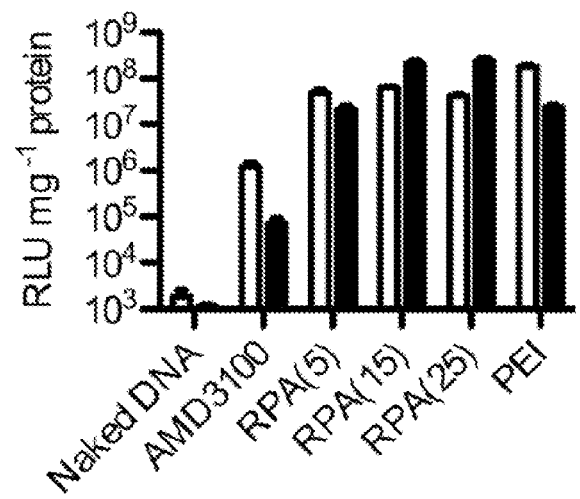
FIG. 25 shows transfection activity of RPA/DNA polyplexes prepared at w/w 5, 15 and 25 in the absence (white bars) and the presence (black bars) of 10% FBS in (a) B16F10 and (b) CXCR4+U2OS cells. (Results are shown as mean luciferase expression in RLU/mg protein±SD, n=3).
Figure 25B:
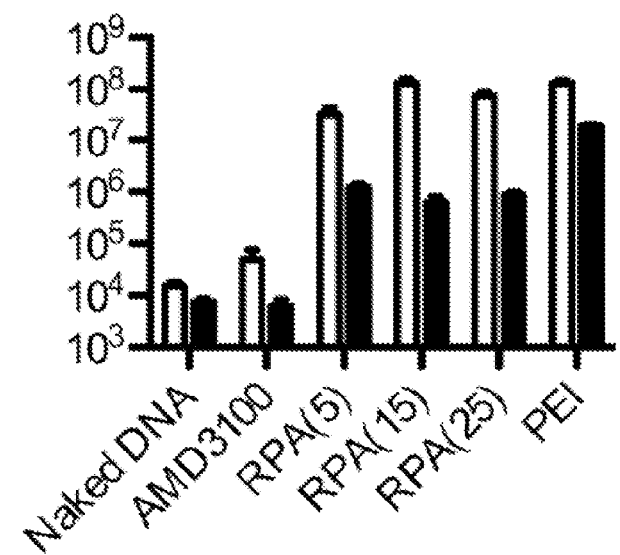

Having confirmed CXCR4 antagonism and inhibition of cancer cell invasion of the synthesized RPA, its gene delivery capability was evaluated (FIG. 25). A routine luciferase transfection experiment was conducted. RPA/DNA polyplexes exhibited high in vitro transfection efficiency that was comparable with that of control PEI/DNA polyplexes and RHB/DNA in B16F10 and U2OS cell lines at a DNA dose of 2.35 µg/mL. It is interesting that AMD3100 itself was able to mediate some transfection, especially in B16F10 cells when compared with naked DNA only. As shown in FIG. 21, the partial DNA condensation is the most likely reason for the observed transfection, which is nevertheless several orders of magnitude below transfection of the polymers.

Example 32

Simultaneous CXCR4 Antagonism and Gene Delivery

Figure 26:
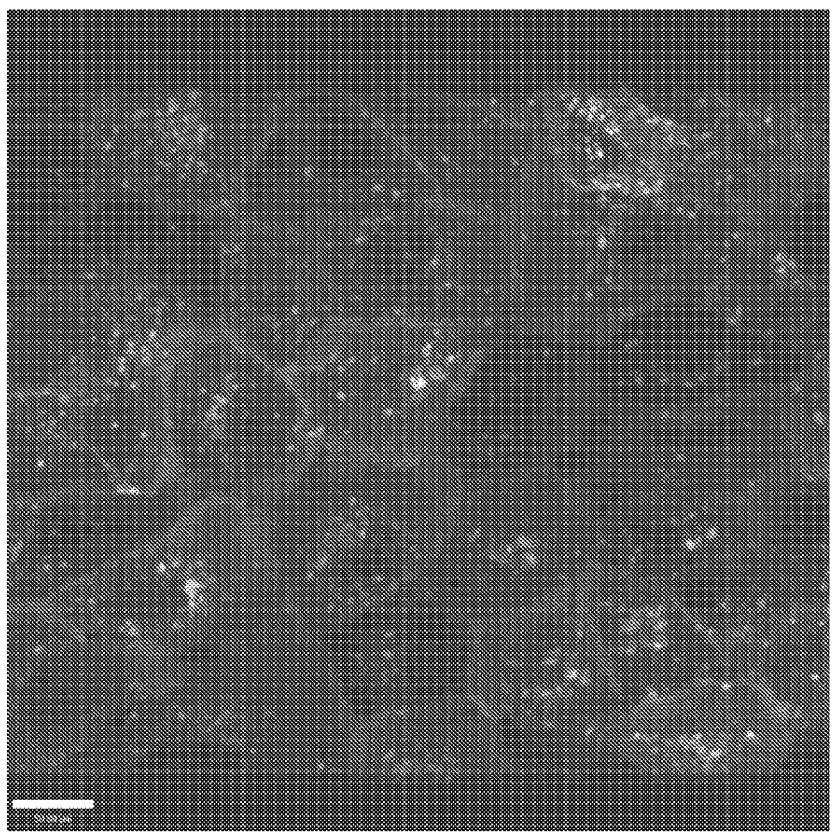
FIG. 26 shows intracellular distribution of RPA/DNA polyplexes in CXCR4+U2OS cells (red fluorescence: CX-Rhodamine labeled plasmid DNA; green fluorescence: GFP-CXCR4 receptor).

As shown in the experiment below, the RPA/DNA polyplexes use an alternative uptake pathway that does not require CXCR4. This is documented by the lack of signal from RPA/DNA polyplexes with fluorescently labeled DNA colocalized with the membrane-present CXCR4 receptor. As shown in FIG. 26, after 3 h incubation with RPA/DNA polyplexes, the CXCR4+U2OS cells were stimulated with hCXCL12 and the confocal image (taken in the middle of the Z-stack) showed more clearly that the GFP-CXCR4 receptors were mostly presented in the cell membrane. At the same time, labeled RPA/DNA polyplexes (red fluorescence) were shown internalized into the cells and not bound with the membrane-localized CXCR4 receptors. While not being bound to a theory, it is believed that the polyplexes are internalized through a different endocytic pathway that does not involve CXCR4.

Figure 27:
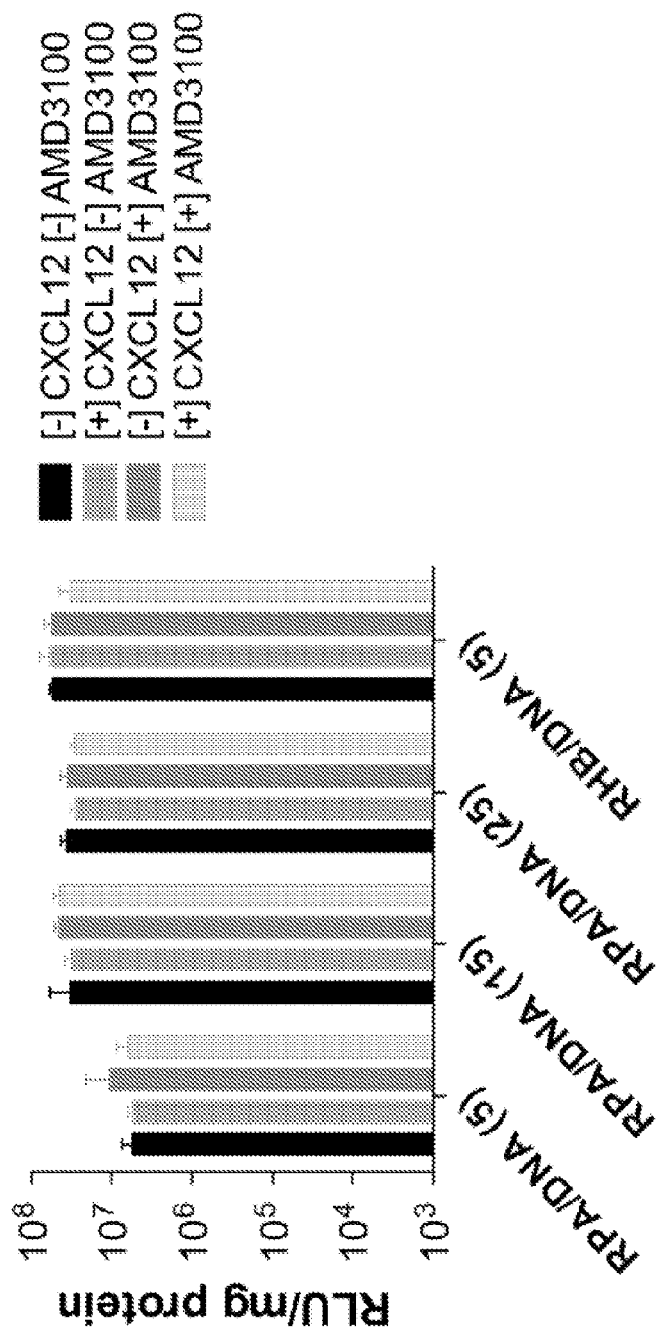
FIG. 27 depicts the effect of CXCR4 stimulation/inhibition on RPA/DNA transfection. CXCR4+U2OS cells were pre-treated with 300 nM AMD3100 for 15 min before adding polyplexes prepared at different w/w ratios. The cells were then stimulated with 10 nM CXCL12 and co-incubated with the polyplexes during transfection.

To further study if CXCR4 inhibition affects the gene delivery function of RPA/DNA polyplexes, AMD3100 was used to block the cell surface CXCR4 receptors before conducting transfection. No significant difference was observed in transfection efficiency in CXCR4+U2OS cells either with or without CXCL12 simulation (FIG. 27). The results suggest that the uptake of RPA/DNA polyplexes is not dependent on binding with CXCR4 receptors.

Figure 28:
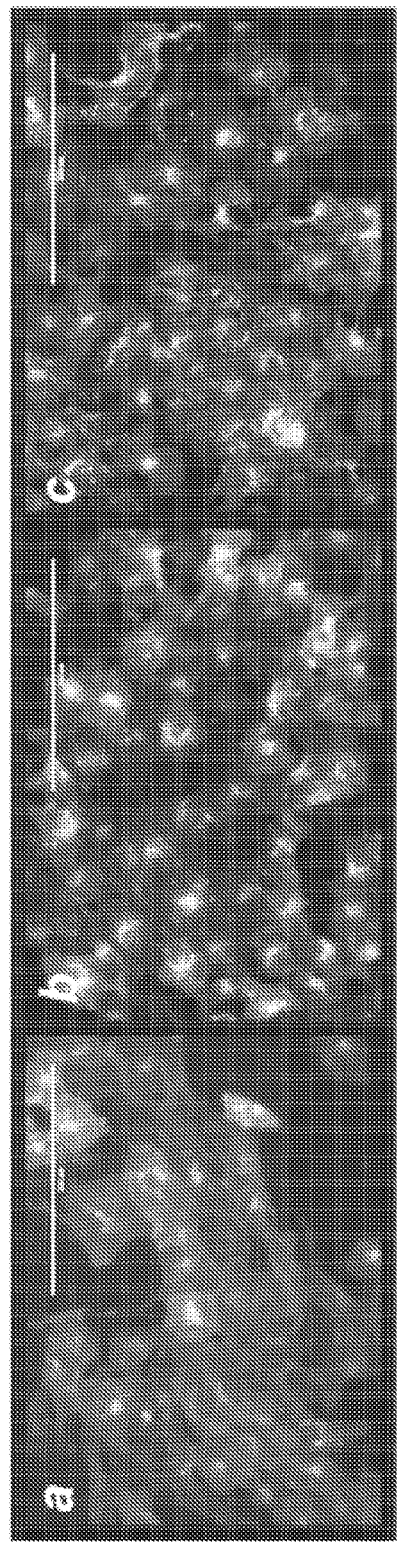
FIG. 28 depicts AMD3100 and RPA do not inhibit phorbol-stimulated CXCR4 internalization. CXCR4+U2OS cells were treated with AMD3100.8HCl (0.24 μg/mL) and then stimulated with a) 10 nM CXCL12 or b) 100 ng/ml of phorbol myristate acetate. c) CXCR4+U2OS cells were treated with RPA/DNA (w/w 5) polyplexes (i.e., 0.5 μg/mL RPA, 0.1 μg/mL DNA) and then stimulated with 100 ng/ml of phorbol myristate acetate.

It has been reported that CXCL12 and phorbol esters trigger CXCR4 internalization through entirely different uptake pathway (Signoret, Oldridge et al. 1997). AMD3100 only inhibits CXCL12-induced CXCR4 endocytosis, but does not affect phorbol ester-induced receptor internalization (Hatse, Princen et al. 2002). Here, CXCR4+U2OS cells were treated with RPA/DNA polyplexes or AMD3100 before incubation with 100 ng/mL of phorbol 12-myristate 13-acetate (PMA) and the cells were imaged by fluorescence microscope (FIG. 28). The results show that internalization of CXCR4 receptor was not inhibited by RPA/DNA polyplexes similarly to AMD3100 when the cells were stimulated with phorbol myristate (PMA).

Figure 29:
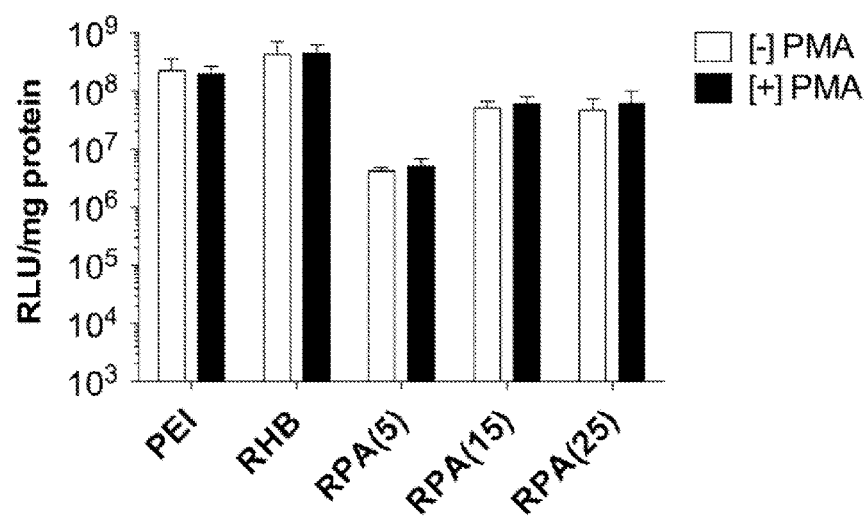
FIG. 29 depicts the effect of phorbol myristate (+/−PMA) treatment on transfection activity of RPA/DNA prepared at w/w 5, 15 and 25.

To further confirm if CXCR4 was involved in the transfection process of the polyplexes, the effect of PMA treatment was evaluated on transfection activity of RPA/DNA polyplexes. The experiment was conducted using the same conditions as described above, except that the cells were co-incubated with polyplexes and 100 ng/mL of PMA in serum-free medium for 4 h. No cytotoxicity of PMA was observed under the used experimental conditions. The results show that PMA did not enhance transfection of RPA polyplexes despite its ability to trigger internalization of the CXCR4 receptor by an alternative pathway from CXCL12 (FIG. 29). This finding provides further support for the lack of involvement of the CXCR4 receptor in transfection activity of RPA/DNA.

Figure 30A:
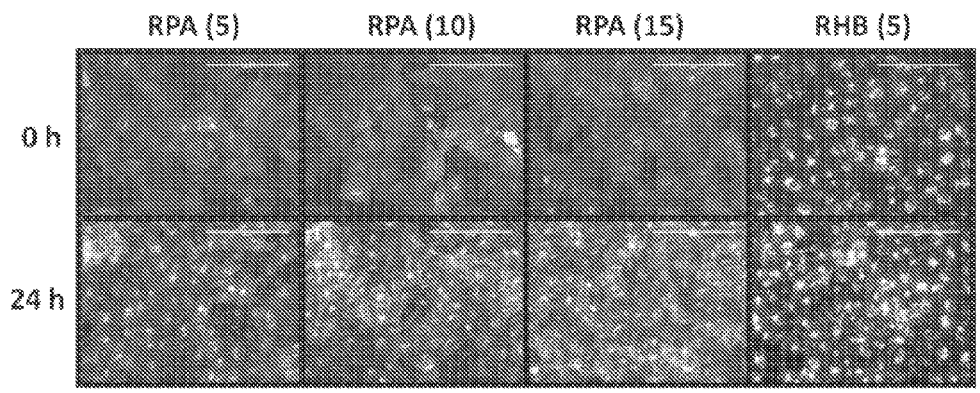
FIG. 30 shows simultaneous transfection and CXCR4 inhibition by RPA/DNA polyplexes in CXCR4+U2OS cells. a) Cells treated with RPA/DNA polyplexes (RPA/DNA w/w=5, 10 and 15) showed CXCR4 inhibition both at 0 h and, a weaker one, at 24 h after polyplex incubation. In contrast, RHB/DNA polyplexes (RHB(5)) showed no CXCR4 antagonism at any time. b) Simultaneously, RPA/DNA polyplexes exhibit similar transfection (luciferase expression) as control RHB polyplexes at 24 h after polyplex incubation.
Figure 30B:
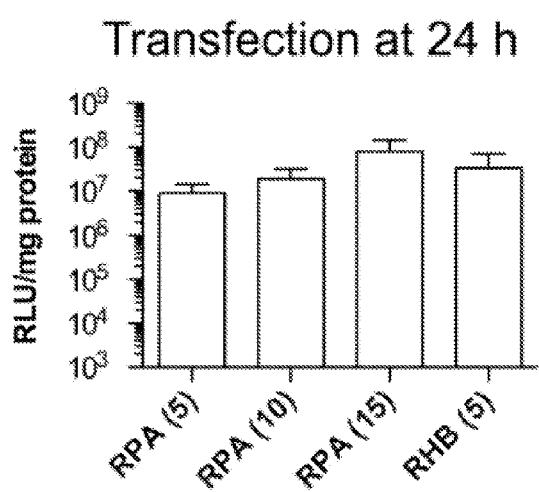

FIG. 30 also shows concurrent CXCR4 inhibition and transfection with RPA/DNA polyplexes. CXCR4+U2OS cells were plated in black 96-well plate with optical bottom 24 h before the experiment at a seeding density of 8,000 cells per well. The cells were incubated with RPA/DNA polyplexes prepared at w/w 5, 10 and 15 (2.35 µg/mL DNA) or RHB/DNA polyplexes (negative control) prepared at w/w 5 in serum-free media. The polyplexes were removed after 4 h incubation and the cells were continued to grow in fresh complete culture media. The luciferase transfection was measured after 24 h. The CXCR4 antagonism was evaluated in the same cells at 0 h and 24 h after polyplex incubation by stimulating the cells with 10 nM hCXCL12. The results show that RPA/DNA polyplexes simultaneously inhibited CXCR4 (FIG. 30a) and mediated effective transfection (FIG. 30b). Additionally, RPA/DNA polyplexes maintained their CXCR4 inhibiting properties even after 24 hours (although the inhibition was not as complete as in the early time point as judged by the reappearance of the punctate fluorescence distribution of the CXCR4 receptor at 24 h in FIG. 30a). In contrast, the negative control (RHB/DNA polyplexes) shows no CXCR4 antagonism at any time point, while mediating similar transfection activity as RPA/DNA. These findings support the mechanism of action in which the free RPA inhibits CXCR4 while the rest of the RPA/DNA polyplex formulation participates in transfection, most likely through nonspecific charge-mediated uptake.

Example 33

Breast Cancer Study Design

A panel of pH-sensitive biodegradable block copolymers (CopCX), such as P(AMD-CBA)DNA polyplex with CXCR4 antagonistic properties can be synthesized. Cytotoxicity, CXCR4 antagonism, CXCR4 receptor binding specificity and gene silencing capability in mouse breast cancer cells 4T1.Luc can be evaluated in vitro using CopCX/siRNA nanocarriers. The best performing nanocarriers can be used to identify therapeutic siRNA that will provide maximum synergy with CXCR4 inhibition in anticancer activity and in inhibition of breast cancer cell invasiveness in vitro. Therapeutic siRNA candidates will include, for example, akt2, HER2, survivin, PARP, and STAT3. The following controls will be used in all in vitro studies: FDA-approved CXCR4 antagonist AMD3100, polycation with no CXCR4 inhibiting activity (poly(ethyleneimine) (PEI)), and scrambled control siRNA. The best performing CopCX/siRNA nanocarrier will be advanced to in vivo studies in metastatic breast cancer model 4T1.Luc. Two experimental setups (with and without primary tumor removal) will be used to test the anti-cancer and anti-metastatic activity of CopCX/siRNA in vivo. The mice will be treated with multiple intravenous doses of CopCX/siRNA. Control animals will be treated using the same administration regimen with CopCX/scrambled siRNA, free CopCX, PEI/siRNA, free PEI, and saline. Tumor growth and metastasis will be monitored by bioluminescence imaging. Antitumor efficacy will be evaluated using tumor growth delay and inverse of tumor growth inhibition analysis.

For example, two cyclam monomers with different side chains can be synthesized and used for the synthesis of CopCX. Stabilizing poly(ethylene glycol) (PEG) block can be conjugated via a reversible linkage to take advantage of acidic tumor microenvironment for tumor-selective PEG removal. Structure-activity relationships (SAR) studies with the assembled CopCX/siRNA nanocarriers will identify those with maximum CXCR4 antagonism and siRNA silencing activity in mouse mammary carcinoma cells stably expressing luciferase (4T1.Luc).

While not being bound to a particular theory, it is believed that CXCR4 antagonism of CopCX will depend on the surface presentation and accessibility of the cyclam moieties and on the molecular weight of the polymers. Thus, CopCX with several different molecular weights (4-20 kDa) using the two monomers with different side chains can be tested for cyclam accessibility. The cationic block can be prepared first with terminal acrylate groups for subsequent PEG 2 kDa conjugation as previously shown (Chen, J., C. Wu, and D. Oupicky, "Bioreducible Hyperbranched Poly(amido amine)s for Gene Delivery." Biomacromolecules, 2009, 10(10): p. 2921-2927; Wu et al., "2A(2)+BB'B" approach to hyperbranched poly(amino ester)s." Macromolecules, 2005, 38(13): p. 5519-5525). The cyclam Boc-protecting groups will be removed and PEG will be conjugated using thiol addition to the terminal acrylate via a linker containing either hydrazone or orthoester groups. Both linkers are well established as rapidly degradable in mildly acidic conditions. Alternatively, PEG may be grafted directly to CopCX backbone by reaction with the cyclam amines to achieve ~1-2 PEG/CopCX substitution using the same X linkers.

$IC_{10}$ of CopCX in 4T1.Luc cells can be obtained in MTS assays and used to obtained information to establish non-toxic working concentration range (defined as concentrations <$IC_{10}$) for the subsequent experiments. CXCR4 antagonism of CopCX will be studied using SDF-1-mediated CXCR4 receptor redistribution using a commercially available assay (Li et al., "Dual-Function CXCR4 Antagonist Polyplexes To Deliver Gene Therapy and Inhibit Cancer Cell Invasion." Angew. Chem. Int. Ed. Engl., 2012). Specificity of CopCX binding to CXCR4 receptor will be then evaluated from the ability of CopCX to displace bound anti-CXCR4 mAb using flow cytometry (Khan et al., "Fluorescent CXCR4 chemokine receptor antagonists: metal activated binding." Chem. Commun., 2007(4): p. 416-418; Nimmagadda et. al., "Molecular Imaging of CXCR4 Receptor Expression in Human Cancer Xenografts with [Cu-64] AMD3100 Positron Emission Tomography." Cancer Res., 2010, 70(10): p. 3935-3944). A negative control for non-specific background of isotype control mAb will be used. The silencing activity of the CopCX/siRNA nanocarriers will be evaluated using anti-Luc siRNA in 4T1.Luc cells using previously published study (Manickam et al., "Effect of innate glutathione levels on activity of redox-responsive gene delivery vectors." J. Controlled Rel., 2010, 141(1): p. 77-84). Simultaneous siRNA transfection and CXCR4 antagonism of the best CopCX will be confirmed and the composition of CopCX/siRNA nanocarriers will be optimized in experiments that will evaluate siRNA silencing and CXCR4 antagonism in 4T1.Luc. CopCX will be rank-ordered based on their silencing and CXCR4 inhibition activities.

Anticancer activity of CopCX/siRNA nanocarriers formulated with the proposed siRNAs will be determined by MTS assay. The goal will be to identify active dose ranges of the nanocarriers and to adjust relative content of CopCX and siRNA to maximize the combination effect with CXCR4 inhibition. The extent and specificity of silencing of individual siRNAs will be verified by western blot.

To determine the maximum tolerated dose (MTD), CopCX will be administered intravenously (i.v.) to tumor-free mice at increasing doses. The MTD will be defined as the dose which causes less than 20% body weight loss with an overall projected lethality under 10%. At defined endpoints (morbidity, 20% weight loss, or tissue harvest), mice will be humanely euthanized with appropriate tissues (liver, kidneys, lungs, heart, spleen) and serum harvested for further analyses: histopathology, cytokine induction (TNF, IL-6, IFN-α), and blood levels of the liver enzymes alanine aminotransferase and aspartate aminotransferase.

The antitumor activity of CopCX/siRNA nanocarriers against 4T1.Luc tumor will be tested in two types of experiments. First, orthotopic 4T1.Luc tumors will be established by mammary fat pad cell injection in Balb/c mice (female, 7-8 wks, 22-24 g) using previously published protocols (Lelekakis et al., "A novel orthotopic model of breast cancer metastasis to bone." Clin Exp Metastasis, 1999, 17(2): p. 163-170; Aslakson, C. J. and F. R. Miller, "Selective events in the metastatic process defined by analysis of the sequential dissemination of subpopulations of a mouse mammary tumor." Cancer Res, 1992, 52(6): p. 1399-405; Olkhanud et al., "Breast Cancer Lung Metastasis Requires Expression of Chemokine Receptor CCR4 and Regulatory T Cells." Cancer Res., 2009, 69(14): p. 5996-6004; Tao et al., "Imagable 4T1 model for the study of late stage breast cancer." BMC Cancer, 2008, 8(1): p. 228). CopCX/siRNA nanocarriers will be prepared with the best performing siRNA as identified above. The treatment can commence, e.g., 3 days after cell injection. This experimental setup will allow to evaluate activity of the nanocarriers against primary tumor and in preventing metastatic dissemination. In the second experimental setup, the primary tumors will be established and then surgically removed by en-bloc excision when they are upstaged to ~500 mg and metastases are detected in the lung by BLI. Treatment with CopCX will commence after primary tumor removal, which will help to evaluate activity of the nanocarriers against established metastasis after primary tumor removal.

In both of the above types of experiments, the mice will be formally randomized and treated every two to five days (3-5 courses in total) with i.v. injection of three different doses of CopCX/siRNA nanocarriers using a dose range determined from the MTD study. Control animals will be treated using the same administration regimen with (i) CopCX/siRNA nanocarrier prepared with scrambled siRNA control, (ii) free CopCX, (iii) PEI/siRNA nanocarrier with therapeutic siRNA, (iv) PEI, and (v) saline. Total of about 200 Balb/c mice will be used: [3 doses*5 mice/group*5 treatments]+[3 doses*7 mice/group*5 treatments=180+20 for experimental complications and untreated controls=200]. Group size can be increased to, e.g., 7 mice in the second type of experimental setup to account for primary tumor regrowth and complications due to tumor removal surgery. Animal weight, tumor growth and total tumor load will be monitored, and growth curves will be constructed from the bioluminescence intensity of the metastatic lesions and by measuring the size of the primary tumors by calipers. All animals in the study will be necropsied and remaining tumor (if any) and liver, spleen, lung, and adjacent lymph nodes will be harvested. Tissue sections will be used for (i) H&E staining and histopathological evaluations, (ii) immunohistochemical (IHC) staining with anti-Ki-67 to detect proliferating tumor cells, (iii) TUNEL assay and IHC of activated caspase-3 to detect cells undergoing apoptosis, and (iv) counting of metastasis nodules in tissue sections. The specificity of siRNA silencing will be verified in tumor homogenates by western blot. Antitumor efficacy of the CopCX/siRNA nanocarriers will be analyzed using the following quantitative endpoints: (i) tumor growth delay (T-C), where T is median days for the treatment group to reach a predetermined size, and C is median days for the control group tumors to reach the same size (tumor-free survivors are excluded and tabulated separately); (ii) % T/C (inverse of tumor growth inhibition), where treated/control tumors are measured when control group tumors reach ~700-1200 mg. The median for each group is determined as a non-quantitative measure of antitumor effectiveness. T/C<42% is considered significant activity by the NCI; T/C<10% is highly significant activity. The Kaplan-Meier method will be used to analyze the survival curves.

Example 34

Lung Cancer (LCa) Study Design

Many preclinical and clinical studies observed significant correlation between expression of CXCR4 chemokine receptor and metastasis in LCa. CXCR4 expression is associated with poor survival and aggressive type of cancer both in small cell lung cancer (SCLC) and nonsmall cell lung cancer (NSCLC). Consistent with the seed-and-soil hypothesis of metastatic dissemination (Burger, J. A. and T. J. Kipps, "CXCR4: a key receptor in the crosstalk between tumor cells and their microenvironment." Blood, (2006) 107: 1761-1767), LCa cells utilize CXCR4 and its ligand CXCL12 to metastasize to distant sites. Thus as expected, the primary sites of LCa metastasis (lymph nodes, bone, liver) are also sites with high levels of CXCL12 expression (Gangadhar, T., S. Nandi, and R. Salgia, "The role of chemokine receptor CXCR4 in lung cancer." Cancer Biology & Therapy, (2010) 9: 409-416). CXCR4/CXCL12 axis regulates survival, proliferation, migration and invasion of LCa cells by activating signaling pathways such as MAPK and PI3K pathways (Burger et al., "Functional expression of CXCR4 (CD184) on small-cell lung cancer cells mediates migration, integrin activation, and adhesion to stromal cells." Oncogene, (2003) 22: 8093-8101).

COPCX formulations with anti-EGFR siRNA will be tested. Four other candidate siRNAs (akt2, survivin, PARP, and STAT3) that have been validated as promising in LCa treatment will be tested too.

Lewis lung carcinoma stably expressing luciferase (LL/2-luc) will be used to test the anticancer and anti-metastatic activity of COPCX/siRNA in vivo. LL/2-luc has the capability to spontaneously metastasize after subcutaneous and intravenous (i.v.) administration in SCID-bg mice. Tumor growth and metastatic spread can be easily monitored by whole-body bioluminescence imaging (BLI). BLI will be advantageously used for longitudinal noninvasive studies of the COPCX activity. Maximum tolerated dose (MTD) of COPCX will be determined using 6 mice before testing anticancer activity.

Activity of the optimized COPCX/siRNA against subcutaneously implanted LL/2-luc tumor and in preventing its metastatic dissemination will be tested in SCID-bg mice. The mice will be treated every two to five days (3-5 courses in total) with i.v. injection of three different doses of COPCX/siRNA using a dose range determined from the MTD study. Control animals will be treated using the same administration regimen with (i) COPCX/siRNA prepared with scrambled siRNA control, (ii) free CXLip, (iii) DOTAP/siRNA, (iv) saline. Seventy five SCID-bg mice will be used: (3 doses×5 mice/group×4 treatments)=60+15 for experimental complications and untreated controls. Animal weight, tumor growth and total tumor load will be monitored, and growth curves will be constructed from the bioluminescence imaging (BLI) intensity of the metastatic lesions and by measuring the size of the primary tumors by calipers. Animals will be necropsied and tissue sections will be used for (i) H&E staining and histopathological evaluations, (ii) immunohistochemical (IHC) staining with anti-Ki-67 to detect proliferating tumor cells, (iii) TUNEL assay and immunohistochemistry (IHC) of activated caspase-3 to detect cells undergoing apoptosis, and (iv) counting of metastasis nodules in tissue sections. The specificity of siRNA silencing will be verified in tumor homogenates by western blot. Antitumor efficacy of the COPCX/siRNA nanoparticles will be analyzed using the following quantitative endpoints: (i) tumor growth delay (T-C), where T is median days for the treatment group to reach a predetermined size, and C is median days for the control group tumors to reach the same size (tumor-free survivors are excluded and tabulated separately); (ii) % T/C (inverse of tumor growth inhibition), where treated/control tumors are measured when control group tumors reach ~700-1200 mg. The median for each group is determined as a non-quantitative measure of antitumor effectiveness. T/C<42% is considered significant activity by the National Cancer Institute (NCI); T/C<10% is highly significant activity.

The invention claimed is:

1. A polymer comprising structural units of a CXCR4 inhibiting moiety and either (i) a structural unit of Formula 11, (ii) a structural unit of Formula 22, (iii) structural units of Formulae 11 and 22, (iv) structural units of Formulae 11 and 88, (v) structural units of Formulae 22 and 88, (vi) structural units of Formulae 11, 22, and 88, the structural units of Formulae 11, 22, and 88 corresponding to the following structures:

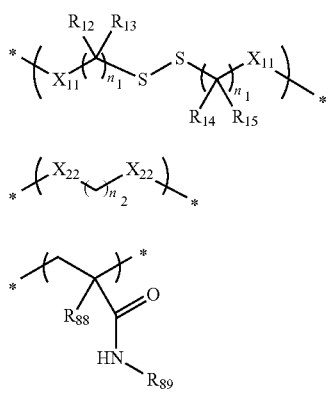

Formula 11

Formula 22

Formula 88 wherein $X_{11}$ and $X_{22}$ are independently —NH—C(O)—CH$_2$CH$_2$—, —O—C(O)—CH$_2$CH$_2$—, —C(O)O—, —C(O)—, or —NH—C(O)—; $R_{12}$, $R_{13}$, $R_{14}$, $R_{15}$ are independently hydrogen, alkyl, or substituted alkyl; $R_{88}$ and $R_{89}$ are independently alkyl or substituted alkyl; $n_1$ is independently an integer from 1 to 4; and $n_2$ is an integer from 1 to 8, wherein CXCR4 inhibiting moiety is derived from a cyclam compound and the cyclam compound corresponds to Formula 5, wherein Formula 5 corresponds to the following structure:

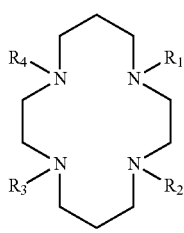

Formula 5 wherein $R_1$ is —$R_8$—NH$_2$;

$R_2$, $R_3$, and $R_4$ are hydrogen;

and $R_8$ is —CH$_2$—C$_6$H$_4$—CH$_2$—N(C(O))t-Bu)-(CH$_2$)$_3$—.

2. The polymer of claim 1 wherein the structural unit corresponds to Formula 11.

3. The polymer of claim 2 wherein $X_{11}$ is —NH—C(O)—CH$_2$CH$_2$— and $R_{12}$, $R_{13}$, $R_{14}$, $R_{15}$ are hydrogen.

4. The polymer of claim 1 wherein $R_{12}$ and $R_{14}$ are hydrogen and $R_{13}$ and $R_{15}$ are —C(O)O-alkyl.

5. The polymer of claim 4 wherein $X_{11}$ is —NH—C(O)—CH$_2$CH$_2$— and $n_1$ is 2.

6. The polymer of claim 1 wherein the structural unit corresponds to Formula 22.

7. The polymer of claim 6 wherein $X_{22}$ is —NH—C(O)—CH$_2$CH$_2$— or —O—C(O)—CH$_2$CH$_2$—.

8. The polymer of claim 7 wherein $X_{22}$ is —NH—C(O)—CH$_2$CH$_2$— and $n_2$ is an integer from 4 to 6.

9. The polymer of claim 1 wherein the structural units correspond to Formulae 11 and 22.

10. The polymer of claim 1 comprising a structural unit of Formula 88.

11. The polymer of claim 10 wherein $R_{88}$ is methyl and $R_{89}$ is 2-hydroxypropyl.

12. The polymer of claim 1 wherein the polymer further comprises an amine structural unit of Formula 33, the amine structural unit of Formula 33 corresponding to the following structure:

Formula 33 wherein $R_{30}$ is $C_2$ to $C_{12}$ alkylene, arylene, or $C_2$ to $C_{12}$ alkylene wherein one or more of the —CH$_2$— groups of the alkylene group is replaced with an amine;

$R_{31}$ and $R_{32}$ are independently hydrogen, alkyl or aryl.

13. A polyplex comprising a polymer of claim 1 and a nucleic acid.

14. The polyplex of claim 13 wherein the nucleic acid is plasmid DNA, shRNA, siRNA or microRNA.

15. A pharmaceutical composition comprising a pharmaceutically acceptable excipient and a polyplex of claim 13.

16. The polymer of claim 1 wherein the structural unit corresponds to Formula 11, $X_{11}$ is —NH—C(O)—CH$_2$CH$_2$—, $R_{12}$, $R_{13}$, $R_{14}$, $R_{15}$ are independently hydrogen, and $n_1$ is 2.

17. The polymer of claim 8 wherein $n_2$ is 6.

* * * * *